United States Patent
Wang et al.

(10) Patent No.: US 12,359,253 B2
(45) Date of Patent: *Jul. 15, 2025

(54) METHOD OF IN SITU GENE SEQUENCING

(71) Applicant: The Board of Trustees of the Leland Stanford Junior University, Stanford, CA (US)

(72) Inventors: Xiao Wang, Stanford, CA (US); William E. Allen, Albany, CA (US); Karl A. Deisseroth, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1089 days.

This patent is subject to a terminal disclaimer.

(21) Appl. No.: 17/045,734

(22) PCT Filed: Apr. 4, 2019

(86) PCT No.: PCT/US2019/025835
§ 371 (c)(1),
(2) Date: Oct. 6, 2020

(87) PCT Pub. No.: WO2019/199579
PCT Pub. Date: Oct. 17, 2019

(65) Prior Publication Data
US 2021/0164039 A1 Jun. 3, 2021

Related U.S. Application Data

(60) Provisional application No. 62/808,159, filed on Feb. 20, 2019, provisional application No. 62/687,490, (Continued)

(51) Int. Cl.
C12Q 1/6874 (2018.01)
C12Q 1/6876 (2018.01)

(52) U.S. Cl.
CPC ......... *C12Q 1/6874* (2013.01); *C12Q 1/6876* (2013.01); *C12Q 2600/136* (2013.01); *C12Q 2600/158* (2013.01)

(58) Field of Classification Search
CPC ............... C12Q 1/6874; C12Q 1/6876; C12Q 2600/136; C12Q 2600/158
(Continued)

(56) References Cited

U.S. PATENT DOCUMENTS 6,235,502 B1  5/2001  Weissman et al.
6,316,229 B1  11/2001  Lizardi et al.
(Continued)

FOREIGN PATENT DOCUMENTS

CN  101643732 A  2/2010
CN  102220431 A  10/2011
(Continued)

OTHER PUBLICATIONS

Shah et al. Single-molecule RNA detection at depth by hybridization chain reaction and tissue hydrogel embedding and clearing. Development. 143, 2016, 2862-2867. Supplementary Information, 28 pages. (Year: 2016).*

(Continued)

*Primary Examiner* — Aaron A Priest
*Assistant Examiner* — Randi Lynn Beil
(74) *Attorney, Agent, or Firm* — Jenny L. Buchbinder; Bozicevic, Field & Francis LLP

(57) ABSTRACT

Provided herein are devices, methods, and systems for in situ gene sequencing of a target nucleic acid in a cell in an intact tissue. Methods of screening a candidate agent to determine whether the candidate agent modulates gene expression of a nucleic acid in a cell in an intact tissue are also provided herein.

28 Claims, 68 Drawing Sheets

Related U.S. Application Data filed on Jun. 20, 2018, provisional application No. 62/655,052, filed on Apr. 9, 2018.

(58) Field of Classification Search
USPC .......................................................... 506/4
See application file for complete search history.

(56) References Cited

U.S. PATENT DOCUMENTS

| | | |
|---|---|---|
| 6,558,928 B1 | 5/2003 | Landegren et al. |
| 8,497,069 B2 | 7/2013 | Hutchison et al. |
| 9,791,409 B2 | 10/2017 | Gordon et al. |
| 10,138,509 B2 | 11/2018 | Church et al. |
| 10,227,639 B2 | 3/2019 | Levner et al. |
| 10,494,662 B2 | 12/2019 | Church et al. |
| 10,829,814 B2 | 11/2020 | Fan et al. |
| 10,961,566 B2 | 3/2021 | Chee |
| 11,008,608 B2 | 5/2021 | Samusik et al. |
| 11,021,737 B2 | 6/2021 | Church et al. |
| 11,078,520 B2 | 8/2021 | Church et al. |
| 11,098,303 B2 | 8/2021 | Zhuang |
| 11,111,521 B2 | 9/2021 | Church et al. |
| 11,293,051 B2 | 4/2022 | Church et al. |
| 11,293,052 B2 | 4/2022 | Church et al. |
| 11,293,054 B2 | 4/2022 | Levner et al. |
| 11,299,767 B2 | 4/2022 | Church et al. |
| 11,377,689 B2 | 7/2022 | Beechem et al. |
| 11,542,554 B2 | 1/2023 | Daugharthy et al. |
| 11,549,136 B2 | 1/2023 | Church et al. |
| 11,566,276 B2 | 1/2023 | Church et al. |
| 11,566,277 B2 | 1/2023 | Church et al. |
| 11,639,518 B2 | 5/2023 | Church et al. |
| 11,656,447 B2 | 5/2023 | Tsia et al. |
| 2005/0112639 A1 | 5/2005 | Wang et al. |
| 2006/0141501 A1 | 6/2006 | Friend et al. |
| 2010/0120129 A1 | 5/2010 | Amshey |
| 2012/0003657 A1 | 1/2012 | Myllykangas et al. |
| 2013/0045872 A1 | 2/2013 | Zhou et al. |
| 2013/0178372 A1 | 7/2013 | Geiss et al. |
| 2014/0162892 A1 | 6/2014 | Mir |
| 2014/0170654 A1 | 6/2014 | Landegren et al. |
| 2015/0377886 A1 | 12/2015 | Ciceri et al. |
| 2016/0129437 A1 | 5/2016 | Kayyem et al. |
| 2016/0377524 A1 | 12/2016 | Martin et al. |
| 2017/0211133 A1* | 7/2017 | Landegren ............ C12Q 1/6876 |
| 2018/0017525 A1 | 1/2018 | Gordon et al. |
| 2018/0119219 A1* | 5/2018 | Chen .................... C12Q 1/6874 |
| 2018/0216161 A1 | 8/2018 | Chen et al. |
| 2020/0199667 A1 | 6/2020 | Erickstad et al. |
| 2021/0164039 A1 | 6/2021 | Wang et al. |
| 2021/0238665 A1 | 8/2021 | Samusik et al. |
| 2021/0262018 A1 | 8/2021 | Bava et al. |
| 2021/0293693 A1 | 9/2021 | Bharadwaj et al. |
| 2023/0109070 A1 | 4/2023 | Richman et al. |
| 2023/0323437 A1 | 10/2023 | Chen et al. |
| 2024/0144704 A1 | 5/2024 | Wang et al. |
| 2024/0248038 A1 | 7/2024 | Deisseroth et al. |
| 2024/0254545 A1 | 8/2024 | Wang et al. |
| 2024/0254553 A1 | 8/2024 | Deisseroth et al. |
| 2024/0254554 A1 | 8/2024 | Deisseroth et al. |
| 2024/0257912 A1 | 8/2024 | Deisseroth et al. |
| 2024/0263228 A1 | 8/2024 | Deisseroth et al. |
| 2024/0294973 A1 | 9/2024 | Wang et al. |

FOREIGN PATENT DOCUMENTS

| | | |
|---|---|---|
| CN | 103602719 A | 2/2014 |
| CN | 104662165 A | 5/2015 |
| EP | 2270205 A2 | 1/2011 |
| EP | 2794928 B1 | 2/2019 |
| EP | 2971184 B1 | 4/2019 |
| EP | 3578666 A1 | 12/2019 |
| EP | 3425063 B1 | 6/2023 |
| EP | 4108782 B1 | 6/2023 |
| JP | 2005511058 A | 4/2005 |
| JP | 2009518009 A | 5/2009 |
| WO | WO2001061037 A1 | 8/2011 |
| WO | WO2012005595 A2 | 1/2012 |
| WO | WO2012110899 A2 | 8/2012 |
| WO | WO2012160083 A1 | 11/2012 |
| WO | WO2013173774 A2 | 11/2013 |
| WO | WO2014030066 A2 | 2/2014 |
| WO | WO-2014176575 A1 * | 10/2014 ........... C12Q 1/6806 |
| WO | 2017019481 A1 | 2/2017 |
| WO | 2017096248 A1 | 6/2017 |
| WO | 2017147483 A1 | 8/2017 |
| WO | WO2018033528 A1 | 2/2018 |
| WO | WO2018136856 A1 | 7/2018 |
| WO | WO2019016048 A1 | 1/2019 |
| WO | WO2019199579 A1 | 10/2019 |
| WO | WO2019222284 A1 | 11/2019 |
| WO | WO2020214885 A1 | 10/2020 |
| WO | WO2020240025 A1 | 12/2020 |
| WO | WO2021076770 A1 | 4/2021 |
| WO | WO2020148769 A1 | 7/2021 |
| WO | WO2022178274 A1 | 8/2022 |
| WO | WO2022236011 A1 | 11/2022 |
| WO | WO2022246181 A2 | 11/2022 |
| WO | WO2022246242 A1 | 11/2022 |
| WO | WO2022246269 A1 | 11/2022 |
| WO | WO2022246275 A1 | 11/2022 |
| WO | WO2022246279 A1 | 11/2022 |
| WO | WO2022251586 A1 | 12/2022 |
| WO | WO2022261255 A1 | 12/2022 |
| WO | WO2023278409 A1 | 1/2023 |
| WO | WO2023018756 A1 | 2/2023 |

OTHER PUBLICATIONS

Yang et al. Single-cell phenotyping within transparent intact tissue through whole-body clearing. Cell. 158, 2014, 945-958. (Year: 2014).*
Thermo Scientific. Tech Tip #45 Anneal complementary pairs of oligonucleotides. 2009. 2 pages. (Year: 2009).*
Fischer et al. Fixation and permeabilization of cells and tissues. CSH Protocols. 3, 2008, 1-2. (Year: 2008).*
Tomer et al. Advanced CLARITY for rapid and high-resolution imaging of intact tissues. Nat Protoc. 9, 2014, 1682-1697. (Year: 2014).*
Conchello et al. Optical sectioning microscopy. Nature Methods. 2, 2005, 920-931. (Year: 2005).*
PCT/US2019/025835, International Search Report dated Jul. 1, 2019, 1-2.
Zhang et al., (2018) "Detection of nucleic acids with a novel stem-loop primer rolling circle amplification technique.", Biotechniques, 64(2):69-80.
Zhong et al., (2001) "Visualization of ollgonucleotide probes and point mutations in interphase nuclei and DNA fibers using rolling circle DNA amplification.", Proc Natl Acad Sci USA, 98(7):3940-3945.
Wang et al., (2018) "Three-dimensional intact-tissue sequencing of single cell transcriptional states.", Science, 361 (6400):1-22.
Crosetto et al., (2015) "Spatially resolved transcriptomics and beyond.", Nat Rev Genet, 16(1):57-66.
Lein et al., (2017) "The promise of spatial transcriptomics for neuroscience in the era of molecular cell typing.", Science, 358:64-69.
Chen et al., (2015) "Spatially resolved, highly multiplexed RNA profiling in single cells.", Science, 348:aaa6090.
Lee et al., (2014) Highly multiplexed subcellular RNA sequencing in situ., Science, 343:1360-1363.
Sylwestrak et al., (2016) "Multiplexed intact-tissue transcriptional analysis at cellular resolution.", Cell 164:792-804.
Shah et al., (2016) "Single-molecule RNA detection at depth by hybridization chain reaction and tissue hydrogel embedding and clearing." Development, 143:2862-2867.
Moffitt et al., (2016) "High-performance multiplexed fluorescence in situ hybridization in culture and tissue with matrix imprinting and clearing.", Proc. Natl. Acad. Sci. U.S.A. 113:14456-14461.

(56) References Cited

OTHER PUBLICATIONS

Lee et al., (2015) "Fluorescent in situ sequencing (FISSEQ) of RNA for gene expression profiling in intact cells and issues.", Nat. Protoc. 10:442-458.
Lerner et al., (2016) "Communication in neural circuits: tools, opportunities, and challenges.", Cell 164:1136-1150.
Lubeck et al., (2012) "Single-cell systems biology by super-resolution imaging and combinatorial labeling", Nat. Methods, 9:743-748.
Deng et al., (2018) "DNA-Sequence-Encoded Rolling Circle Amplicon for Single-Cell RNA Imaging", Chem, 4:1373-1386.
Sountoulidis et al., (2020) "Scrinshot enables spatial mapping of cell states in tissue sections with single-cell resolution", PLOS Biology, 18(11):e3000675, XP055908911.
Sun et al., (2021) "Integrating barcoded neuroanatomy with spatial transcriptional profiling enables identification of gene correlates of projections", Nature Neuroscience, Nature Publishing Group US, 24(6):873-885.
U.S. Appl. No. 18/564,338 filed Nov. 27, 2023.
U.S. Appl. No. 18/682,160 filed Feb. 8, 2024.
Angelo et al. (2014) "Multiplexed ion beam imaging (MIBI) of human breast tumors", Nat Med. Pages 436-442, 20(4), Springer, Berlin, Germany.
Alon et al., (2021) "Expansion sequencing: Spatially precise in situ transcriptomics in intact biological systems", Science, 371(481):1-14.
Bendall et al.(2011) "Single-cell mass cytometry of differential immune and drug responses across a human hematopoietic continuum", Science, pp. 687-696, vol. 332, Issue 6030, American Association for the Advancement of Science, Washington, D.C.
Chen et al. (2016) "Nanoscale imaging of RNA with expansion microscopy. Nat. Methods", 13:679-684.
Chen et al., (2018) "Efficient in situ barcode sequencing using padlock probe-based BaristaSeq", Nucleic Acids Res, 46(4):1-10.
Chen et al., (2019) "High-Throughput Mapping of Long-Range Neuronal Projection Using In Situ Sequencing", Cell, 179(3):772-786.
Chen et al., (2024) "Branched chemically modified poly(A) tails enhance the translation capacity of mRNA", Nature Biotechnology, pp. 1-29.
Clausson et al., (2015) "Compaction of rolling circle amplification products increases signal integrity and signal-to-noise ratio", Scientific reports, 5(12317):1-10.
Fredriksson et al. (2002) "Protein detection using proximity-dependent DNA ligation assays", Nat Biotechnol, pp. 473-477, 20, Springer, Berlin, Germany.
Flow cytometry from Wikipedia. Printed on Jul. 6, 2020.
Gyllborg et al., (2020) "Hybridization-based in situ sequencing (HybISS) for spatially resolved transcriptomics in human and mouse brain tissue", Nucleic Acids Research, 48(19)1-11.
He et al., (2021) "ClusterMap for multi-scale clustering analysis of spatial gene expression", Nature Communications, 12(5909):1-13.
Ke et al., (2013) "In situ sequencing for RNA analysis in preserved tissue and cells.", Nat. Methods, 10:857-860.
Kebschull et al., (2020) "Cerebellar nuclei evolved by repeatedly duplicating a conserved cell-type set", Science 370(6523):1-26.
Larsson et al., (2010) "In situ detection and genotyping of individual mRNA molecules", Nature Methods, pp. 395-397, (7), Nature, London, United Kingdom.
Millard et al., 2006 "Detection of infectious haematopoietic necrosis virus and infectious salmon anameia virus by molecular padlock amplification". Journal of Fish Diseases, vol. 29, pp. 201-213.
Mondal et al., (2018) "Highly multiplexed single-cell in situ RNA and DNA analysis with bioorthogonal cleavable fluorescent oligonucleotides", Chem. Sci, 9:2909-2917.
Mota et al., (2022) "Simultaneous visualization of DNA loci in single cells by combinatorial multi-color iFISH", Scientific data, 9(47):1-15.
Nawy et al., (2014) "In situ sequencing", Nat Methods, 11(1):29.
Nguyen et al., (2020) "3D mapping and accelerated super-resolution imaging of the human genome using in situ sequencing", Nature methods, 17(8):822-832.
Payne et al., (2021) "In situ genome sequencing resolves DNA sequence and structure in intact biological samples", Science, 371(908):1-14.
Player et al. (2001) "Single-copy gene detection using branched DNA (bDNA) in situ hybridization", J. Histochem. Cytochem, pp. 603-612, vol. 49, Issue 5, The Histochemical Society, Inc., Bethesda, MD.
Porichis et al. (2014) "High-throughput detection of miRNAs and gene-specific mRNA at the single-cell level by flow cytometry", Nature Communications, pp. 1-24 5, 5641, Springer, Berlin, Germany.
PCT/US20/55800 International Search Report, completed Jan. 3, 2021, published Apr. 22, 2021.
Li et al., (2023) "Multimodal Charting of Molecular and Functional Cell States via in Situ Electro-sequencing", Cell, 186(9):2002-2017.
Ren et al., (2023) "Spatiotemporally resolved Transcriptomics Reveals the Subcellular RNA Kinetic Landscape", Nature Methods, 20:695-705.
Shi et al., (2023) "Spatial atlas of the mouse central nervous system at molecular resolution", Nature, 622:552-561.
Soderberg et al.,(2006) "Direct observation of individual endogenous protein complexes in situ by proximity ligation", Nat. Methods, pp. 995-1000, vol. 3, No. 12, Nature, London, United Kingdom.
Sui et al., (2024) "Scalable Spatial Single-cell Transcriptomics and Translatomics in 3d Thick Tissue Blocks", Biorxiv: the Preprint Server for Biology, pp. 1-37.
Sylwestrak et al., (2022) "Cell-type-specific population dynamics of diverse reward computations", Cell, 185, 3568-3587.
Wolf-Yadlin et al. (2006) "Effects of HER2 overexpression on cell signaling networks governing proliferation and migration", Mol Syst Biol, vol. 2, Issue 1, Nature, London, United Kingdom.
Weibrecht et al. (2013) "In situ detection of individual mRNA molecules and protein complexes or post-translational modifications using padlock probes combined with the in situ proximity ligation assay.", Nature Protocols, vol. 8, No. 2, pp. 355-372.
Wu et al., (2023) "Development of Multiomics in situ Pairwise Sequencing (MiP-Seq) for Single-cell Resolution Multidimensional Spatial Omics", bioRxiv, pp. 1-66.
Wu et al., (2024) "Spatial multi-omics at subcellular resolution via high-throughput in situ pairwise sequencing", Nature Biomedical Engineering, 8, pp. 872-889.
Zeng et al., (2023) "Integrative in situ mapping of single-cell transcriptional states and tissue histopathology in an Alzheimer's disease model", Nature Neuroscience, 26(3):430-446.
Zeng et al., (2023) "Spatially resolved single-cell translatomics at molecular resolution", Science, Pages1-23.
Zhang et al., (2013) "A Study of HdEGF1, an EGF-related Gene in the Lower Digestive Tract from Small Abalone Haliotis diversicolor", Journal of Xiamen University, 52(4):1-9.

\* cited by examiner

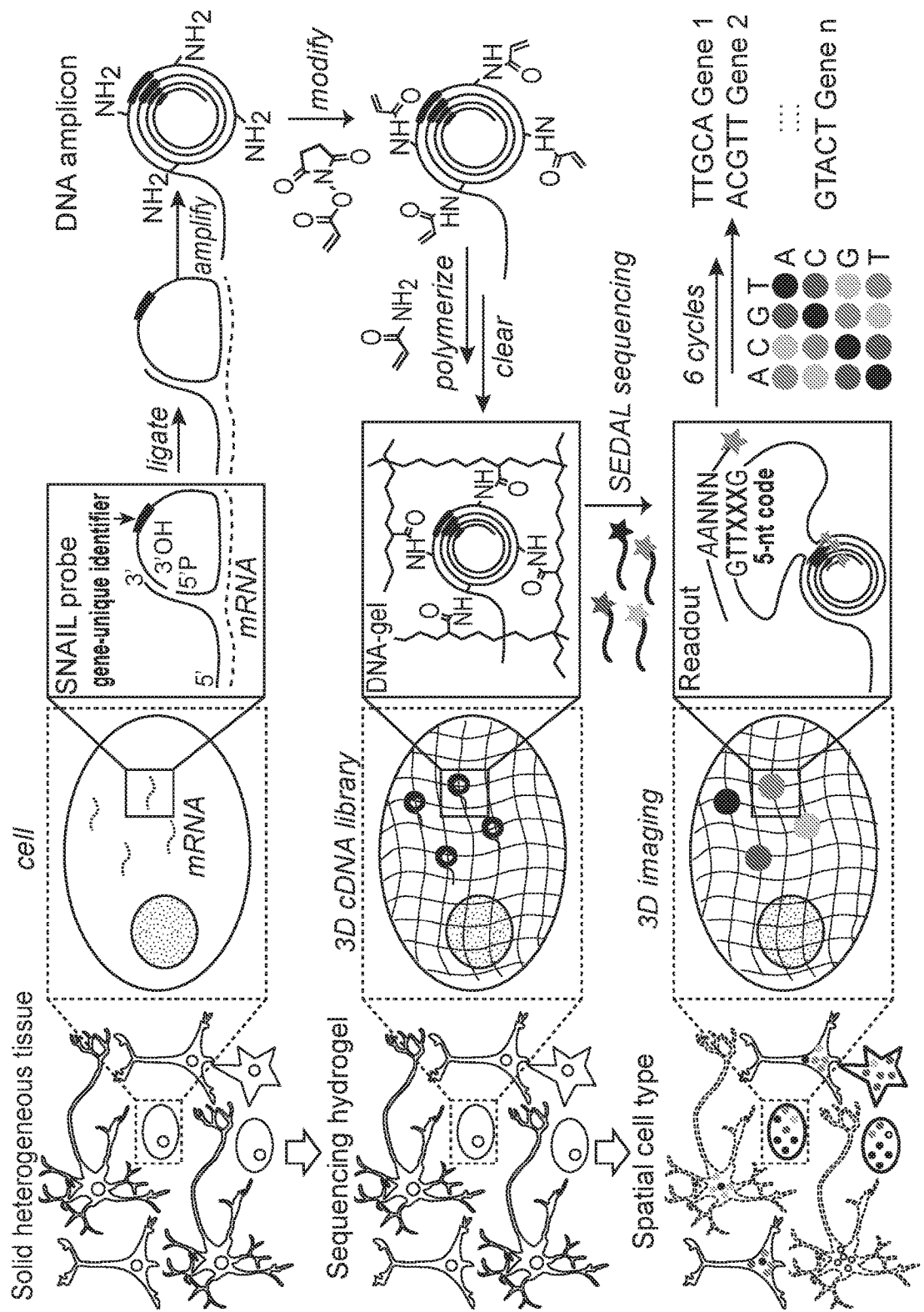

| Methods | Efficiency |
|---|---|
| scRNA-seq | 6%~40% (2) |
| FISSEQ | 0.2% (21); 0.01% (2) |
| Padlock | 30% (with LNA probe, 6); 5% (2) |
| PLAYR | N/A |
| STARmap | no less than scRNA-seq (panel H) |

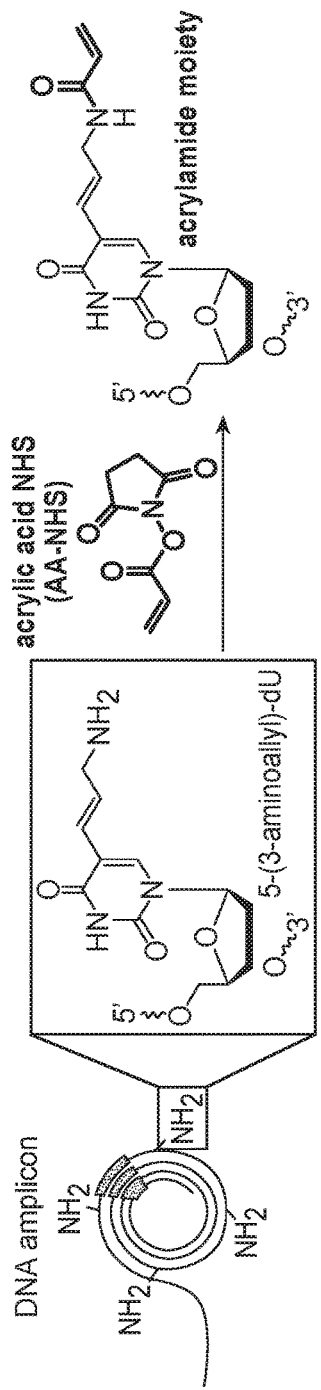
FIG. 3A
FIG. 3B
visual cortex: without hydrogel & clearing
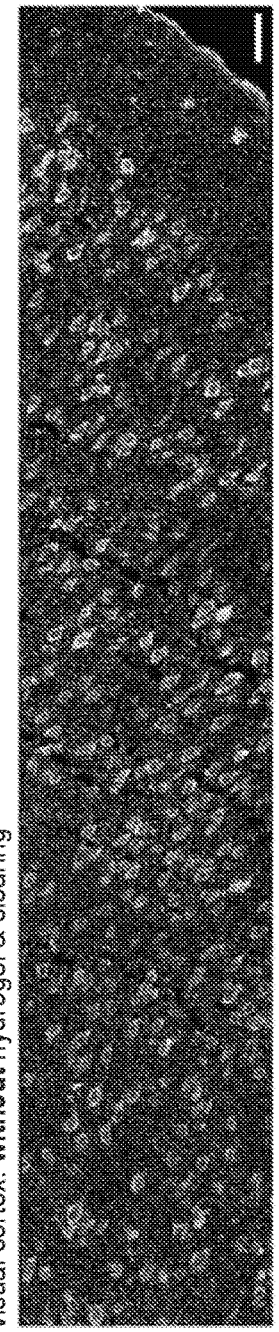
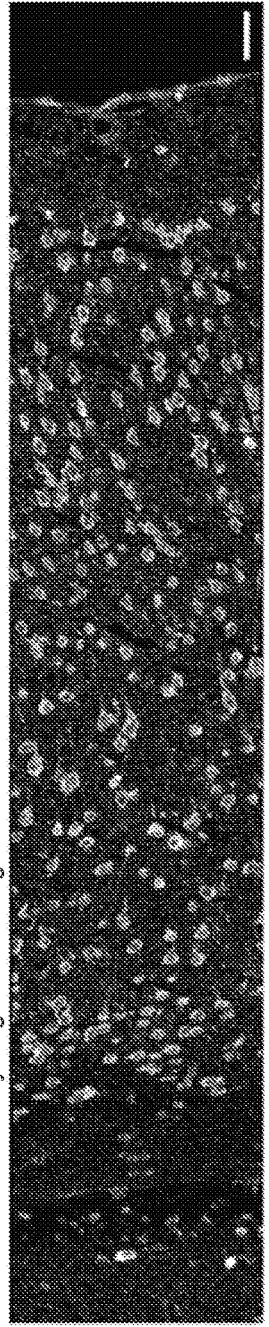
FIG. 3C
visual cortex: with hydrogel & clearing habenula: without hydrogel & clearing habenula: with hydrogel & clearing

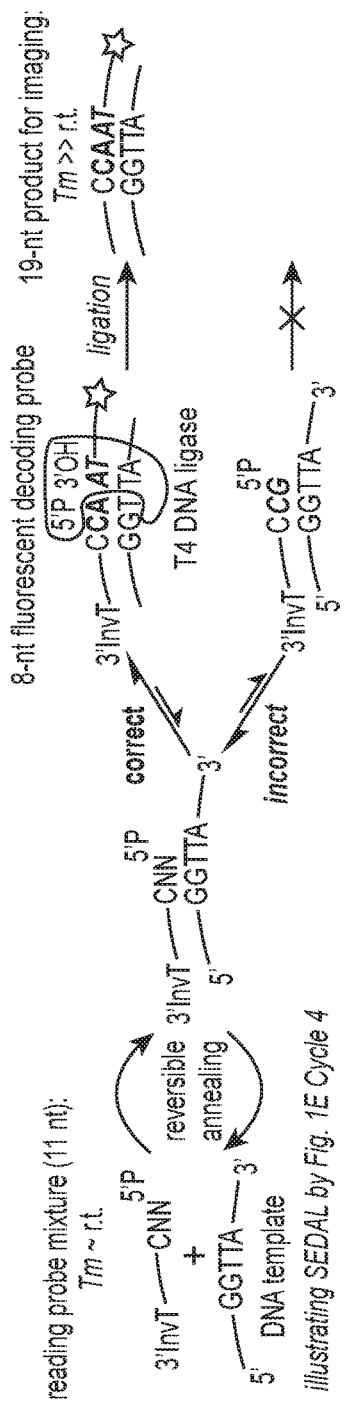
FIG. 4A
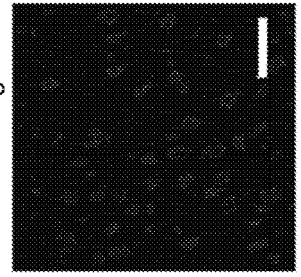
FIG. 4B
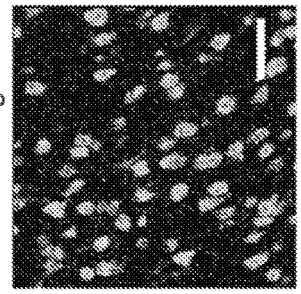
FIG. 4C
SOLiD: signal
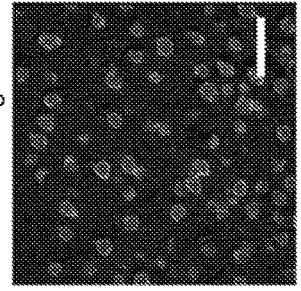
FIG. 4D
SOLiD: background
FIG. 4E
SEDAL: signal
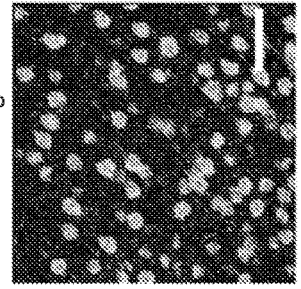
FIG. 4F
SEDAL: background

FIG. 4G 1-base encoding
A C G T one error:
wrong code

Example

| Cycle | 1 | 2 | 3 | 4 | 5 |
|---|---|---|---|---|---|
| Color | | | | | |
| Letter | G | T | T | A | T |
| Results | | | GTTAT | | | cycle 3 error

| Cycle | 1 | 2 | 3 | 4 | 5 |
|---|---|---|---|---|---|
| Color | | | | | |
| Letter | G | T | T | A | T |
| Results | | | GTGAT | | |

FIG. 4H 2-base encoding
A C G T
A
C
G
T correct reads:
GXXXXXG
one error:
GXXXXXH, H ≠ G
rejected Example

| Cycle | 1 | 2 | 3 | 4 | 5 | 6 |
|---|---|---|---|---|---|---|
| Color | | | | | | |
| Letter | GG | GT | TT | TA | AT | TG |
| Results | | | GGTTATG | | | | cycle 3 error

| Cycle | 1 | 2 | 3 | 4 | 5 | 6 |
|---|---|---|---|---|---|---|
| Color | | | | | | |
| Letter | GG | GT | TG | GC | CG | GT |
| Results | | | GGTGCGT | | | |

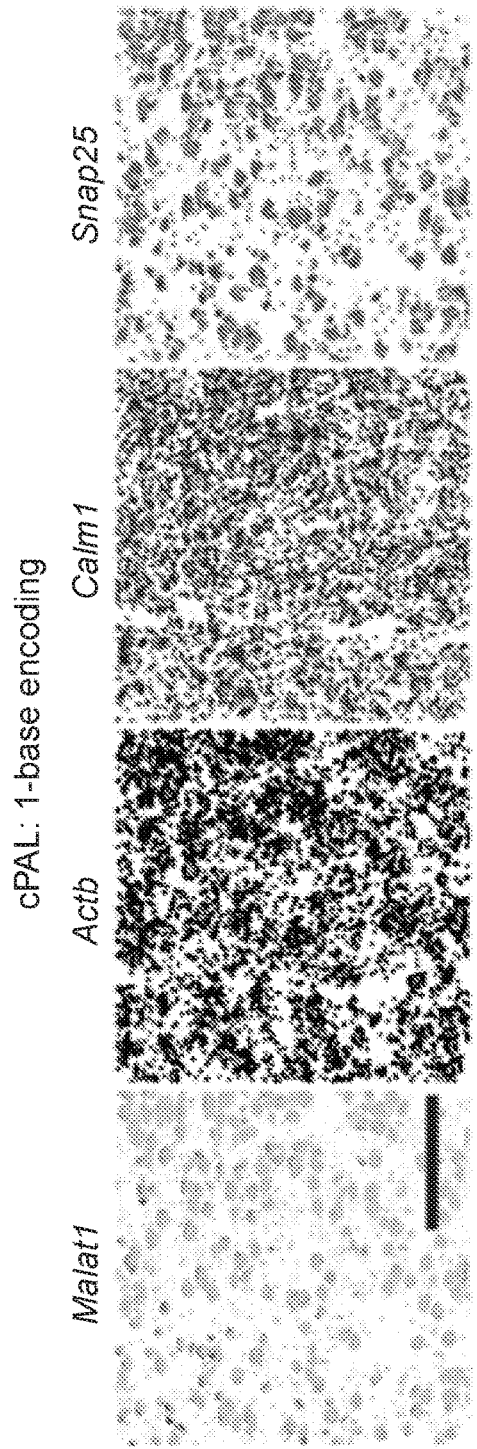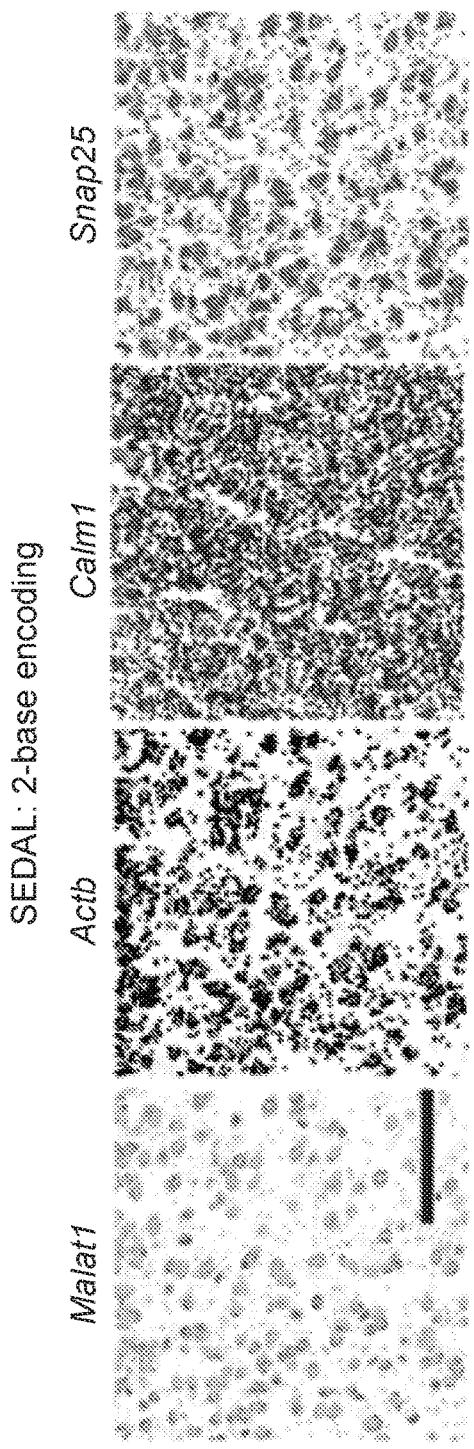
FIG. 4I cPAL: 1-base encoding
FIG. 4J SEDAL: 2-base encoding

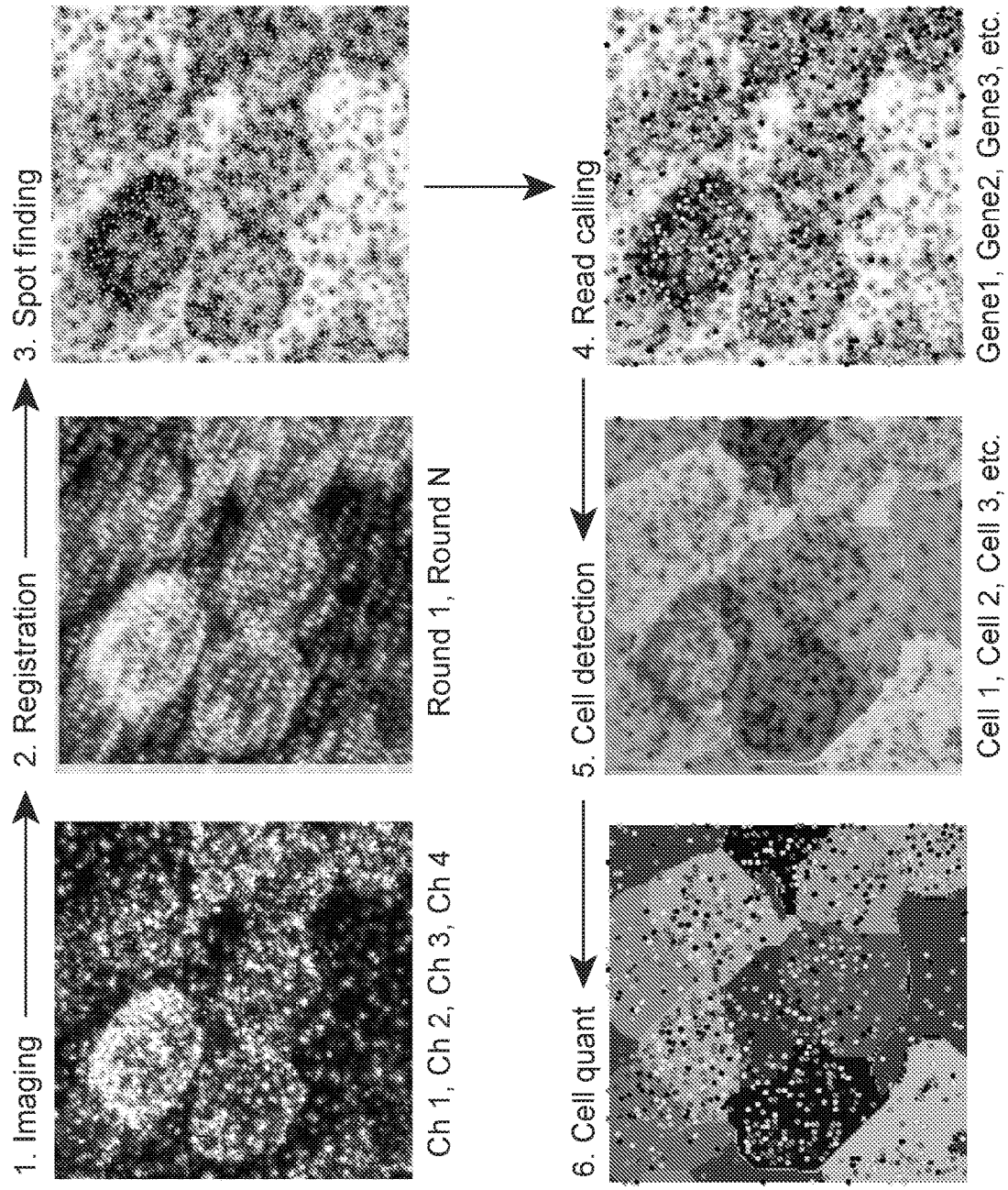

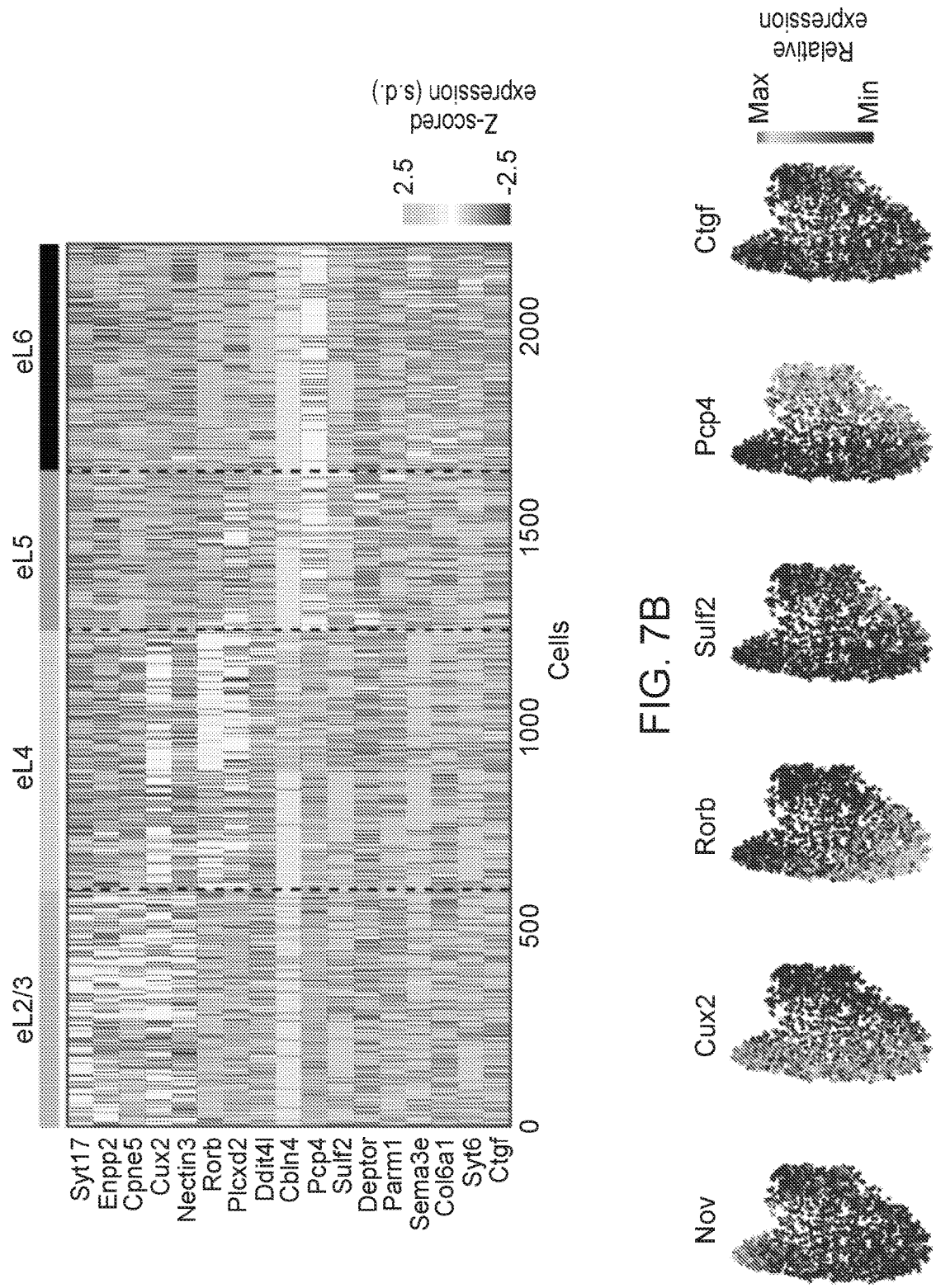

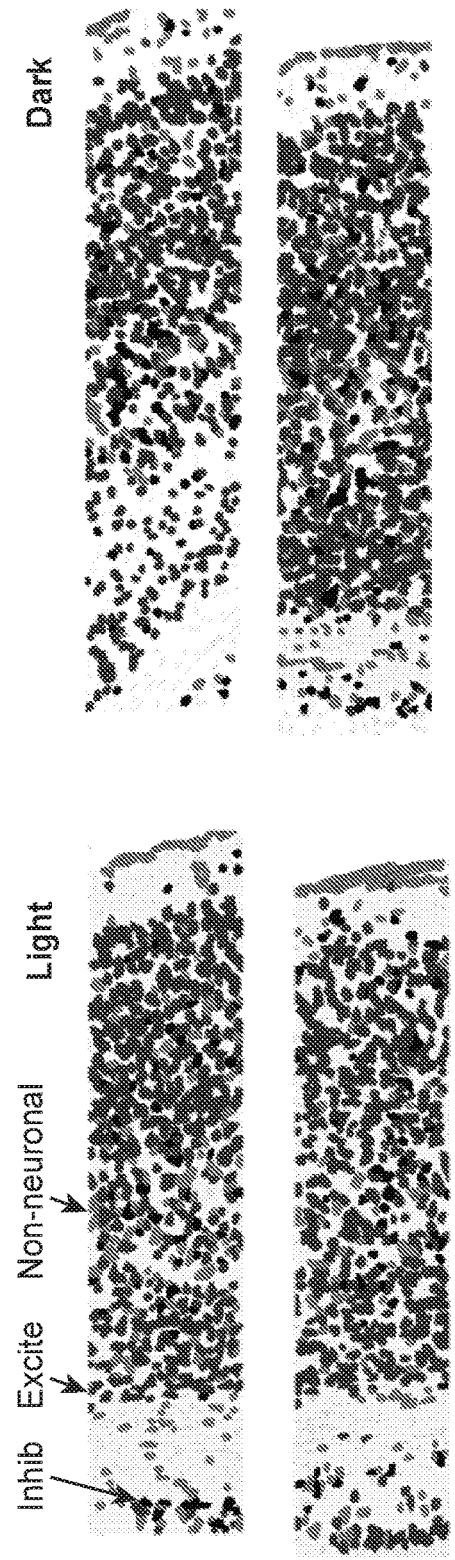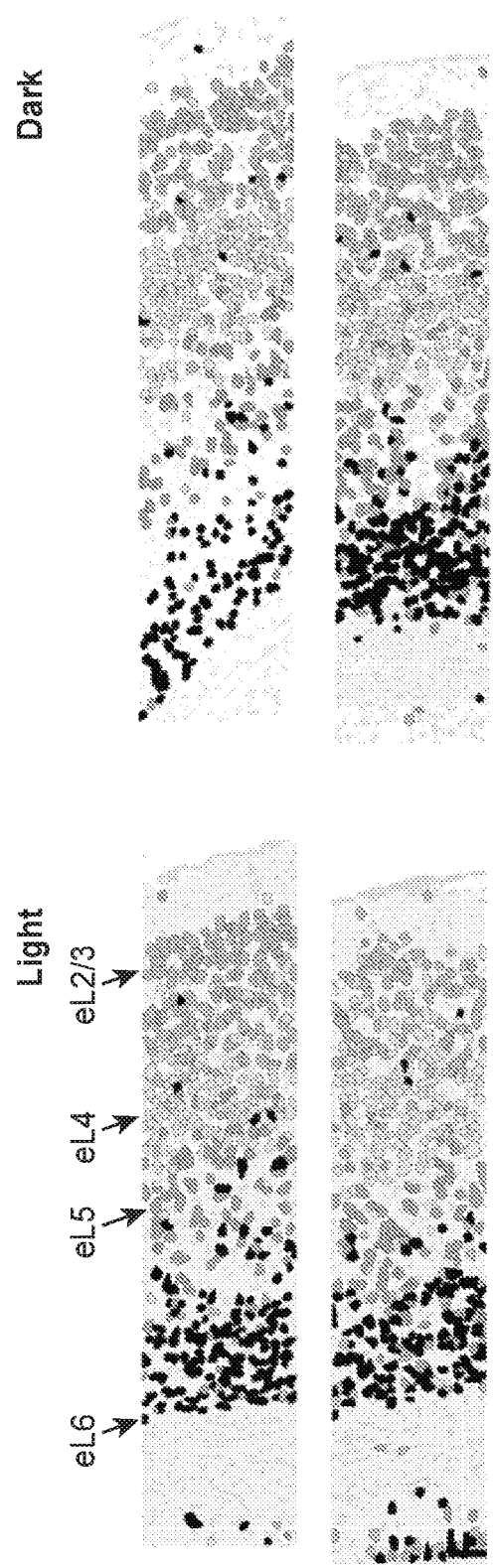

Fos

Egr1

Egr2

STARmap optimized for rapid imaging of large tissue volume

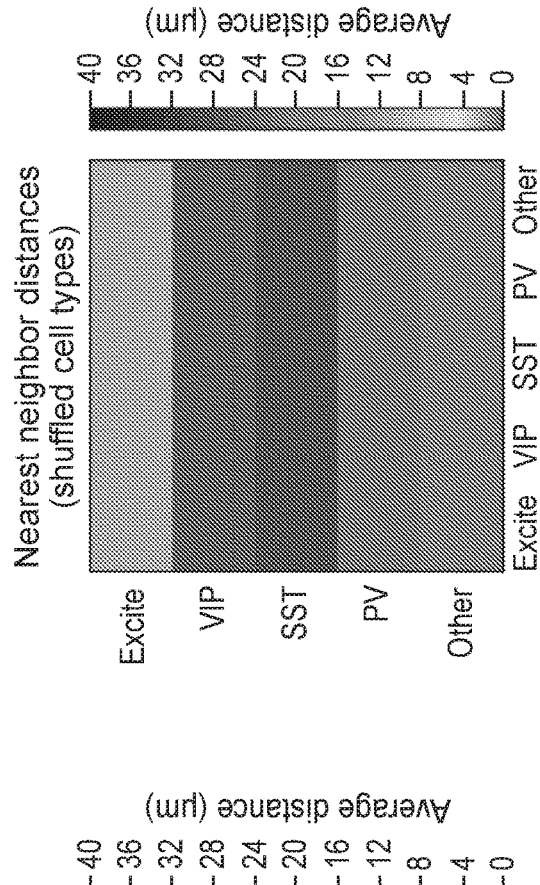
FIG. 13G
FIG. 13H
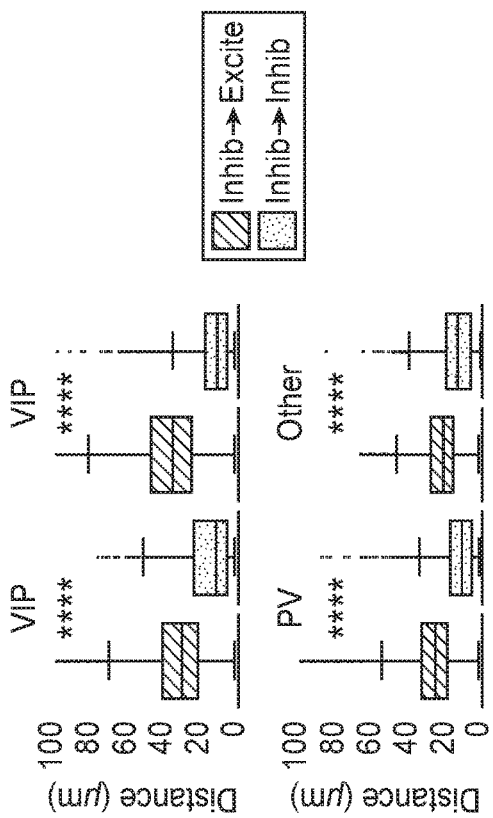
FIG. 13I

Short-range clusters of inhibitory neurons revealed by STARmap

Short-range clusters of Pvalb neurons revealed by transgenic labeling

Scalability of STARmap

| Capacity | Experimentally verified | Theoretical estimation |
|---|---|---|
| Coding limits | ≥ 1,000 codes | ≤ $10^6$ codes (by SEDAL) |
| Physical limits | ≥ 1,000 codes | ≤ $10^6$ amplicons/cell |
| Optical limits | ≥ $1 \times 10^4$ amplicons/cell (cell culture, high-quality through 6 rounds) ≥ 2,600 amplicons/cell (brain tissue, high-quality through 6 rounds) | ≤ $2 \times 10^4$ amplicons/cell |

Inhibitory clusters

Non-neuronal clusters

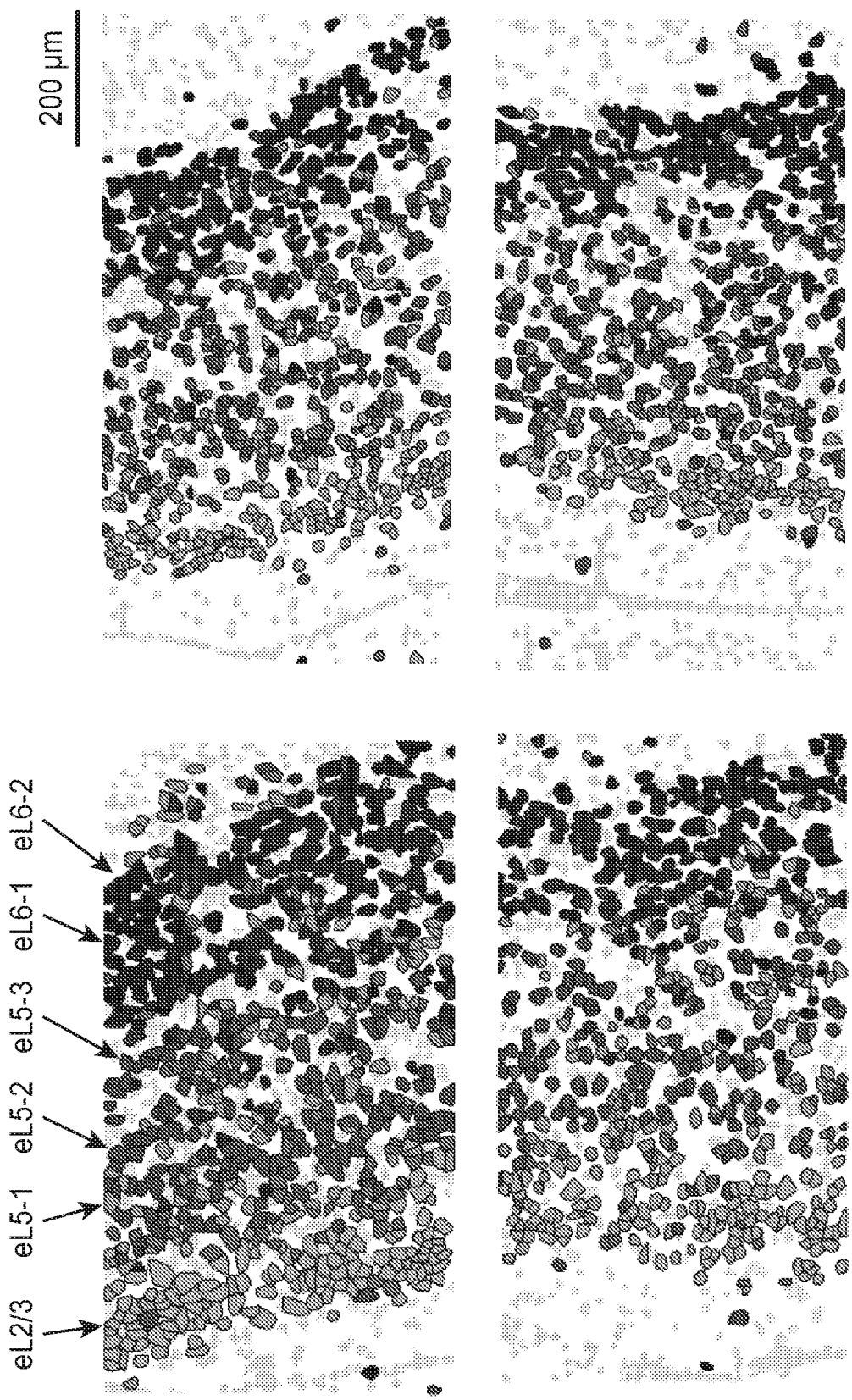

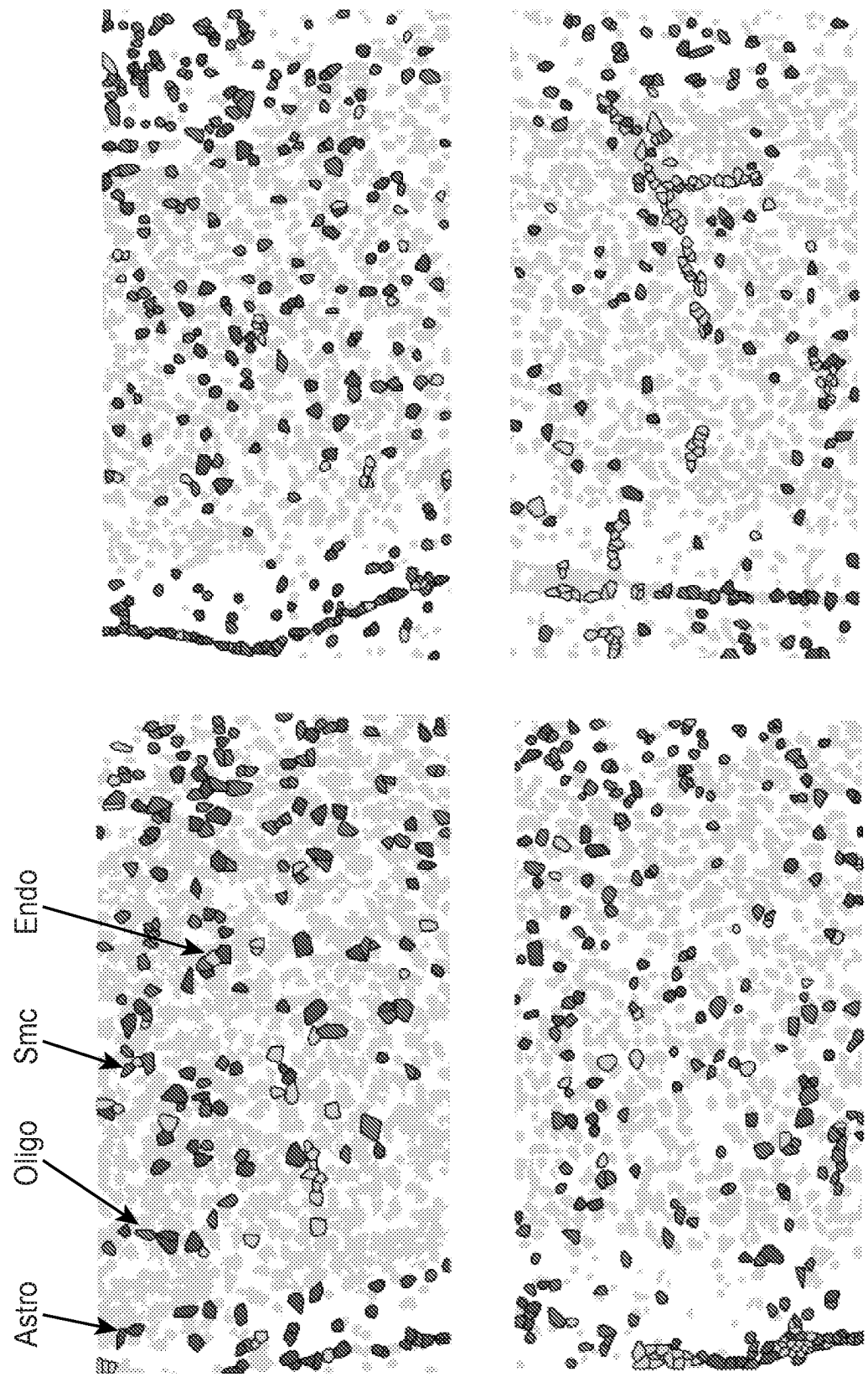

Raw data

Examples of gene markers

*Scna* (neurons)

*Reln* (inhibitory neuron subtype)

*Mt1* (glial cells)

*Sst* (inhibitory neuron subtype)

FIG. 20C Statistics
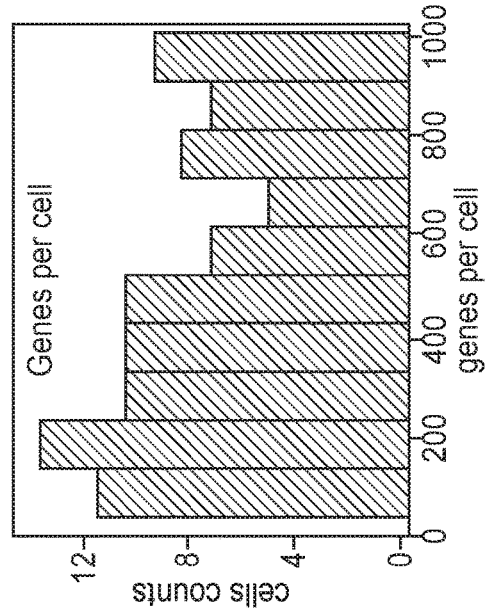
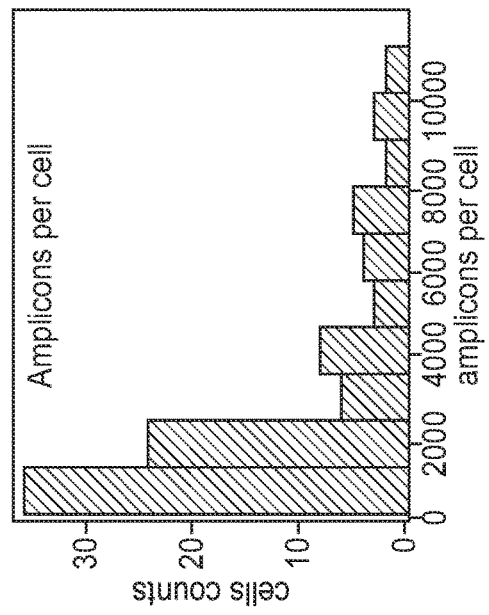
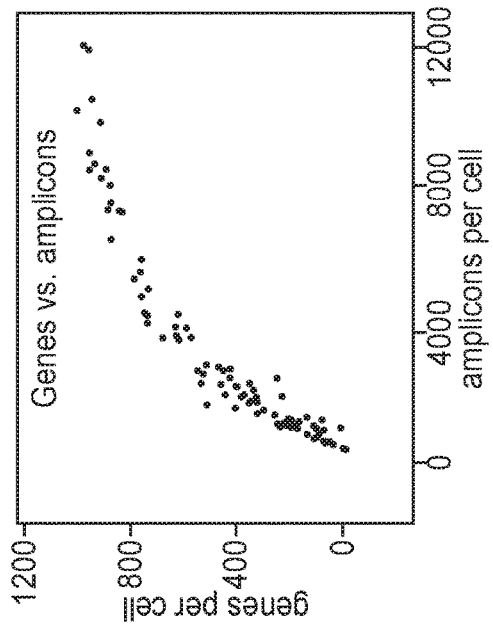

Excitatory clusters

Inhibitory clusters

Non-neuronal clusters

FIG. 21C (Cont.)

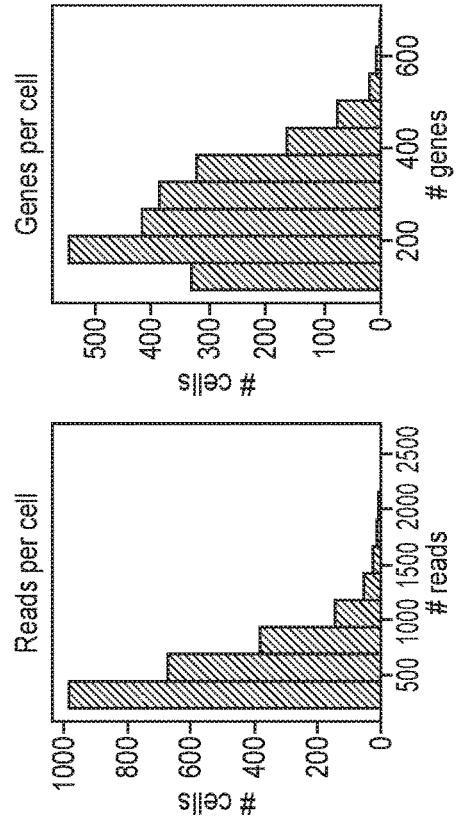
FIG. 22A
FIG. 22B
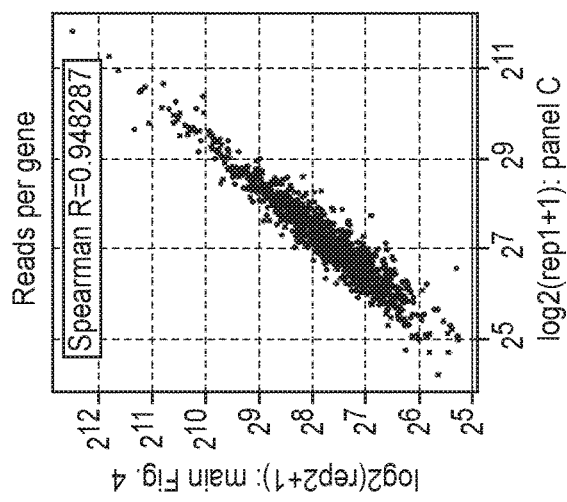
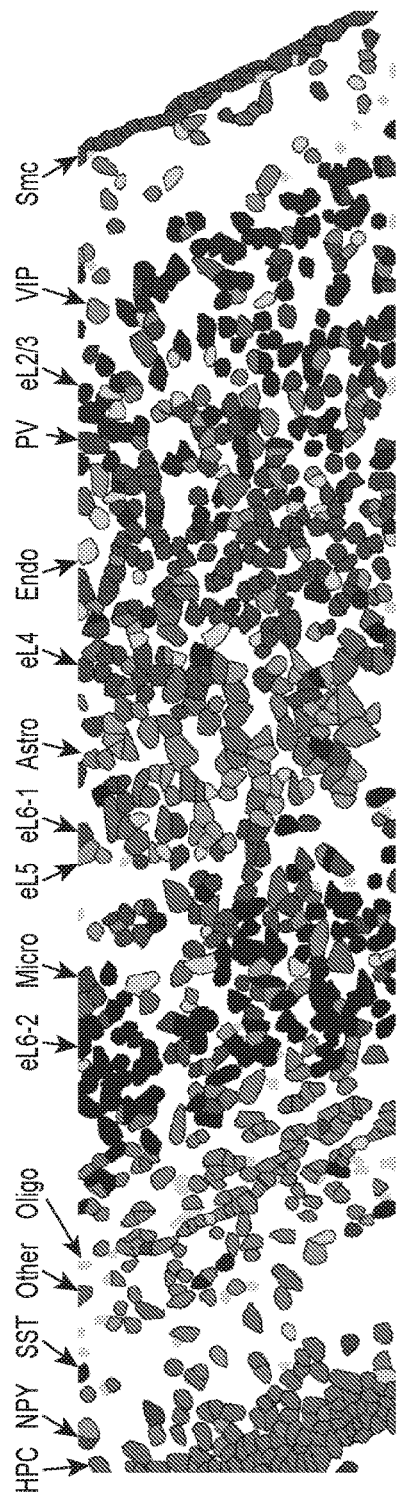
FIG. 22C

FIG. 23B

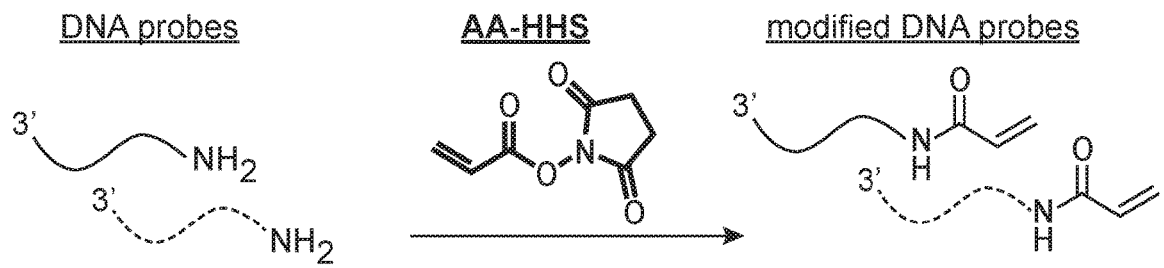

FIG. 23C

Time vs. # genes

| Tissue Type | Genes | Time |
|---|---|---|
| Thin tissue | 4 | 2 days |
| Thin tissue | 160 | 5 days |
| Thin tissue | 1020 | 5 days |
| Thick tissue | 1 | 5 days |
| Thick tissue | 28 | 9 days |

FIG. 23D

Comparisons of STARmap and single-cell PCR/RNA sequencing

| Method | RNA species | Spatial resolution | Quantification | #Cells |
|---|---|---|---|---|
| STARmap thin-tissue | ≥40nt | single-amplicon(250nm) | absolute RNA copies | $10^2 \sim 10^3$ |
| STARmap thick-tissue | ≥40nt | single-cell(1μm) | reletive intensities | $10^4 \sim 10^5$ |
| single-cell PCR | ≥100nt | No | relative amount or absolute RNA copies | $10^1 \sim 10^2$ |
| Single-cell RNA sequencing | poly(A)+ | No or 100μm | absolute RNA copies | $10^2 \sim 10^5$ |

METHOD OF IN SITU GENE SEQUENCING

CROSS-REFERENCE

This application is a national stage application that claims benefit of International Application Ser. No. PCT/US2019/025835, filed Apr. 4, 2019, which claims the benefit of U.S. Provisional Patent Application Ser. No. 62/655,052 filed on Apr. 9, 2018, U.S. Provisional Patent Application Ser. No. 62/687,490 filed on Jun. 20, 2018, and U.S. Provisional Patent Application Ser. No. 62/808,159 filed on Feb. 20, 2019, all of which applications are incorporated herein by reference in their entireties.

INTRODUCTION

In biological tissues, the diversity of function arises from the diversity of form, in part via the complexity of cell-specific gene expression, which defines the unique three-dimensional molecular anatomy and cellular properties of each tissue. In situ transcriptomic tools for the spatial mapping of gene expression with subcellular resolution have emerged that may be applicable to probing these tissue structure-function relationships, including both multiplexed in situ RNA hybridization and in situ RNA sequencing. Current in situ sequencing approaches face the challenge of implementing enzymatic reactions in the dense, complex tissue environment and currently suffer from low efficiency, but the potential value of such in-tissue sequencing could be enormous; in comparison to hybridization-based multiplexing/readout which utilizes multiple polynucleotide probes to encode gene identity, sequencing operates with single-nucleotide resolution, and thus inherently provides vastly greater information. However, current sequencing methods are not yet applicable to 3D volumes of intact tissue, due to fundamental limitations in requisite sensitivity, fidelity, and scalability for throughput in tissues such as the mammalian brain. For example, the mammalian brain consists of an intricate tapestry of cell types, with diversity crucial for function that arises from both differential gene expression and circuit-specific anatomy. Retrieving high-content gene-expression information while retaining 3D positional anatomy at cellular resolution has been difficult, limiting integrative understanding of brain structure and function. The present disclosure addresses the above issues and provides related advantages.

SUMMARY

Provided herein are devices, methods, and systems for in situ gene sequencing of a target nucleic acid in a cell in an intact tissue. Methods of screening a candidate agent to determine whether the candidate agent modulates gene expression of a nucleic acid in a cell in an intact tissue are also provided herein.

The present disclosure provides a method for in situ gene sequencing of a target nucleic acid in a cell in an intact tissue, the method comprising: (a) contacting a fixed and permeabilized intact tissue with at least a pair of oligonucleotide primers under conditions to allow for specific hybridization, wherein the pair of primers comprise a first oligonucleotide and a second oligonucleotide; wherein each of the first oligonucleotide and the second oligonucleotide comprises a first complementarity region, a second complementarity region, and a third complementarity region; wherein the second oligonucleotide further comprises a barcode sequence; wherein the first complementarity region of the first oligonucleotide is complementary to a first portion of the target nucleic acid, wherein the second complementarity region of the first oligonucleotide is complementary to the first complementarity region of the second oligonucleotide, wherein the third complementarity region of the first oligonucleotide is complementary to the third complementarity region of the second oligonucleotide, wherein the second complementary region of the second oligonucleotide is complementary to a second portion of the target nucleic acid, and wherein the first complementarity region of the first oligonucleotide is adjacent to the second complementarity region of the second oligonucleotide; (b) adding ligase to ligate the second oligonucleotide and generate a closed nucleic acid circle; (c) performing rolling circle amplification in the presence of a nucleic acid molecule, wherein the performing comprises using the second oligonucleotide as a template and the first oligonucleotide as a primer for a polymerase to form one or more amplicons; (d) embedding the one or more amplicons in the presence of hydrogel subunits to form one or more hydrogel-embedded amplicons; (e) contacting the one or more hydrogel-embedded amplicons having the barcode sequence with a pair of primers under conditions to allow for ligation, wherein the pair of primers comprise a third oligonucleotide and a fourth oligonucleotide, wherein the ligation only occurs when both the third oligonucleotide and the fourth oligonucleotide ligate to the same amplicon; (f) reiterating step (e); and (g) imaging the one or more hydrogel-embedded amplicons to determine in situ gene sequencing of the target nucleic acid in the cell in the intact tissue. In some cases, the pair of primers are denatured by heating before contacting the sample. In some cases, the cell is present in a population. In some cases, the population of cells includes a plurality of cell types.

The present disclosure also provides a method of screening a candidate agent to determine whether the candidate agent modulates gene expression of a nucleic acid in a cell in an intact tissue, the method comprising: (a) contacting a fixed and permeabilized intact tissue with at least a pair of oligonucleotide primers under conditions to allow for specific hybridization, wherein the pair of primers comprise a first oligonucleotide and a second oligonucleotide; wherein each of the first oligonucleotide and the second oligonucleotide comprises a first complementarity region, a second complementarity region, and a third complementarity region; wherein the second oligonucleotide further comprises a barcode sequence; wherein the first complementarity region of the first oligonucleotide is complementary to a first portion of the target nucleic acid, wherein the second complementarity region of the first oligonucleotide is complementary to the first complementarity region of the second oligonucleotide, wherein the third complementarity region of the first oligonucleotide is complementary to the third complementarity region of the second oligonucleotide, wherein the second complementary region of the second oligonucleotide is complementary to a second portion of the target nucleic acid, and wherein the first complementarity region of the first oligonucleotide is adjacent to the second complementarity region of the second oligonucleotide; (b) adding ligase to ligate the second oligonucleotide and generate a closed nucleic acid circle; (c) performing rolling circle amplification in the presence of a nucleic acid molecule, wherein the performing comprises using the second oligonucleotide as a template and the first oligonucleotide as a primer for a polymerase to form one or more amplicons; (d) embedding the one or more amplicons in the presence of hydrogel subunits to form one or more hydrogel-embedded amplicons; (e) contacting the one or more hydrogel-embedded amplicons having the barcode sequence with a pair of primers under conditions to allow for ligation, wherein the pair of primers comprise a third oligonucleotide and a fourth oligonucleotide, wherein the ligation only occurs when both the third oligonucleotide and the fourth oligonucleotide ligate to the same amplicon; (f) reiterating step (e); (g) imaging the one or more hydrogel-embedded amplicons to determine in situ gene sequencing of the target nucleic acid in the cell in the intact tissue; and (h) detecting the level of gene expression of the target nucleic acid, wherein an alteration in the level of expression of the target nucleic acid in the presence of the at least one candidate agent relative to the level of expression of the target nucleic acid in the absence of the at least one candidate agent indicates that the at least one candidate agent modulates gene expression of the nucleic acid in the cell in the intact tissue. In some cases, the pair of primers are denatured by heating before contacting the sample. In some cases, the cell is present in a population of cells. In some cases, the population of cells includes a plurality of cell types.

Also provided is a device used according to the methods described herein. In some embodiments, provided is a fluidics system for automation of the methods described herein, allowing for continual operation. In some embodiments, the system includes a fluidics device, and a processor configured to perform the methods described herein.

BRIEF DESCRIPTION OF THE DRAWINGS

FIG. 1A-1E depict a schematic of a Spatially-resolved Transcript Amplicon Readout Mapping (STARmap) method as described herein including in situ RNA sequencing for spatial transcriptomics within the 3D tissue environment.

FIG. 3A-3H depict hydrogel-tissue chemistry (HTC) for background reduction and amplicon immobilization in STARmap.

FIG. 4A-4L depict aspects of Sequencing by Dynamic Annealing and Ligation (SEDAL), the low-background error-correcting in situ sequencing component of STARmap.

FIG. 6A-6C depict the data processing pipeline for STARmap.

FIG. 7A-7D depict gene expression information for STARmapping of inhibitory and excitatory subclusters.

FIG. 9A-9G depict the lack of batch effects with reproducibility of cell clustering using the methods described herein.

FIG. 13A-13I depict the three-dimensional architecture of cell types in visual cortex volumes.

FIG. 19A-19C depict the reproducibility of cell clusters and spatial organization of mPFC using the methods described herein.

FIG. 20A-20C depict the analysis of 1020 genes in mouse hippocampal cell culture in 6-round sequencin using the methods described herein.

FIG. 22A-22D depict the reproducibility and cross-method comparison of measurements of 1020 genes in mouse primary visual cortex using the methods described herein.

FIG. 23A-23D depict experimental flowcharts and cost estimates of STARmap for thin and thick tissue sections.

DETAILED DESCRIPTION

Provided herein are devices, methods, and systems for in situ gene sequencing of a target nucleic acid in a cell in an intact tissue. Methods of screening a candidate agent to determine whether the candidate agent modulates gene expression of a nucleic acid in a cell in an intact tissue are also provided herein.

Figure 1B:
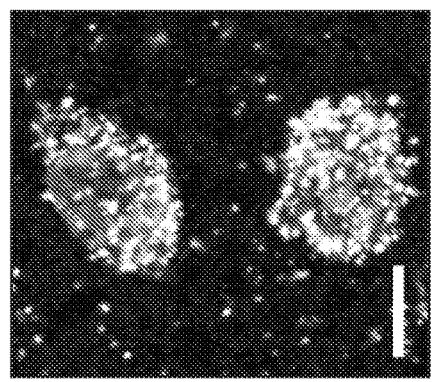

In some embodiments, the disclosed methods for 3D intact-tissue RNA sequencing in brains and other organs, termed Spatially-resolved Transcript Amplicon Readout Mapping (STARmap), include integrating an improved sequencing-by-ligation process, specific signal amplification, and hydrogel-tissue chemistry (FIG. 1A). In certain aspects, STARmap enables cellular-resolution expression mapping via a sequencing of 160 distinct genes in all cells within mouse visual cortex slices. In certain aspects, STARmap enables the identification of diverse anatomically- and molecularly-resolved cell types within cortical layers, including interneuron and glial subtypes, and the quantified expression of activity-regulated genes as a function of visual stimulation, spatial position, and molecularly-defined cell typology. In certain aspects, STARmap enables the quantification of more than 30,000 cells in cubic millimeter-scale volumes, revealing a gradient-distribution of excitatory neuron subtypes contrasting with 3D clustering patterns of inhibitory neurons.

In some embodiments, in situ synthesized hydrogels are integrated with intracellularly-delivered interfaces that couple to native biomolecules, which transforms the tissue, from within its constituent cells, into a new state suitable for high-resolution volumetric imaging and analysis compatible with many kinds of molecular phenotyping for proteins, nucleic acids, and other targets. For example, synthetic hydrogels have been used to accommodate enzymatic reactions that include DNA sequencing and are known in the art, including, but not limited to technologies disclosed in WO2014/025392, the reference of which is incorporated herein by reference. In some embodiments, biological tissue may be converted into a hydrogel-embedded form compatible with creation, retention, and functional presentation of RNA-derived complementary DNA (cDNA). In such aspects, 3D in situ sequencing may be performed within such a tissue-hydrogel formulation, thus leveraging the crucial attendant properties of optical transparency, reduced background, elevated diffusion rate, and greater mechanical stability.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term "polypeptide" includes fusion proteins, including, but not limited to, fusion proteins with a heterologous amino acid sequence, fusions with heterologous and homologous leader sequences, with or without N-terminal methionine residues; immunologically tagged proteins; and the like. The term "polypeptide" includes polypeptides including one or more of a fatty acid moiety, a lipid moiety, a sugar moiety, and a carbohydrate moiety. The term "polypeptides" includes post-translationally modified polypeptides.

As used herein, the term "target nucleic acid" is any polynucleotide nucleic acid molecule (e.g., DNA molecule; RNA molecule, modified nucleic acid, etc.) present in a single cell. In some embodiments, the target nucleic acid is a coding RNA (e.g., mRNA). In some embodiments, the target nucleic acid is a non-coding RNA (e.g., tRNA, rRNA, microRNA (miRNA), mature miRNA, immature miRNA; etc). In some embodiments, the target nucleic acid is a splice variant of an RNA molecule (e.g., mRNA, pre-mRNA, etc.) in the context of a cell. A suitable target nucleic acid can therefore be an unspliced RNA (e.g., pre-mRNA, mRNA), a partially spliced RNA, or a fully spliced RNA, etc. Target nucleic acids of interest may be variably expressed, i.e. have a differing abundance, within a cell population, wherein the methods of the invention allow profiling and comparison of the expression levels of nucleic acids, including without limitation RNA transcripts, in individual cells. A target nucleic acid can also be a DNA molecule, e.g. a denatured genomic, viral, plasmid, etc. For example the methods can be used to detect copy number variants, e.g. in a cancer cell population in which a target nucleic acid is present at different abundance in the genome of cells in the population; a virus-infected cells to determine the virus load and kinetics, and the like.

The terms "oligonucleotide," "polynucleotide," and "nucleic acid molecule", used interchangeably herein, refer to polymeric forms of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer including purine and pyrimidine bases or other natural, chemically or biochemically modified, non-natural, or derivatized nucleotide bases. The backbone of the polynucleotide can include sugars and phosphate groups (as may typically be found in RNA or DNA), or modified or substituted sugar or phosphate groups. Alternatively, the backbone of the polynucleotide can include a polymer of synthetic subunits such as phosphoramidites, and/or phosphorothioates, and thus can be an oligodeoxynucleoside phosphoramidate or a mixed phosphoramidate-phosphodiester oligomer. Peyrottes et al. (1996) Nucl. Acids Res. 24:1841-1848; Chaturvedi et al. (1996) Nucl. Acids Res. 24:2318-2323. The polynucleotide may include one or more L-nucleosides. A polynucleotide may include modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be modified to include N3'-P5' (NP) phosphoramidate, morpholino phosphorociamidate (MF), lockaed nucleic acid (LNA), 2'-O-methoxyethyl (MOE), or 2'-fluoro, arabino-nucleic acid (FANA), which can enhance the reistance of the polynucleotide to nuclease degradation (see, e.g., Faria et al. (2001) Nature Biotechnol. 19:40-44; Toulme (2001) Nature Biotechnol. 19:17-18). A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Immunomodulatory nucleic acid molecules can be provided in various formulations, e.g., in association with liposomes, microencapsulated, etc., as described in more detail herein. A polynucleotide used in amplification is generally single-stranded for maximum efficiency in amplification, but may alternatively be double-stranded. If double-stranded, the polynucleotide can first be treated to separate its strands before being used to prepare extension products. This denaturation step is typically affected by heat, but may alternatively be carried out using alkali, followed by neutralization.

By "subject" or "individual" or "patient" is meant any subject for whom or which therapy is desired. Human subjects are of particular interest. Other subjects may include non-human primates, cattle, sheep, goats, dogs, cats, birds (e.g., chickens or other poultry), guinea pigs, rabbits, rats, mice, horses, and so on. Of particular interest are subjects having or susceptible to brain damage.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the oligonucleotide" includes reference to one or more oligonucleotides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods

The methods disclosed herein include an image-based in situ nucleic acid (DNA and/or RNA) sequencing technology by an improved sequencing-by-ligation process, specific signal amplification, hydrogel-tis sue chemistry to turn biological tissue into a transparent sequencing chip, and associated data analysis pipelines, collectively termed Spatially-resolved Transcript Amplicon Readout Mapping (STARmap), to spatially-resolve highly-multiplexed gene detection at a subcellular and cellular level. In some embodiments, STARmap defines a platform for 3D in situ transcriptomics, enabled by improved cDNA library preparation, sequencing, and hydrogel-tissue chemistry.

As summarized above, the methods disclosed herein include a method for in situ gene sequencing of a target nucleic acid in a cell in an intact tissue, the method including: (a) contacting a fixed and permeabilized intact tissue with at least a pair of oligonucleotide primers under conditions to allow for specific hybridization, wherein the pair of primers include a first oligonucleotide and a second oligonucleotide; wherein each of the first oligonucleotide and the second oligonucleotide includes a first complementarity region, a second complementarity region, and a third complementarity region; wherein the second oligonucleotide further includes a barcode sequence; wherein the first complementarity region of the first oligonucleotide is complementary to a first portion of the target nucleic acid, wherein the second complementarity region of the first oligonucleotide is complementary to the first complementarity region of the second oligonucleotide, wherein the third complementarity region of the first oligonucleotide is complementary to the third complementarity region of the second oligonucleotide, wherein the second complementary region of the second oligonucleotide is complementary to a second portion of the target nucleic acid, and wherein the first complementarity region of the first oligonucleotide is adjacent to the second complementarity region of the second oligonucleotide; (b) adding ligase to ligate the second oligonucleotide and generate a closed nucleic acid circle; (c) performing rolling circle amplification in the presence of a nucleic acid molecule, wherein the performing includes using the second oligonucleotide as a template and the first oligonucleotide as a primer for a polymerase to form one or more amplicons; (d) embedding the one or more amplicons in the presence of hydrogel subunits to form one or more hydrogel-embedded amplicons; (e) contacting the one or more hydrogel-embedded amplicons having the barcode sequence with a pair of primers under conditions to allow for ligation, wherein the pair of primers include a third oligonucleotide and a fourth oligonucleotide, wherein the ligation only occurs when both the third oligonucleotide and the fourth oligonucleotide ligate to the same amplicon; (f) reiterating step (e); and (g) imaging the one or more hydrogel-embedded amplicons to determine in situ gene sequencing of the target nucleic acid in the cell in the intact tissue.

The methods disclosed herein also provide for a method of screening a candidate agent to determine whether the candidate agent modulates gene expression of a nucleic acid in a cell in an intact tissue, the method including: (a) contacting a fixed and permeabilized intact tissue with at least a pair of oligonucleotide primers under conditions to allow for specific hybridization, wherein the pair of primers include a first oligonucleotide and a second oligonucleotide; wherein each of the first oligonucleotide and the second oligonucleotide includes a first complementarity region, a second complementarity region, and a third complementarity region; wherein the second oligonucleotide further includes a barcode sequence; wherein the first complementarity region of the first oligonucleotide is complementary to a first portion of the target nucleic acid, wherein the second complementarity region of the first oligonucleotide is complementary to the first complementarity region of the second oligonucleotide, wherein the third complementarity region of the first oligonucleotide is complementary to the third complementarity region of the second oligonucleotide, wherein the second complementary region of the second oligonucleotide is complementary to a second portion of the target nucleic acid, and wherein the first complementarity region of the first oligonucleotide is adjacent to the second complementarity region of the second oligonucleotide; (b) adding ligase to ligate the second oligonucleotide and generate a closed nucleic acid circle; (c) performing rolling circle amplification in the presence of a nucleic acid molecule, wherein the performing includes using the second oligonucleotide as a template and the first oligonucleotide as a primer for a polymerase to form one or more amplicons; (d) embedding the one or more amplicons in the presence of hydrogel subunits to form one or more hydrogel-embedded amplicons; (e) contacting the one or more hydrogel-embedded amplicons having the barcode sequence with a pair of primers under conditions to allow for ligation, wherein the pair of primers include a third oligonucleotide and a fourth oligonucleotide, wherein the ligation only occurs when both the third oligonucleotide and the fourth oligonucleotide ligate to the same amplicon; (f) reiterating step (e); (g) imaging the one or more hydrogel-embedded amplicons to determine in situ gene sequencing of the target nucleic acid in the cell in the intact tissue; and (h) detecting the level of gene expression of the target nucleic acid, wherein an alteration in the level of expression of the target nucleic acid in the presence of the at least one candidate agent relative to the level of expression of the target nucleic acid in the absence of the at least one candidate agent indicates that the at least one candidate agent modulates gene expression of the nucleic acid in the cell in the intact tissue.

In certain aspects, the methods disclosed herein provide for a faster processing time, higher multiplexity (up to 1000 genes), higher efficiency, higher sensitivity, lower error rate, and more spatially resolved cell types, as compared to existing gene expression analysis tools. In such aspects, the improved hydrogel-tissue chemistry method transforms biological tissue into nucleic acids imprinted with hydrogel compatible with in situ sequencing, an improved sequencing-by-ligation process (SEDAL) for in situ sequencing with error reduction. In some other aspects, the methods disclosed herein include spatially sequencing (e.g. reagents, chips or services) for biomedical research and clinical diagnostics (e.g. cancer, bacterial infection, viral infection, etc.) with single-cell and/or single-molecule sensitivity.

Specific Amplification of Nucleic Acids via Intramolecular Ligation (SNAIL)

In some embodiments, one component of STARmap includes an efficient approach for generating cDNA libraries from cellular RNAs in situ, which may be referred to as SNAIL, for Specific Amplification of Nucleic Acids via Intramolecular Ligation. In certain embodiments, the methods of the invention include contacting a fixed and permeabilized intact tissue with at least a pair of oligonucleotide primers under conditions to allow for specific hybridization, wherein the pair of primers includes a first oligonucleotide and a second oligonucleotide.

More generally, the nucleic acid present in a cell of interest in a tissue serves as a scaffold for an assembly of a complex that includes a pair of primers, referred to herein as a first oligonucleotide and a second oligonucleotide. In some embodiments, the contacting the fixed and permeabilized intact tissue includes hybridizing the pair of primers to the same target nucleic acid. In some embodiments, the target nucleic acid is RNA. In such embodiments, the target nucleic acid may be mRNA. In other embodiments, the target nucleic acid is DNA.

As used herein, the terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis. It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

SNAIL Oligonucleotide Primers

In the method of the invention, the SNAIL oligonucleotide primers include at least a first oligonucleotide and a second oligonucleotide; wherein each of the first oligonucleotide and the second oligonucleotide includes a first complementarity region, a second complementarity region, and a third complementarity region; wherein the second oligonucleotide further includes a barcode sequence; wherein the first complementarity region of the first oligonucleotide is complementary to a first portion of the target nucleic acid, wherein the second complementarity region of the first oligonucleotide is complementary to the first complementarity region of the second oligonucleotide, wherein the third complementarity region of the first oligonucleotide is complementary to the third complementarity region of the second oligonucleotide, wherein the second complementary region of the second oligonucleotide is complementary to a second portion of the target nucleic acid, and wherein the first complementarity region of the first oligonucleotide is adjacent to the second complementarity region of the second oligonucleotide. In an alternative embodiment, the second oligonucleotide is a closed circular molecule, and a ligation step is omitted.

The present disclosure provides methods where the contacting a fixed and permealized tissue includes hybridizing a plurality of oligonucleotide primers having specificity for different target nucleic acids. In some embodiments, the methods include a plurality of first oligonucleotides, including, but not limited to, 5 or more first oligonucleotides, e.g., 8 or more, 10 or more, 12 or more, 15 or more, 18 or more, 20 or more, 25 or more, 30 or more, 35 or more that hybridize to target nucleotide sequences. In some embodiments, a method of the present disclosure includes a plurality of first oligonucleotides, including, but not limited to, 15 or more first oligonucleotides, e.g., 20 or more, 30 or more, 40 or more, 50 or more, 60 or more, 70 or more, and up to 80 different first oligonucleotides that hybridize to 15 or more, e.g., 20 or more, 30 or more, 40 or more, 50 or more, 60 or more, 70 or more, and up to 80 different target nucleotide sequences. In some embodiments, the methods include a plurality of second oligonucleotides, including, but not limited to, 5 or more second oligonucleotides, e.g., 8 or more, 10 or more, 12 or more, 15 or more, 18 or more, 20 or more, 25 or more, 30 or more, 35 or more. In some embodiments, a method of the present disclosure includes a plurality of second oligonucleotides including, but not limited to, 15 or more second oligonucleotides, e.g., 20 or more, 30 or more, 40 or more, 50 or more, 60 or more, 70 or more, and up to 80 different first oligonucleotides that hybridize to 15 or more, e.g., 20 or more, 30 or more, 40 or more, 50 or more, 60 or more, 70 or more, and up to 80 different target nucleotide sequences. A plurality of oligonucleotide pairs can be used in a reaction, where one or more pairs specifically bind to each target nucleic acid. For example, two primer pairs can be used for one target nucleic acid in order to improve sensitivity and reduce variability. It is also of interest to detect a plurality of different target nucleic acids in a cell, e.g. detecting up to 2, up to 3, up to 4, up to 5, up to 6, up to 7, up to 8, up to 9, up to 10, up to 12, up to 15, up to 18, up to 20, up to 25, up to 30, up to 40 or more distinct target nucleic acids. The primers are typically denatured prior to use, typically by heating to a temperature of at least about 50° C., at least about 60° C., at least about 70° C., at least about 80° C., and up to about 99° C., up to about 95° C., up to about 90° C.

In some embodiments, the primers are denatured by heating before contacting the sample. In certain aspects, the melting temperature ($T_m$) of oligonucleotides is selected to minimize ligation in solution. The "melting temperature" or "Tm" of a nucleic acid is defined as the temperature at which half of the helical structure of the nucleic acid is lost due to heating or other dissociation of the hydrogen bonding between base pairs, for example, by acid or alkali treatment, or the like. The $T_m$ of a nucleic acid molecule depends on its length and on its base composition. Nucleic acid molecules rich in GC base pairs have a higher $T_m$ than those having an abundance of AT base pairs. Separated complementary strands of nucleic acid spontaneously reassociate or anneal to form duplex nucleic acid when the temperature is lowered below the $T_m$. The highest rate of nucleic acid hybridization occurs approximately 25 degrees C. below the $T_m$. The $T_m$ may be estimated using the following relationship: $T_m$=69.3+0.41(GC) % (Marmur et al. (1962) J. Mol. Biol. 5:109-118).

In certain embodiments, the plurality of second oligonucleotides includes a padlock probe. In some embodiments, the probe includes a detectable label that can be measured and quantitated. The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradium esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

In some embodiments, the one or more first oligonucleotides and second oligonucleotides bind to a different region of the target nucleic acid, or target site. In a pair, each target site is different, and the target sites are adjacent sites on the target nucleic acid, e.g. usually not more than 15 nucleotides distant, e.g. not more than 10, 8, 6, 4, or 2 nucleotides distant from the other site, and may be contiguous sites. Target sites are typically present on the same strand of the target nucleic acid in the same orientation. Target sites are also selected to provide a unique binding site, relative to other nucleic acids present in the cell. Each target site is generally from about 19 to about 25 nucleotides in length, e.g. from about 19 to 23 nucleotides, from about 19 to 21 nucleotides, or from about 19 to 20 nucleotides. The pair of first and second oligonucleotides are selected such that each oligonucleotide in the pair has a similar melting temperature for binding to its cognate target site, e.g. the $T_m$ may be from about 50° C., from about 52° C., from about 55° C., from about 58°, from about 62° C., from about 65° C., from about 70° C., or from about 72° C. The GC content of the target site is generally selected to be no more than about 20%, no more than about 30%, no more than about 40%, no more than about 50%, no more than about 60%, no more than about 70%.

In some embodiments, the first oligonucleotide includes a first, second, and third complementarity region. The target site of the first oligonucleotide may refer to the first complementarity region. As summarized above, the first complementarity region of the first oligonucleotide may have a length of 19-25 nucleotides. In certain aspects, the second complementarity region of the first oligonucleotide has a length of 3-10 nucleotides, including, e.g., 4-8 nucleotides or 4-7 nucleotides. In some aspects, the second complementarity region of the first oligonucleotide has a length of 6 nucleotides. In some embodiments, the third complementarity region of the first oligonucleotide likewise has a length of 6 nucleotides. In such embodiments, the third complementarity region of the first oligonucleotide has a length of 3-10 nucleotides, including, e.g., 4-8 nucleotides or 4-7 nucleotides.

In some embodiments, second first oligonucleotide includes a first, second, and third complementarity region. The target site of the second oligonucleotide may refer to the second complementarity region. As summarized above, the second complementarity region of the second oligonucleotide may have a length of 19-25 nucleotides. In certain aspects, the first complementarity region of the first oligonucleotide has a length of 3-10 nucleotides, including, e.g., 4-8 nucleotides or 4-7 nucleotides. In some aspects, the first complementarity region of the first oligonucleotide has a length of 6 nucleotides. In some aspects, the first complementarity region of the second oligonucleotide includes the 5' end of the second oligonucleotide. In some embodiments, the third complementarity region of the second oligonucleotide likewise has a length of 6 nucleotides. In such embodiments, the third complementarity region of the second oligonucleotide has a length of 3-10 nucleotides, including, e.g., 4-8 nucleotides or 4-7 nucleotides. In further embodiments, the third complementarity region of the second oligonucleotide includes the 3' end of the second oligonucleotide. In some embodiments, the first complementarity region of the second oligonucleotide is adjacent to the third complementarity region of the second oligonucleotide.

In some aspects, the second oligonucleotide includes a barcode sequence, wherein the barcode sequence of the second oligonucleotide provides barcoding information for identification of the target nucleic acid. The term "barcode" refers to a nucleic acid sequence that is used to identify a single cell or a subpopulation of cells. Barcode sequences can be linked to a target nucleic acid of interest during amplification and used to trace back the amplicon to the cell from which the target nucleic acid originated. A barcode sequence can be added to a target nucleic acid of interest during amplification by carrying out amplification with an oligonucleotide that contains a region including the barcode sequence and a region that is complementary to the target nucleic acid such that the barcode sequence is incorporated into the final amplified target nucleic acid product (i.e., amplicon).

Tissue

As described herein, the methods disclosed include in situ sequencing technology of an intact tissue by at least contact a fixed and permeabilized intact tissue with at least a pair of oligonucleotide primers under conditions to allow for specific hybridization. Tissue specimens suitable for use with the methods described herein generally include any type of tissue specimens collected from living or dead subjects, such as, e.g., biopsy specimens and autopsy specimens, of which include, but are not limited to, epithelium, muscle, connective, and nervous tissue. Tissue specimens may be collected and processed using the methods described herein and subjected to microscopic analysis immediately following processing, or may be preserved and subjected to microscopic analysis at a future time, e.g., after storage for an extended period of time. In some embodiments, the methods described herein may be used to preserve tissue specimens in a stable, accessible and fully intact form for future analysis. In some embodiments, the methods described herein may be used to analyze a previously-preserved or stored tissue specimen. In some embodiments, the intact tissue includes brain tissue such as visual cortex slices. In some embodiments, the intact tissue is a thin slice with a thickness of 5-20 µm, including, but not limited to, e.g., 5-18 µm, 5-15 µm, or 5-10 µm. In other embodiments, the intact tissue is a thick slice with a thickness of 50-200 µm, including, but not limited to, e.g., 50-150 µm, 50-100 µm, or 50-80 µm.

Aspects of the invention include fixing intact tissue. The term "fixing" or "fixation" as used herein is the process of preserving biological material (e.g., tissues, cells, organelles, molecules, etc.) from decay and/or degradation. Fixation may be accomplished using any convenient protocol. Fixation can include contacting the sample with a fixation reagent (i.e., a reagent that contains at least one fixative). Samples can be contacted by a fixation reagent for a wide range of times, which can depend on the temperature, the nature of the sample, and on the fixative(s). For example, a sample can be contacted by a fixation reagent for 24 or less hours, 18 or less hours, 12 or less hours, 8 or less hours, 6 or less hours, 4 or less hours, 2 or less hours, 60 or less minutes, 45 or less minutes, 30 or less minutes, 25 or less minutes, 20 or less minutes, 15 or less minutes, 10 or less minutes, 5 or less minutes, or 2 or less minutes.

A sample can be contacted by a fixation reagent for a period of time in a range of from 5 minutes to 24 hours, e.g., from 10 minutes to 20 hours, from 10 minutes to 18 hours, from 10 minutes to 12 hours, from 10 minutes to 8 hours, from 10 minutes to 6 hours, from 10 minutes to 4 hours, from 10 minutes to 2 hours, from 15 minutes to 20 hours, from 15 minutes to 18 hours, from 15 minutes to 12 hours, from 15 minutes to 8 hours, from 15 minutes to 6 hours, from 15 minutes to 4 hours, from 15 minutes to 2 hours, from 15 minutes to 1.5 hours, from 15 minutes to 1 hour, from 10 minutes to 30 minutes, from 15 minutes to 30 minutes, from 30 minutes to 2 hours, from 45 minutes to 1.5 hours, or from 55 minutes to 70 minutes.

A sample can be contacted by a fixation reagent at various temperatures, depending on the protocol and the reagent used. For example, in some instances a sample can be contacted by a fixation reagent at a temperature ranging from −22° C. to 55° C., where specific ranges of interest include, but are not limited to 50 to 54° C., 40 to 44° C., 35 to 39° C., 28 to 32° C., 20 to 26° C., 0 to 6° C., and −18 to −22° C. In some instances a sample can be contacted by a fixation reagent at a temperature of −20° C., 4° C., room temperature (22-25° C.), 30° C., 37° C., 42° C., or 52° C.

Any convenient fixation reagent can be used. Common fixation reagents include cros slinking fixatives, precipitating fixatives, oxidizing fixatives, mercurials, and the like. Crosslinking fixatives chemically join two or more molecules by a covalent bond and a wide range of cross-linking reagents can be used. Examples of suitable cross-liking fixatives include but are not limited to aldehydes (e.g., formaldehyde, also commonly referred to as "paraformaldehyde" and "formalin"; glutaraldehyde; etc.), imidoesters, NHS (N-Hydroxysuccinimide) esters, and the like. Examples of suitable precipitating fixatives include but are not limited to alcohols (e.g., methanol, ethanol, etc.), acetone, acetic acid, etc. In some embodiments, the fixative is formaldehyde (i.e., paraformaldehyde or formalin). A suitable final concentration of formaldehyde in a fixation reagent is 0.1 to 10%, 1-8%, 1-4%, 1-2%, 3-5%, or 3.5-4.5%, including about 1.6% for 10 minutes. In some embodiments the sample is fixed in a final concentration of 4% formaldehyde (as diluted from a more concentrated stock solution, e.g., 38%, 37%, 36%, 20%, 18%, 16%, 14%, 10%, 8%, 6%, etc.). In some embodiments the sample is fixed in a final concentration of 10% formaldehyde. In some embodiments the sample is fixed in a final concentration of 1% formaldehyde. In some embodiments, the fixative is glutaraldehyde. A suitable concentration of glutaraldehyde in a fixation reagent is 0.1 to 1%. A fixation reagent can contain more than one fixative in any combination. For example, in some embodiments the sample is contacted with a fixation reagent containing both formaldehyde and glutaraldehyde.

The terms "permeabilization" or "permeabilize" as used herein refer to the process of rendering the cells (cell membranes etc.) of a sample permeable to experimental reagents such as nucleic acid probes, antibodies, chemical substrates, etc. Any convenient method and/or reagent for permeabilization can be used. Suitable permeabilization reagents include detergents (e.g., Saponin, Triton X-100, Tween-20, etc.), organic fixatives (e.g., acetone, methanol, ethanol, etc.), enzymes, etc. Detergents can be used at a range of concentrations. For example, 0.001%-1% detergent, 0.05%-0.5% detergent, or 0.1%-0.3% detergent can be used for permeabilization (e.g., 0.1% Saponin, 0.2% tween-20, 0.1-0.3% triton X-100, etc.). In some embodiments methanol on ice for at least 10 minutes is used to permeabilize.

In some embodiments, the same solution can be used as the fixation reagent and the permeabilization reagent. For example, in some embodiments, the fixation reagent contains 0.1%-10% formaldehyde and 0.001%-1% saponin. In some embodiments, the fixation reagent contains 1% formaldehyde and 0.3% saponin.

A sample can be contacted by a permeabilization reagent for a wide range of times, which can depend on the temperature, the nature of the sample, and on the permeabilization reagent(s). For example, a sample can be contacted by a permeabilization reagent for 24 or more hours, 24 or less hours, 18 or less hours, 12 or less hours, 8 or less hours, 6 or less hours, 4 or less hours, 2 or less hours, 60 or less minutes, 45 or less minutes, 30 or less minutes, 25 or less minutes, 20 or less minutes, 15 or less minutes, 10 or less minutes, 5 or less minutes, or 2 or less minutes. A sample can be contacted by a permeabilization reagent at various temperatures, depending on the protocol and the reagent used. For example, in some instances a sample can be contacted by a permeabilization reagent at a temperature ranging from −82° C. to 55° C., where specific ranges of interest include, but are not limited to: 50 to 54° C., 40 to 44° C., 35 to 39° C., 28 to 32° C., 20 to 26° C., 0 to 6° C., −18 to −22° C., and −78 to −82° C. In some instances a sample can be contacted by a permeabilization reagent at a temperature of −80° C., −20° C., 4° C., room temperature (22-25° C.), 30° C., 37° C., 42° C., or 52° C.

In some embodiments, a sample is contacted with an enzymatic permeabilization reagent. Enzymatic permeabilization reagents that permeabilize a sample by partially degrading extracellular matrix or surface proteins that hinder the permeation of the sample by assay reagents. Contact with an enzymatic permeabilization reagent can take place at any point after fixation and prior to target detection. In some instances the enzymatic permeabilization reagent is proteinase K, a commercially available enzyme. In such cases, the sample is contacted with proteinase K prior to contact with a post-fixation reagent. Proteinase K treatment (i.e., contact by proteinase K; also commonly referred to as "proteinase K digestion") can be performed over a range of times at a range of temperatures, over a range of enzyme concentrations that are empirically determined for each cell type or tissue type under investigation. For example, a sample can be contacted by proteinase K for 30 or less minutes, 25 or less minutes, 20 or less minutes, 15 or less minutes, 10 or less minutes, 5 or less minutes, or 2 or less minutes. A sample can be contacted by 1 µg/ml or less, 2 µg/m or less, 4 µg/ml or less, 8 µg/ml or less, 10 µg/ml or less, 20 µg/ml or less, 30 µg/ml or less, 50 µg/ml or less, or 100 µg/ml or less proteinase K. A sample can be contacted by proteinase K at a temperature ranging from 2° C. to 55° C., where specific ranges of interest include, but are not limited to: 50 to 54° C., 40 to 44° C., 35 to 39° C., 28 to 32° C., 20 to 26° C., and 0 to 6° C. In some instances a sample can be contacted by proteinase K at a temperature of 4° C., room temperature (22-25° C.), 30° C., 37° C., 42° C., or 52° C. In some embodiments, a sample is not contacted with an enzymatic permeabilization reagent. In some embodiments, a sample is not contacted with proteinase K. Contact of an intact tissue with at least a fixation reagent and a permeabilization reagent results in the production of a fixed and permeabilized tissue.

Ligase

In some embodiments, the methods disclosed include adding ligase to ligate the second oligonucleotide and generate a closed nucleic acid circle. In some embodiments, the adding ligase includes adding DNA ligase. In alternative embodiments, the second oligonucleotide is provided as a closed nucleic acid circle, and the step of adding ligase is omitted. In certain embodiments, ligase is an enzyme that facilitates the sequencing of a target nucleic acid molecule.

The term "ligase" as used herein refers to an enzyme that is commonly used to join polynucleotides together or to join the ends of a single polynucleotide. Ligases include ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases include bacterial ligases such as *E. coli* DNA ligase and Taq DNA ligase, Ampligase® thermostable DNA ligase (Epicentre® Technologies Corp., part of Illumina®, Madison, Wis.) and phage ligases such as T3 DNA ligase, T4 DNA ligase and T7 DNA ligase and mutants thereof.

Rolling Circle Amplification

In some embodiments, the methods of the invention include the step of performing rolling circle amplification in the presence of a nucleic acid molecule, wherein the performing includes using the second oligonucleotide as a template and the first oligonucleotide as a primer for a polymerase to form one or more amplicons. In such embodiments, a single-stranded, circular polynucleotide template is formed by ligation of the second nucleotide, which circular polynucleotide includes a region that is complementary to the first oligonucleotide. Upon addition of a DNA polymerase in the presence of appropriate dNTP precursors and other cofactors, the first oligonucleotide is elongated by replication of multiple copies of the template. This amplification product can be readily detected by binding to a detection probe.

In some embodiments, only when a first oligonucleotide and second oligonucleotide hybridize to the same target nucleic acid molecule, the second oligonucleogide can be circularized and rolling-circle amplified to generate a cDNA nanoball (i.e., amplicon) containing multiple copies of the cDNA. The term "amplicon" refers to the amplified nucleic acid product of a PCR reaction or other nucleic acid amplification process. In some embodiments, amine-modified nucleotides are spiked into the rolling circle amplification reaction.

Techniques for rolling circle amplification are known in the art (see, e.g., Baner et al, Nucleic Acids Research, 26:5073-5078, 1998; Lizardi et al, Nature Genetics 19:226, 1998; Schweitzer et al. Proc. Natl Acad. Sci. USA 97:101 13-119, 2000; Faruqi et al, BMC Genomics 2:4, 2000; Nallur et al, Nucl. Acids Res. 29:e118, 2001; Dean et al. Genome Res. 11:1095-1099, 2001; Schweitzer et al, Nature Biotech. 20:359-365, 2002; U.S. Pat. Nos. 6,054,274, 6,291, 187, 6,323,009, 6,344,329 and 6,368,801). In some embodiments the polymerase is phi29 DNA polymerase.

In certain aspects, the nucleic acid molecule includes an amine-modified nucleotide. In such embodiments, the amine-modified nucleotide includes an acrylic acid N-hydroxysuccinimide moiety modification. Examples of other amine-modified nucleotides include, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

Amplicon Embedding in a Tissue-Hydrogel Setting

In some embodiments, the methods disclosed include embedding one or more amplicons in the presence of hydrogel subunits to form one or more hydrogel-embedded amplicons. The hydrogel-tissue chemistry described includes covalently attaching nucleic acids to in situ synthesized hydrogel for tissue clearing, enzyme diffusion, and multiple-cycle sequencing while an existing hydrogel-tis sue chemistry method cannot. In some embodiments, to enable amplicon embedding in the tissue-hydrogel setting, amine-modified nucleotides are spiked into the rolling circle amplification reaction, functionalized with an acrylamide moiety using acrylic acid N-hydroxysuccinimide esters, and copolymerized with acrylamide monomers to form a hydrogel.

As used herein, the terms "hydrogel" or "hydrogel network" mean a network of polymer chains that are water-insoluble, sometimes found as a colloidal gel in which water is the dispersion medium. In other words, hydrogels are a class of polymeric materials that can absorb large amounts of water without dissolving. Hydrogels can contain over 99% water and may include natural or synthetic polymers, or a combination thereof. Hydrogels also possess a degree of flexibility very similar to natural tissue, due to their significant water content. A detailed description of suitable hydrogels may be found in published U.S. patent application 20100055733, herein specifically incorporated by reference. As used herein, the terms "hydrogel subunits" or "hydrogel precursors" mean hydrophilic monomers, prepolymers, or polymers that can be crosslinked, or "polymerized", to form a three-dimensional (3D) hydrogel network. Without being bound by any scientific theory, it is believed that this fixation of the biological specimen in the presence of hydrogel subunits cros slinks the components of the specimen to the hydrogel subunits, thereby securing molecular components in place, preserving the tissue architecture and cell morphology.

In some embodiments, the embedding includes copolymerizing the one or more amplicons with acrylamide. As used herein, the term "copolymer" describes a polymer which contains more than one type of subunit. The term encompasses polymer which include two, three, four, five, or six types of subunits.

In certain aspects, the embedding includes clearing the one or more hydrogel-embedded amplicons wherein the target nucleic acid is substantially retained in the one or more hydrogel-embedded amplicons. In such embodiments, the clearing includes substantially removing a plurality of cellular components from the one or more hydrogel-embedded amplicons. In some other embodiments, the clearing includes substantially removing lipids from the one or more hydrogel-embedded amplicons. As used herein, the term "substantially" means that the original amount present in the sample before clearing has been reduced by approximately 70% or more, such as by 75% or more, such as by 80% or more, such as by 85% or more, such as by 90% or more, such as by 95% or more, such as by 99% or more, such as by 100%.

In some embodiments, clearing the hydrogel-embedded amplicons includes electrophoresing the specimen. In some embodiments, the amplicons are electrophoresed using a buffer solution that includes an ionic surfactant. In some embodiments, the ionic surfactant is sodium dodecyl sulfate (SDS). In some embodiments, the specimen is electrophoresed using a voltage ranging from about 10 to about 60 volts. In some embodiments, the specimen is electrophoresed for a period of time ranging from about 15 minutes up to about 10 days. In some embodiments, the methods further involve incubating the cleared specimen in a mounting medium that has a refractive index that matches that of the cleared tissue. In some embodiments, the mounting medium increases the optical clarity of the specimen. In some embodiments, the mounting medium includes glycerol.

Sequencing with Error-Correction by Dynamic Annealing and Ligation (SEDAL)

The methods disclosed herein include the step of contacting one or more hydrogel-embedded amplicons having the barcode sequence with a pair of primers under conditions to allow for ligation, wherein the pair of primers include a third oligonucleotide and a fourth oligonucleotide, wherein the ligation only occurs when both the third oligonucleotide and the fourth oligonucleotide ligate to the same amplicon. In some embodiments, SEDAL was devised specifically for STARmap. In such embodiments, the improved sequencing-by-ligation method herein includes operating at room temperature for best preservation of tissue morphology with low background noise and error reduction. In such other embodiments, the contacting the one or more hydrogel-embedded amplicons includes eliminating error accumulation as sequencing proceeds.

In some embodiments, the contacting the one or more hydrogel-embedded amplicons occurs two times or more, including, but not limited to, e.g., three times or more, four times or more, five times or more, six times or more, or seven times or more. In certain embodiments, the contacting the one or more hydrogel-embedded amplicons occurs four times or more for thin tissue specimens. In other embodiments, the contacting the one or more hydrogel-embedded amplicons occurs six times or more for thick tissue specimens. In some embodiments, one or more amplicons can be contacted by a pair of primers for 24 or more hours, 24 or less hours, 18 or less hours, 12 or less hours, 8 or less hours, 6 or less hours, 4 or less hours, 2 or less hours, 60 or less minutes, 45 or less minutes, 30 or less minutes, 25 or less minutes, 20 or less minutes, 15 or less minutes, 10 or less minutes, 5 or less minutes, or 2 or less minutes.

Specimens prepared using the subject methods may be analyzed by any of a number of different types of microscopy, for example, optical microscopy (e.g. bright field, oblique illumination, dark field, phase contrast, differential interference contrast, interference reflection, epifluorescence, confocal, etc., microscopy), laser microscopy, electron microscopy, and scanning probe microscopy. In some aspects, a non-transitory computer readable medium transforms raw images acquired through microscopy of multiple rounds of in situ sequencing first into decoded gene identities and spatial locations and then analyzes the per-cell composition of gene expression.

SEDAL Oligonucleotide Primers

In some embodiments, the methods disclosed include a third oligonucleotide and a fourth oligonucleotide. In certain aspects, the third oligonucleotide is configured to decode bases and the fourth oligonucleotide is configured to convert decoded bases into a signal. In some aspects, the signal is a fluorescent signal. In exemplary aspects, the contacting the one or more hydrogel-embedded amplicons having the barcode sequence with a pair of primers under conditions to allow for ligation involves each of the third oligonucleotide and the fourth oligonucleotide ligating to form a stable product for imaging only when a perfect match occurs. In certain aspects, the mismatch sensitivity of a ligase enzyme is used to determine the underlying sequence of the target nucleic acid molecule.

The term "perfectly matched", when used in reference to a duplex means that the polynucleotide and/or oligonucleotide strands making up the duplex form a double stranded structure with one another such that every nucleotide in each strand undergoes Watson-Crick base pairing with a nucleotide in the other strand. The term "duplex" includes, but is not limited to, the pairing of nucleoside analogs, such as deoxyinosine, nucleosides with 2-aminopurine bases, peptide nucleic acids (PNAs), and the like, that may be employed. A "mismatch" in a duplex between two oligonucleotides means that a pair of nucleotides in the duplex fails to undergo Watson-Crick bonding.

In some embodiments, the method includes a plurality of third oligonucleotides, including, but not limited to, 5 or more third oligonucleotides, e.g., 8 or more, 10 or more, 12 or more, 15 or more, 18 or more, 20 or more, 25 or more, 30 or more, 35 or more that hybridize to target nucleotide sequences. In some embodiments, a method of the present disclosure includes a plurality of third oligonucleotides, including, but not limited to, 15 or more third oligonucleotides, e.g., 20 or more, 30 or more, 40 or more, 50 or more, 60 or more, 70 or more, and up to 80 different first oligonucleotides that hybridize to 15 or more, e.g., 20 or more, 30 or more, 40 or more, 50 or more, 60 or more, 70 or more, and up to 80 different target nucleotide sequences. In some embodiments, the methods include a plurality of fourth oligonucleotides, including, but not limited to, 5 or more fourth oligonucleotides, e.g., 8 or more, 10 or more, 12 or more, 15 or more, 18 or more, 20 or more, 25 or more, 30 or more, 35 or more. In some embodiments, a method of the present disclosure includes a plurality of fourth oligonucleotides including, but not limited to, 15 or more fourth oligonucleotides, e.g., 20 or more, 30 or more, 40 or more, 50 or more, 60 or more, 70 or more, and up to 80 different first oligonucleotides that hybridize to 15 or more, e.g., 20 or more, 30 or more, 40 or more, 50 or more, 60 or more, 70 or more, and up to 80 different target nucleotide sequences. A plurality of oligonucleotide pairs can be used in a reaction, where one or more pairs specifically bind to each target nucleic acid. For example, two primer pairs can be used for one target nucleic acid in order to improve sensitivity and reduce variability. It is also of interest to detect a plurality of different target nucleic acids in a cell, e.g. detecting up to 2, up to 3, up to 4, up to 5, up to 6, up to 7, up to 8, up to 9, up to 10, up to 12, up to 15, up to 18, up to 20, up to 25, up to 30, up to 40 or more distinct target nucleic acids.

In certain embodiments, SEDAL involves a ligase with activity hindered by base mismatches, a third oligonucleotide, and a fourth oligonucleotide. The term "hindered" in this context refers to activity of a ligase that is reduced by approximately 20% or more, such as by 25% or more, such as by 50% or more, such as by 75% or more, such as by 90% or more, such as by 95% or more, such as by 99% or more, such as by 100%. In some embodiments, the third oligonucleotide has a length of 5-15 nucleotides, including, but not limited to, 5-13 nucleotides, 5-10 nucleotides, or 5-8 nucleotides. In some embodiments, the $T_m$ of the third oligonucleotide is at room temperature (22-25° C.). In some embodiments, the third oligonucleotide is degenerate, or partially thereof. In some embodiments, the fourth oligonucleotide has a length of 5-15 nucleotides, including, but not limited to, 5-13 nucleotides, 5-10 nucleotides, or 5-8 nucleotides. In some embodiments, the $T_m$ of the fourth oligonucleotide is at room temperature (22-25° C.). After each cycle of SEDAL corresponding to a base readout, the fourth oligonucleotides may be stripped, which eliminates error accumulation as sequencing proceeds. In such embodiments, the fourth oligonucleotides are stripped by formamide.

In some embodiments, SEDAL involves the washing of the third oligonucleotide and the fourth oligonucleotide to remove unbound oligonucleotides, thereafter revealing a fluorescent product for imaging. In certain exemplary embodiments, a detectable label can be used to detect one or more nucleotides and/or oligonucleotides described herein. In certain embodiments, a detectable label can be used to detect the one or more amplicons. Examples of detectable markers include various radioactive moieties, enzymes, prosthetic groups, fluorescent markers, luminescent markers, bioluminescent markers, metal particles, protein-protein binding pairs, protein-antibody binding pairs and the like. Examples of fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorimidases, phosphatases, peroxidases, cholinesterases and the like. Identifiable markers also include radioactive compounds such as $^{125}I$, $^{35}S$, $^{14}C$, or $^3H$. Identifiable markers are commercially available from a variety of sources.

Fluorescent labels and their attachment to nucleotides and/or oligonucleotides are described in many reviews, including Haugland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). Particular methodologies applicable to the invention are disclosed in the following sample of references: U.S. Pat. Nos. 4,757,141, 5,151,507 and 5,091,519. In one aspect, one or more fluorescent dyes are used as labels for labeled target sequences, e.g., as disclosed by U.S. Pat. No. 5,188,934 (4,7-dichlorofluorescein dyes); U.S. Pat. No. 5,366,860 (spectrally resolvable rhodamine dyes); U.S. Pat. No. 5,847, 162 (4,7-dichlororhodamine dyes); U.S. Pat. No. 4,318,846 (ether-substituted fluorescein dyes); U.S. Pat. No. 5,800,996 (energy transfer dyes); Lee et al.; U.S. Pat. No. 5,066,580 (xanthine dyes); U.S. Pat. No. 5,688,648 (energy transfer dyes); and the like. Labelling can also be carried out with quantum dots, as disclosed in the following patents and patent publications: U.S. Pat. Nos. 6,322,901, 6,576,291, 6,423,551, 6,251,303, 6,319,426, 6,426,513, 6,444,143, 5,990,479, 6,207,392, 2002/0045045 and 2003/0017264. As used herein, the term "fluorescent label" includes a signaling moiety that conveys information through the fluorescent absorption and/or emission properties of one or more molecules. Such fluorescent properties include fluorescence intensity, fluorescence lifetime, emission spectrum characteristics, energy transfer, and the like.

Commercially available fluorescent nucleotide analogues readily incorporated into nucleotide and/or oligonucleotide sequences include, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY™ FL-14-dUTP, BODIPY™ R-14-dUTP, BODIPY TMTR-14-dUTP, RHODAMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY™ R-14-UTP, BODIPY™ TR-14-UTP, RHODAMINE GREEN™-5-UTP, ALEXA FLUOR™ 488-5-UTP, LEXA FLUOR™ 546-14-UTP (Molecular Probes, Inc. Eugene, Oreg.) and the like. Protocols are known in the art for custom synthesis of nucleotides having other fluorophores (See, Henegariu et al. (2000) Nature Biotechnol. 18:345).

Other fluorophores available for post-synthetic attachment include, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY™ R, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, Cy7 (Amersham Biosciences, Piscataway, N.J.) and the like. FRET tandem fluorophores may also be used, including, but not limited to, PerCP-Cy5.5, PE-Cy5, PE-Cy5.5, PE-Cy7, PE-Texas Red, APC-Cy7, PE-Alexa dyes (610, 647, 680), APC-Alexa dyes and the like.

Metallic silver or gold particles may be used to enhance signal from fluorescently labeled nucleotide and/or oligonucleotide sequences (Lakowicz et al. (2003) Bio Techniques 34:62).

Biotin, or a derivative thereof, may also be used as a label on a nucleotide and/or an oligonucleotide sequence, and subsequently bound by a detectably labeled avidin/streptavidin derivative (e.g. phycoerythrin-conjugated streptavidin), or a detectably labeled anti-biotin antibody. Digoxigenin may be incorporated as a label and subsequently bound by a detectably labeled anti-digoxigenin antibody (e.g. fluoresceinated anti-digoxigenin). An aminoallyl-dUTP residue may be incorporated into an oligonucleotide sequence and subsequently coupled to an N-hydroxy succinimide (NHS) derivatized fluorescent dye. In general, any member of a conjugate pair may be incorporated into a detection oligonucleotide provided that a detectably labeled conjugate partner can be bound to permit detection. As used herein, the term antibody refers to an antibody molecule of any class, or any sub-fragment thereof, such as an Fab.

Other suitable labels for an oligonucleotide sequence may include fluorescein (FAM), digoxigenin, dinitrophenol (DNP), dansyl, biotin, bromodeoxyuridine (BrdU), hexahistidine (6× His), phosphor-amino acids (e.g. P-tyr, P-ser, P-thr) and the like. In one embodiment the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM.

In certain exemplary embodiments, a nucleotide and/or an oligonucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, PCT publication WO 91/17160 and the like. Many different hapten-capture agent pairs are available for use. Exemplary haptens include, but are not limited to, biotin, des-biotin and other derivatives, dinitrophenol, dansyl, fluorescein, CY5, digoxigenin and the like. For biotin, a capture agent may be avidin, streptavidin, or antibodies. Antibodies may be used as capture agents for the other haptens (many dye-antibody pairs being commercially available, e.g., Molecular Probes, Eugene, Oreg.).

Cells

Methods disclosed herein include a method for in situ gene sequencing of a target nucleic acid in a cell in an intact tissue. In certain embodiments, the cell is present in a population of cells. In certain other embodiments, the population of cells includes a plurality of cell types including, but not limited to, excitatory neurons, inhibitory neurons, and non-neuronal cells. Cells for use in the assays of the invention can be an organism, a single cell type derived from an organism, or can be a mixture of cell types. Included are naturally occurring cells and cell populations, genetically engineered cell lines, cells derived from transgenic animals, etc. Virtually any cell type and size can be accommodated. Suitable cells include bacterial, fungal, plant and animal cells. In one embodiment of the invention, the cells are mammalian cells, e.g. complex cell populations such as naturally occurring tissues, for example blood, liver, pancreas, neural tissue, bone marrow, skin, and the like. Some tissues may be disrupted into a monodisperse suspension. Alternatively, the cells may be a cultured population, e.g. a culture derived from a complex population, a culture derived from a single cell type where the cells have differentiated into multiple lineages, or where the cells are responding differentially to stimulus, and the like.

Cell types that can find use in the subject invention include stem and progenitor cells, e.g. embryonic stem cells, hematopoietic stem cells, mesenchymal stem cells, neural crest cells, etc., endothelial cells, muscle cells, myocardial, smooth and skeletal muscle cells, mesenchymal cells, epithelial cells; hematopoietic cells, such as lymphocytes, including T-cells, such as Th1 T cells, Th2 T cells, ThO T cells, cytotoxic T cells; B cells, pre-B cells, etc.; monocytes; dendritic cells; neutrophils; and macrophages; natural killer cells; mast cells, etc.; adipocytes, cells involved with particular organs, such as thymus, endocrine glands, pancreas, brain, such as neurons, glia, astrocytes, dendrocytes, etc. and genetically modified cells thereof. Hematopoietic cells may be associated with inflammatory processes, autoimmune diseases, etc., endothelial cells, smooth muscle cells, myocardial cells, etc. may be associated with cardiovascular diseases; almost any type of cell may be associated with neoplasias, such as sarcomas, carcinomas and lymphomas; liver diseases with hepatic cells; kidney diseases with kidney cells; etc.

The cells may also be transformed or neoplastic cells of different types, e.g. carcinomas of different cell origins, lymphomas of different cell types, etc. The American Type Culture Collection (Manassas, Va.) has collected and makes available over 4,000 cell lines from over 150 different species, over 950 cancer cell lines including 700 human cancer cell lines. The National Cancer Institute has compiled clinical, biochemical and molecular data from a large panel of human tumor cell lines, these are available from ATCC or the NCI (Phelps et al. (1996) Journal of Cellular Biochemistry Supplement 24:32-91). Included are different cell lines derived spontaneously, or selected for desired growth or response characteristics from an individual cell line; and may include multiple cell lines derived from a similar tumor type but from distinct patients or sites.

Cells may be non-adherent, e.g. blood cells including monocytes, T cells, B-cells; tumor cells, etc., or adherent cells, e.g. epithelial cells, endothelial cells, neural cells, etc. In order to profile adherent cells, they may be dissociated from the substrate that they are adhered to, and from other cells, in a manner that maintains their ability to recognize and bind to probe molecules.

Such cells can be acquired from an individual using, e.g., a draw, a lavage, a wash, surgical dissection etc., from a variety of tissues, e.g., blood, marrow, a solid tissue (e.g., a solid tumor), ascites, by a variety of techniques that are known in the art. Cells may be obtained from fixed or unfixed, fresh or frozen, whole or disaggregated samples. Disaggregation of tissue may occur either mechanically or enzymatically using known techniques.

Imaging

The methods disclosed include imaging the one or more hydrogel-embedded amplicons using any of a number of different types of microscopy, e.g., confocal microscopy, two-photon microscopy, light-field microscopy, intact tissue expansion microscopy, and/or CLARITY™-optimized light sheet microscopy (COLM).

Bright field microscopy is the simplest of all the optical microscopy techniques. Sample illumination is via transmitted white light, i.e. illuminated from below and observed from above. Limitations include low contrast of most biological samples and low apparent resolution due to the blur of out of focus material. The simplicity of the technique and the minimal sample preparation required are significant advantages.

In oblique illumination microscopy, the specimen is illuminated from the side. This gives the image a 3-dimensional appearance and can highlight otherwise invisible features. A more recent technique based on this method is Hoffmann's modulation contrast, a system found on inverted microscopes for use in cell culture. Though oblique illumination suffers from the same limitations as bright field microscopy (low contrast of many biological samples; low apparent resolution due to out of focus objects), it may highlight otherwise invisible structures.

Dark field microscopy is a technique for improving the contrast of unstained, transparent specimens. Dark field illumination uses a carefully aligned light source to minimize the quantity of directly-transmitted (unscattered) light entering the image plane, collecting only the light scattered by the sample. Dark field can dramatically improve image contrast (especially of transparent objects) while requiring little equipment setup or sample preparation. However, the technique suffers from low light intensity in final image of many biological samples, and continues to be affected by low apparent resolution.

Phase contrast is an optical microscopy illumination technique that converts phase shifts in light passing through a transparent specimen to brightness changes in the image. In other words, phase contrast shows differences in refractive index as difference in contrast. The phase shifts themselves are invisible to the human eye, but become visible when they are shown as brightness changes.

In differential interference contrast (DIC) microscopy, differences in optical density will show up as differences in relief. The system consists of a special prism (Nomarski prism, Wollaston prism) in the condenser that splits light in an ordinary and an extraordinary beam. The spatial difference between the two beams is minimal (less than the maximum resolution of the objective). After passage through the specimen, the beams are reunited by a similar prism in the objective. In a homogeneous specimen, there is no difference between the two beams, and no contrast is being generated. However, near a refractive boundary (e.g. a nucleus within the cytoplasm), the difference between the ordinary and the extraordinary beam will generate a relief in the image. Differential interference contrast requires a polarized light source to function; two polarizing filters have to be fitted in the light path, one below the condenser (the polarizer), and the other above the objective (the analyzer).

Another microscopic technique using interference is interference reflection microscopy (also known as reflected interference contrast, or RIC). It is used to examine the adhesion of cells to a glass surface, using polarized light of a narrow range of wavelengths to be reflected whenever there is an interface between two substances with different refractive indices. Whenever a cell is attached to the glass surface, reflected light from the glass and that from the attached cell will interfere. If there is no cell attached to the glass, there will be no interference.

A fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" refers to any microscope that uses fluorescence to generate an image, whether it is a more simple set up like an epifluorescence microscope, or a more complicated design such as a confocal microscope, which uses optical sectioning to get better resolution of the fluorescent image.

Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. COLM provides an alternative microscopy for fast 3D imaging of large clarified samples. COLM interrogates large immunostained tissues, permits increased speed of acquisition and results in a higher quality of generated data.

In single plane illumination microscopy (SPIM), also known as light sheet microscopy, only the fluorophores in the focal plane of the detection objective lens are illuminated. The light sheet is a beam that is collimated in one and focused in the other direction. Since no fluorophores are excited outside the detectors' focal plane, the method also provides intrinsic optical sectioning. Moreover, when compared to conventional microscopy, light sheet methods exhibit reduced photobleaching and lower phototoxicity, and often enable far more scans per specimen. By rotating the specimen, the technique can image virtually any plane with multiple views obtained from different angles. For every angle, however, only a relatively shallow section of the specimen is imaged with high resolution, whereas deeper regions appear increasingly blurred.

Super-resolution microscopy is a form of light microscopy. Due to the diffraction of light, the resolution of conventional light microscopy is limited as stated by Ernst Abbe in 1873. A good approximation of the resolution attainable is the FWHM (full width at half-maximum) of the point spread function, and a precise widefield microscope with high numerical aperture and visible light usually reaches a resolution of ~250 nm. Super-resolution techniques allow the capture of images with a higher resolution than the diffraction limit. They fall into two broad categories, "true" super-resolution techniques, which capture information contained in evanescent waves, and "functional" super-resolution techniques, which use experimental techniques and known limitations on the matter being imaged to reconstruct a super-resolution image.

Laser microscopy uses laser illumination sources in various forms of microscopy. For instance, laser microscopy focused on biological applications uses ultrashort pulse lasers, or femtosecond lasers, in a number of techniques including nonlinear microscopy, saturation microscopy, and multiphoton fluorescence microscopy such as two-photon excitation microscopy (a fluorescence imaging technique that allows imaging of living tissue up to a very high depth, e.g. one millimeter)

In electron microscopy (EM), a beam of electrons is used to illuminate a specimen and produce a magnified image. An electron microscope has greater resolving power than a light-powered optical microscope because electrons have wavelengths about 100,000 times shorter than visible light (photons). They can achieve better than 50 pm resolution and magnifications of up to about 10,000,000× whereas ordinary, non-confocal light microscopes are limited by diffraction to about 200 nm resolution and useful magnifications below 2000×. The electron microscope uses electrostatic and electromagnetic "lenses" to control the electron beam and focus it to form an image. These lenses are analogous to but different from the glass lenses of an optical microscope that form a magnified image by focusing light on or through the specimen. Electron microscopes are used to observe a wide range of biological and inorganic specimens including microorganisms, cells, large molecules, biopsy samples, metals, and crystals. Industrially, the electron microscope is often used for quality control and failure analysis. Examples of electron microscopy include Transmission electron microscopy (TEM), Scanning electron microscopy (SEM), reflection electron microscopy (REM), Scanning transmission electron microscopy (STEM) and low-voltage electron microscopy (LVEM).

Scanning probe microscopy (SPM) is a branch of microscopy that forms images of surfaces using a physical probe that scans the specimen. An image of the surface is obtained by mechanically moving the probe in a raster scan of the specimen, line by line, and recording the probe-surface interaction as a function of position. Examples of SPM include atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM).

Intact tissue expansion microscopy (exM) enables imaging of thick preserve specimens with roughly 70 nm lateral resolution. Using ExM the optical diffraction limit is circumvented by physically expanding a biological specimen before imaging, thus bringing sub-diffraction limited structures into the size range viewable by a conventional diffraction-limited microscope. ExM can image biological specimens at the voxel rates of a diffraction limited microscope, but with the voxel sizes of a super-resolution microscope. Expanded samples are transparent, and index-matched to water, as the expanded material is >99% water. Techniques of expansion microscopy are known in the art, e.g., as disclosed in Gao et al., Q&A: Expansion Microscopy, BMC Biol. 2017; 15:50.

Screening Methods

The methods disclosed herein also provide for a method of screening a candidate agent to determine whether the candidate agent modulates gene expression of a nucleic acid in a cell in an intact tissue, the method including: (a) contacting a fixed and permeabilized intact tissue with at least a pair of oligonucleotide primers under conditions to allow for specific hybridization, wherein the pair of primers include a first oligonucleotide and a second oligonucleotide; wherein each of the first oligonucleotide and the second oligonucleotide includes a first complementarity region, a second complementarity region, and a third complementarity region; wherein the second oligonucleotide further includes a barcode sequence; wherein the first complementarity region of the first oligonucleotide is complementary to a first portion of the target nucleic acid, wherein the second complementarity region of the first oligonucleotide is complementary to the first complementarity region of the second oligonucleotide, wherein the third complementarity region of the first oligonucleotide is complementary to the third complementarity region of the second oligonucleotide, wherein the second complementary region of the second oligonucleotide is complementary to a second portion of the target nucleic acid, and wherein the first complementarity region of the first oligonucleotide is adjacent to the second complementarity region of the second oligonucleotide; (b) adding ligase to ligate the second oligonucleotide and generate a closed nucleic acid circle; (c) performing rolling circle amplification in the presence of a nucleic acid molecule, wherein the performing includes using the second oligonucleotide as a template and the first oligonucleotide as a primer for a polymerase to form one or more amplicons; (d) embedding the one or more amplicons in the presence of hydrogel subunits to form one or more hydrogel-embedded amplicons; (e) contacting the one or more hydrogel-embedded amplicons having the barcode sequence with a pair of primers under conditions to allow for ligation, wherein the pair of primers include a third oligonucleotide and a fourth oligonucleotide, wherein the ligation only occurs when both the third oligonucleotide and the fourth oligonucleotide ligate to the same amplicon; (f) reiterating step (e); (g) imaging the one or more hydrogel-embedded amplicons to determine in situ gene sequencing of the target nucleic acid in the cell in the intact tissue; and (h) detecting the level of gene expression of the target nucleic acid, wherein an alteration in the level of expression of the target nucleic acid in the presence of the at least one candidate agent relative to the level of expression of the target nucleic acid in the absence of the at least one candidate agent indicates that the at least one candidate agent modulates gene expression of the nucleic acid in the cell in the intact tissue. Such screening methods include the steps of STARmap provided herein.

In some aspects, the detecting includes performing flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy. In certain aspects, the flow cytometry is mass cytometry or fluorescence-activated flow cytometry. In some other aspects, the detecting includes performing microscopy, scanning mass spectrometry or other imaging techniques described herein. In such aspects, the detecting includes determining a signal, e.g. a fluorescent signal.

By "test agent," "candidate agent," and grammatical equivalents herein, which terms are used interchangeably herein, is meant any molecule (e.g. proteins (which herein includes proteins, polypeptides, and peptides), small (i.e., 5-1000 Da, 100-750 Da, 200-500 Da, or less than 500 Da in size), or organic or inorganic molecules, polysaccharides, polynucleotides, etc.) which are to be tested for activity in a subject assay.

A variety of different candidate agents may be screened by the above methods. Candidate agents encompass numerous chemical classes, e.g., small organic compounds having a molecular weight of more than 50 daltons (e.g., at least about 50 Da, at least about 100 Da, at least about 150 Da, at least about 200 Da, at least about 250 Da, or at least about 500 Da) and less than about 20,000 daltons, less than about 10,000 daltons, less than about 5,000 daltons, or less than about 2,500 daltons. For example, in some embodiments, a suitable candidate agent is an organic compound having a molecular weight in a range of from about 500 Da to about 20,000 Da, e.g., from about 500 Da to about 1000 Da, from about 1000 Da to about 2000 Da, from about 2000 Da to about 2500 Da, from about 2500 Da to about 5000 Da, from about 5000 Da to about 10,000 Da, or from about 10,000 Da to about 20,000 Da.

Candidate agents can include functional groups necessary for structural interaction with proteins, e.g., hydrogen bonding, and can include at least an amine, carbonyl, hydroxyl or carboxyl group, or at least two of the functional chemical groups. The candidate agents can include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Moreover, screening may be directed to known pharmacologically active compounds and chemical analogs thereof, or to new agents with unknown properties such as those created through rational drug design.

In one embodiment, candidate modulators are synthetic compounds. Any number of techniques is available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

In another embodiment, the candidate agents are provided as libraries of natural compounds in the form of bacterial, fungal, plant and animal extracts that are available or readily produced. Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In one embodiment, candidate agents include proteins (including antibodies, antibody fragments (i.e., a fragment containing an antigen-binding region, single chain antibodies, and the like), nucleic acids, and chemical moieties. In one embodiment, the candidate agents are naturally occurring proteins or fragments of naturally occurring proteins. Thus, for example, cellular extracts containing proteins, or random or directed digests of proteinaceous cellular extracts, may be tested. In this way libraries of prokaryotic and eukaryotic proteins may be made for screening. Other embodiments include libraries of bacterial, fungal, viral, and mammalian proteins (e.g., human proteins).

In one embodiment, the candidate agents are organic moieties. In this embodiment, as is generally described in WO 94/243 14, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

Devices and Systems

Also included are devices for performing aspects of the subject methods. The subject devices may include, for example, imaging chambers, electrophoresis apparatus, flow chambers, microscopes, needles, tubing, pumps.

The present disclosure also provides systems for performing the subject methods. Systems may include one or more of the modules described herein, e.g. a power supply, a refrigeration unit, waste, a heating unit, a pump, etc. Systems may also include any of the reagents described herein, e.g. imaging buffer, wash buffer, strip buffer, Nissl and DAPI solutions. Systems in accordance with certain embodiments may also include a microscope and/or related imaging equipment, e.g., camera components, digital imaging components and/or image capturing equipment, computer processors configured to collect images according to one or more user inputs, and the like.

As discussed above, the systems described herein include a fluidics device having an imaging chamber and a pump; and a processor unit configured to perform the methods for in situ gene sequencing of a target nucleic acid in a cell in an intact tissue described herein. In some embodiments, the system enables the automation of STARmap, a process described herein as including, but not limited to, repeated rounds of hybridization of probes with DNA embedded in a gel, ligation of fluorescently labeled oligonucleotides onto these probes, washing off the excess probes, imaging, and stripping off the probes for the next round of sequencing. In some embodiments, the system may allow for continual operation. In some embodiments, the system includes an imaging chamber for flowing sequencing chemicals involved in in situ DNA sequencing over a sample. In some embodiments, the system of fluidics and pumps control sequencing chemical delivery to the sample.

Buffers may be added/removed/recirculated/replaced by the use of the one or more ports and optionally, tubing, pumps, valves, or any other suitable fluid handling and/or fluid manipulation equipment, for example, tubing that is removably attached or permanently attached to one or more components of a device. For example, a first tube having a first and second end may be attached to a first port and a second tube having a first and second end may be attached to a second port, where the first end of the first tube is attached to the first port and the second end of the first tube is operably linked to a receptacle, e.g. a cooling unit, heating unit, filtration unit, waste receptacle, etc.; and the first end of the second tube is attached to the second port and the second end of the second tube is operably linked to a receptacle, e.g. a cooling unit, beaker on ice, filtration unit, waste receptacle, etc.

In some embodiments, the system includes a non-transitory computer-readable storage medium that has instructions, which when executed by the processor unit, cause the processor unit to control the delivery of chemicals and synchronize this process with a microscope. In some embodiments, the non-transitory computer-readable storage medium includes instructions, which when executed by the processor unit, cause the processor unit to measure an optical signal.

Utility

The devices, methods, and systems herein find a number of uses in the art such as in biomedical research and/or clinical diagnostics. For example, in biomedical research, applications include, but are not limited to, spatially resolved gene expression analysis for fundamental biology or drug screening. In clinical diagnostics, applications include, but are not limited to, detecting gene markers such as disease, immune responses, bacterial or viral DNA/RNA for patient samples. Examples of advantages of the methods described herein include efficiency, where it takes merely 3 or 4 days to obtain final data from a raw sample, providing speeds much faster than existing microarray or sequencing technology; highly multiplexed (up to 1000 genes); single-cell and single-molecule sensitivity; preserved tissue morphology; and/or high signal-to-noise ratio with low error rates.

In certain aspects, STARmap may be applied to the study of molecular-defined cell types and activity-regulated gene expression in mouse visual cortex, and to be scalable to larger 3D tissue blocks to visualize short- and long-range spatial organization of cortical neurons on a volumetric scale not previously accessible. In some embodiments, the methods disclosed herein may be adapted to image DNA-conjugated antibodies for highly multiplexed protein detection.

The devices, methods, and systems of the invention can also be generalized to study a number of heterogeneous cell populations in diverse tissues. Without being bound by any scientific theory, the brain poses special challenges well suited to STARmap analysis. For example, the polymorphic activity-regulated gene (ARG) expression observed across different cell types is likely to depend on both intrinsic cell-biological properties (such as signal transduction pathway-component expression), and on extrinsic properties such as neural circuit anatomy that routes external sensory information to different cells (here in visual cortex). In such cases, in situ transcriptomics exemplified by STARmap can effectively link imaging-based molecular information with anatomical and activity information, thus elucidating brain function and dysfunction.

The devices, methods, and systems disclosed herein enable cellular components, e.g. lipids that normally provide structural support but that hinder visualization of subcellular proteins and molecules to be removed while preserving the 3-dimensional architecture of the cells and tissue because the sample is crosslinked to a hydrogel that physically supports the ultrastructure of the tissue. This removal renders the interior of biological specimen substantially permeable to light and/or macromolecules, allowing the interior of the specimen, e.g. cells and subcellular structures, to be microscopically visualized without time-consuming and disruptive sectioning of the tissue. The procedure is also more rapid than procedures commonly used in the art, as clearance and permeabilization, typically performed in separate steps, may be combined in a single step of removing cellular components. Additionally, the specimen can be iteratively stained, unstained, and re-stained with other reagents for comprehensive analysis. Further functionalization with the polymerizable acrylamide moiety enables amplicons to be covalently anchored within the polyacrylamide network at multiple sites.

In one example, the subject devices, methods, and systems may be employed to evaluate, diagnose or monitor a disease. "Diagnosis" as used herein generally includes a prediction of a subject's susceptibility to a disease or disorder, determination as to whether a subject is presently affected by a disease or disorder, prognosis of a subject affected by a disease or disorder (e.g., identification of cancerous states, stages of cancer, likelihood that a patient will die from the cancer), prediction of a subject's responsiveness to treatment for a disease or disorder (e.g., a positive response, a negative response, no response at all to, e.g., allogeneic hematopoietic stem cell transplantation, chemotherapy, radiation therapy, antibody therapy, small molecule compound therapy) and use of therametrics (e.g., monitoring a subject's condition to provide information as to the effect or efficacy of therapy). For example, a biopsy may be prepared from a cancerous tissue and microscopically analyzed to determine the type of cancer, the extent to which the cancer has developed, whether the cancer will be responsive to therapeutic intervention, etc.

The subject devices, methods, and systems also provide a useful technique for screening candidate therapeutic agents for their effect on a tissue or a disease. For example, a subject, e.g. a mouse, rat, dog, primate, human, etc. may be contacted with a candidate agent, an organ or a biopsy thereof may be prepared by the subject methods, and the prepared specimen microscopically analyzed for one or more cellular or tissue parameters. Parameters are quantifiable components of cells or tissues, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. Thus, for example, one such method may include detecting cellular viability, tissue vascularization, the presence of immune cell infiltrates, efficacy in altering the progression of the disease, etc. In some embodiments, the screen includes comparing the analyzed parameter(s) to those from a control, or reference, sample, e.g., a specimen similarly prepared from a subject not contacted with the candidate agent. Candidate agents of interest for screening include known and unknown compounds that encompass numerous chemical classes, primarily organic molecules, which may include organometallic molecules, inorganic molecules, genetic sequences, etc. Candidate agents of interest for screening also include nucleic acids, for example, nucleic acids that encode siRNA, shRNA, antisense molecules, or miRNA, or nucleic acids that encode polypeptides. An important aspect of the invention is to evaluate candidate drugs, including toxicity testing; and the like. Evaluations of tissue samples using the subject methods may include, e.g., genetic, transcriptomic, genomic, proteomic, and/or metabolomics analyses.

The subject devices, methods, and systems may also be used to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, ancestry, and the like. Such detection may be used in, for example, diagnosing and monitoring disease as, e.g., described above, in personalized medicine, and in studying paternity.

A database of analytic information can be compiled. These databases may include results from known cell types, references from the analysis of cells treated under particular conditions, and the like. A data matrix may be generated, where each point of the data matrix corresponds to a readout from a cell, where data for each cell may include readouts from multiple labels. The readout may be a mean, median or the variance or other statistically or mathematically derived value associated with the measurement. The output readout information may be further refined by direct comparison with the corresponding reference readout. The absolute values obtained for each output under identical conditions will display a variability that is inherent in live biological systems and also reflects individual cellular variability as well as the variability inherent between individuals.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-89 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method for in situ gene sequencing of a target nucleic acid in a cell in an intact tissue, the method comprising:
   (a) contacting a fixed and permeabilized intact tissue with at least a pair of oligonucleotide primers under conditions to allow for specific hybridization, wherein the pair of primers comprise a first oligonucleotide and a second oligonucleotide; wherein each of the first oligonucleotide and the second oligonucleotide comprises a first complementarity region, a second complementarity region, and a third complementarity region; wherein the second oligonucleotide further comprises a barcode sequence; wherein the first complementarity region of the first oligonucleotide is complementary to a first portion of the target nucleic acid, wherein the second complementarity region of the first oligonucleotide is complementary to the first complementarity region of the second oligonucleotide, wherein the third complementarity region of the first oligonucleotide is complementary to the third complementarity region of the second oligonucleotide, wherein the second complementarity region of the second oligonucleotide is complementary to a second portion of the target nucleic acid, and wherein the first complementarity region of the first oligonucleotide is adjacent to the second complementarity region of the second oligonucleotide;
   (b) adding ligase to ligate the second oligonucleotide and generate a closed nucleic acid circle;
   (c) performing rolling circle amplification in the presence of a nucleic acid molecule, wherein the performing comprises using the second oligonucleotide as a template and the first oligonucleotide as a primer for a polymerase to form one or more amplicons;
   (d) embedding the one or more amplicons in the presence of hydrogel subunits to form one or more hydrogel-embedded amplicons;
   (e) contacting the one or more hydrogel-embedded amplicons having the barcode sequence with a pair of primers under conditions to allow for ligation, wherein the pair of primers comprise a third oligonucleotide and a fourth oligonucleotide, wherein the ligation only occurs when both the third oligonucleotide and the fourth oligonucleotide ligate to the same amplicon;
   (f) reiterating step (e); and
   (g) imaging the one or more hydrogel-embedded amplicons to determine in situ gene sequencing of the target nucleic acid in the cell in the intact tissue.

2. The method of aspect 1, wherein the pair of primers are denatured by heating before contacting the sample.

3. The method of aspect 1 or 2, wherein the cell is present in a population of cells.

4. The method of aspect 3, wherein the population of cells comprises a plurality of cell types.

5. The method of any one of aspects 1-4, wherein the contacting the fixed and permeabilized intact tissue comprises hybridizing the pair of primers to the same target nucleic acid.

6. The method of any one of aspects 1-5, wherein the target nucleic acid is RNA.

7. The method of aspect 6, wherein the RNA is mRNA.

8. The method of any one of aspects 1-5, wherein the target nucleic acid is DNA.

9. The method of any one of aspects 1-8, wherein the second oligonucleotide comprises a padlock probe.

10. The method of any one of aspects 1-9, wherein the first complementarity region of the first oligonucleotide has a length of 19-25 nucleotides.

11. The method of any one of aspects 1-10, wherein the second complementarity region of the first oligonucleotide has a length of 6 nucleotides.

12. The method of any one of aspects 1-11, wherein the third complementarity region of the first oligonucleotide has a length of 6 nucleotides.

13. The method of any one of aspects 1-12, wherein the first complementarity region of the second oligonucleotide has a length of 6 nucleotides.

14. The method of any one of aspects 1-13, wherein the second complementarity region of the second oligonucleotide has a length of 19-25 nucleotides.

15. The method of any one of aspects 1-14, wherein the third complementarity region of the second oligonucleotide has a length of 6 nucleotides.

16. The method of any one of aspects 1-15, wherein the first complementarity region of the second oligonucleotide comprises the 5' end of the second oligonucleotide.

17. The method of any one of aspects 1-16, wherein the third complementarity region of the second oligonucleotide comprises the 3' end of the second oligonucleotide.
18. The method of any one of aspects 1-17, wherein the first complementarity region of the second oligonucleotide is adjacent to the third complementarity region of the second oligonucleotide.
19. The method of any one of aspects 1-18, wherein the barcode sequence of the second oligonucleotide provides barcoding information for identification of the target nucleic acid.
20. The method of any one of aspects 1-19, wherein the contacting the fixed and permeabilized intact tissue comprises hybridizing a plurality of oligonucleotide primers having specificity for different target nucleic acids.
21. The method of aspect 1, wherein the second oligonucleotide is provided as a closed nucleic acid circle, and the step of adding ligase is omitted.
22. The method of any of aspects 1-21, wherein the melting temperature ($T_m$) of oligonucleotides is selected to minimize ligation in solution.
23. The method of any one of aspects 1-22, wherein the adding ligase comprises adding DNA ligase.
24. The method of any one of aspects 1-23, wherein the nucleic acid molecule comprises an amine-modified nucleotide.
25. The method of aspect 24, wherein the amine-modified nucleotide comprises an acrylic acid N-hydroxysuccinimide moiety modification.
26. The method of any one of aspects 1-25, wherein the embedding comprises copolymerizing the one or more amplicons with acrylamide.
27. The method of any one of aspects 1-26, wherein the embedding comprises clearing the one or more hydrogel-embedded amplicons wherein the target nucleic acid is substantially retained in the one or more hydrogel-embedded amplicons.
28. The method of aspect 27, wherein the clearing comprises substantially removing a plurality of cellular components from the one or more hydrogel-embedded amplicons.
29. The method of aspect 27 or 28, wherein the clearing comprises substantially removing lipids from the one or more hydrogel-embedded amplicons.
30. The method of any one of aspects 1-29, wherein the third oligonucleotide is configured to decode bases.
31. The method of any one of aspects 1-30, wherein the fourth oligonucleotide is configured to convert decoded bases into a signal.
32. The method of aspect 31, wherein the signal is a fluorescent signal.
33. The method of any one of aspects 1-32, wherein the contacting the one or more hydrogel-embedded amplicons comprises eliminating error accumulation as sequencing proceeds.
34. The method of any one of aspects 1-33, wherein the imaging comprises imaging the one or more hydrogel-embedded amplicons using confocal microscopy, two-photon microscopy, light-field microscopy, intact tissue expansion microscopy, and/or CLARITY™-optimized light sheet microscopy (COLM).
35. The method of any one of aspects 1-34, wherein the intact tissue is a thin slice.
36. The method of aspect 35, wherein the intact tissue has a thickness of 5-20 μm.
37. The method of aspect 35 or 36, wherein the contacting the one or more hydrogel-embedded amplicons occurs four times or more.
38. The method of aspect 35 or 36, wherein the contacting the one or more hydrogel-embedded amplicons occurs five times or more.
39. The method of any one of aspects 1-34, wherein the intact tissue is a thick slice.
40. The method of aspect 39, wherein the intact tissue has a thickness of 50-200 μm.
41. The method of aspect 39 or 40, wherein the contacting the one or more hydrogel-embedded amplicons occurs six times or more.
42. The method of aspect 39 or 40, wherein the contacting the one or more hydrogel-embedded amplicons occurs seven times or more.
43. A method of screening a candidate agent to determine whether the candidate agent modulates gene expression of a nucleic acid in a cell in an intact tissue, the method comprising:
  (a) contacting a fixed and permeabilized intact tissue with at least a pair of oligonucleotide primers under conditions to allow for specific hybridization, wherein the pair of primers comprise a first oligonucleotide and a second oligonucleotide;
    wherein each of the first oligonucleotide and the second oligonucleotide comprises a first complementarity region, a second complementarity region, and a third complementarity region;
    wherein the second oligonucleotide further comprises a barcode sequence;
    wherein the first complementarity region of the first oligonucleotide is complementary to a first portion of the target nucleic acid, wherein the second complementarity region of the first oligonucleotide is complementary to the first complementarity region of the second oligonucleotide, wherein the third complementarity region of the first oligonucleotide is complementary to the third complementarity region of the second oligonucleotide, wherein the second complementary region of the second oligonucleotide is complementary to a second portion of the target nucleic acid, and wherein the first complementarity region of the first oligonucleotide is adjacent to the second complementarity region of the second oligonucleotide;
  (b) adding ligase to ligate the second oligonucleotide and generate a closed nucleic acid circle;
  (c) performing rolling circle amplification in the presence of a nucleic acid molecule, wherein the performing comprises using the second oligonucleotide as a template and the first oligonucleotide as a primer for a polymerase to form one or more amplicons;
  (d) embedding the one or more amplicons in the presence of hydrogel subunits to form one or more hydrogel-embedded amplicons;
  (e) contacting the one or more hydrogel-embedded amplicons having the barcode sequence with a pair of primers under conditions to allow for ligation, wherein the pair of primers comprise a third oligonucleotide and a fourth oligonucleotide, wherein the ligation only occurs when both the third oligonucleotide and the fourth oligonucleotide ligate to the same amplicon;

(f) reiterating step (e);

(g) imaging the one or more hydrogel-embedded amplicons to determine in situ gene sequencing of the target nucleic acid in the cell in the intact tissue; and (h) detecting the level of gene expression of the target nucleic acid, wherein an alteration in the level of expression of the target nucleic acid in the presence of the at least one candidate agent relative to the level of expression of the target nucleic acid in the absence of the at least one candidate agent indicates that the at least one candidate agent modulates gene expression of the nucleic acid in the cell in the intact tissue.

44. The method of aspect 43, wherein the pair of primers are denatured by heating before contacting the sample.

45. The method of aspect 43 or 44, wherein the cell is present in a population of cells.

46. The method of aspect 45, wherein the population of cells comprises a plurality of cell types.

47. The method of any one of aspects 43-46, wherein the contacting the fixed and permeabilized intact tissue comprises hybridizing the pair of primers to the same target nucleic acid.

48. The method of any one of aspects 43-47, wherein the target nucleic acid is RNA.

49. The method of Aspect 48, wherein the RNA is mRNA.

50. The method of any one of aspects 43-47, wherein the target nucleic acid is DNA.

51. The method of any one of aspects 43-50, wherein the second oligonucleotide comprises a padlock probe.

52. The method of any one of aspects 43-51, wherein the first complementarity region of the first oligonucleotide has a length of 19-25 nucleotides.

53. The method of any one of aspects 43-52, wherein the second complementarity region of the first oligonucleotide has a length of 6 nucleotides.

54. The method of any one of aspects 43-53, wherein the third complementarity region of the first oligonucleotide has a length of 6 nucleotides.

55. The method of any one of aspects 43-54, wherein the first complementarity region of the second oligonucleotide has a length of 6 nucleotides.

56. The method of any one of aspects 43-55, wherein the second complementarity region of the second oligonucleotide has a length of 19-25 nucleotides.

57. The method of any one of aspects 43-56, wherein the third complementarity region of the second oligonucleotide has a length of 6 nucleotides.

58. The method of any one of aspects 43-57, wherein the first complementarity region of the second oligonucleotide comprises the 5' end of the second oligonucleotide.

59. The method of any one of aspects 43-58, wherein the third complementarity region of the second oligonucleotide comprises the 3' end of the second oligonucleotide.

60. The method of any one of aspects 43-59, wherein the first complementarity region of the second oligonucleotide is adjacent to the third complementarity region of the second oligonucleotide.

61. The method of any one of aspects 43-60, wherein the barcode sequence of the second oligonucleotide provides barcoding information for identification of the target nucleic acid.

62. The method of any one of aspects 43-61, wherein the contacting the fixed and permeabilized intact tissue comprises hybridizing a plurality of oligonucleotide primers having specificity for different target nucleic acids.

63. The method of aspect 43, wherein the second oligonucleotide is provided as a closed nucleic acid circle, and the step of adding ligase is omitted.

64. The method of any of aspects 43-63, wherein the melting temperature ($T_m$) of oligonucleotides is selected to minimize ligation in solution.

65. The method of any one of aspects 43-64, wherein the adding ligase comprises adding DNA ligase.

66. The method of any one of aspects 43-65, wherein the nucleic acid molecule comprises an amine-modified nucleotide.

67. The method of aspect 66, wherein the amine-modified nucleotide comprises an acrylic acid N-hydroxysuccinimide moiety modification.

68. The method of any one of aspects 43-67, wherein the embedding comprises copolymerizing the one or more amplicons with acrylamide.

69. The method of any one of aspects 43-68, wherein the embedding comprises clearing the one or more hydrogel-embedded amplicons wherein the target nucleic acid is substantially retained in the one or more hydrogel-embedded amplicons.

70. The method of aspect 69, wherein the clearing comprises substantially removing a plurality of cellular components from the one or more hydrogel-embedded amplicons.

71. The method of aspect 69 or 70, wherein the clearing comprises substantially removing lipids from the one or more hydrogel-embedded amplicons.

72. The method of any one of aspects 43-71, wherein the third oligonucleotide is configured to decode bases.

73. The method of any one of aspects 43-72, wherein the fourth oligonucleotide is configured to convert decoded bases into a signal.

74. The method of aspect 73, wherein the signal is a fluorescent signal.

75. The method of any one of aspects 43-74, wherein the contacting the one or more hydrogel-embedded amplicons comprises eliminating error accumulation as sequencing proceeds.

76. The method of any one of aspects 43-75, wherein the imaging comprises imaging the one or more hydrogel-embedded amplicons using confocal microscopy, two-photon microscopy, light-field microscopy, intact tissue expansion microscopy, and/or CLARITY™-optimized light sheet microscopy (COLM).

77. The method of any one of aspects 43-76, wherein the intact tissue is a thin slice.

78. The method of aspect 77, wherein the intact tissue has a thickness of 5-20 μm.

79. The method of aspect 77 or 78, wherein the contacting the one or more hydrogel-embedded amplicons occurs four times or more.

80. The method of aspect 77 or 78, wherein the contacting the one or more hydrogel-embedded amplicons occurs five times or more.

81. The method of any one of aspects 43-76, wherein the intact tissue is a thick slice.

82. The method of aspect 81, wherein the intact tissue has a thickness of 50-200 μm.

83. The method of aspect 81 or 82, wherein the contacting the one or more hydrogel-embedded amplicons occurs six times or more.

84. The method of aspect 81 or 82, wherein the contacting the one or more hydrogel-embedded amplicons occurs seven times or more.
85. The method of any one of aspects 43-84, wherein the detecting comprises performing flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy.
86. The method of aspect 85, wherein the flow cytometry is mass cytometry or fluorescence-activated flow cytometry.
87. The method of any one of aspects 43-86, wherein the detecting comprises performing microscopy, scanning mass spectrometry or other imaging techniques
88. The method of any one of aspects 43-87, wherein the detecting comprises determining a signal.
89. The method of aspect 88, wherein the signal is a fluorescent signal.
90. A system, comprising:
   a fluidics device comprising an imaging chamber and a pump; and
   a processor unit configured to perform any one of aspects 1-42.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

The following materials and methods generally apply to the results presented in the Examples described herein except where noted otherwise.

Mice

All animal procedures followed animal care guidelines approved by Stanford University's Administrative Panel on Laboratory Animal Care (APLAC) and guidelines of the National Institutes of Health. Male C57/BL6 mice (6-10 weeks) were used for experiments. For dark/light experiments, mice were housed on a standard light cycle followed by placement in constant darkness for 5 days. After dark housing, mice were either sacrificed or light-exposed for 1 hour before sacrifice. For cocaine experiments, mice were injected with either saline or 15 mg/kg cocaine 1 hour before sacrifice. For thin sections, animals were anesthetized with isofluorane and rapidly decapitated. Brain tissue was removed, placed in O.C.T, frozen in liquid nitrogen, and sliced using a cryostat (Leica CM1900; detailed information below in the thin-tissue slice section). For large volume samples, animals were anesthetized with Buprenex (100 mg/ml, i.p.), transcardially perfused with cold PBS, then perfused with 4% PFA (detailed information below in the large-volume sample section). Thy1-YFP mice were B6.Cg-Tg(Thy1-YFP)HJrs/J. Transgenic parvalbumin mice were generated by crossing Parv-IRES-Cre (JAX #8069) and Ai14 (JAX #7908) mice.

Chemicals and Enzymes

Chemicals and enzymes listed as follows by name (supplier, catalog number): Gel Slick Solution (Lonza, 50640). PlusOne Bind-Silane (GE Healthcare, 17-1330-01). Poly-L-lysine solution, 0.1% w/v (Sigma, P8920). Ultrapure distilled water (Invitrogen, 10977-015). Glass bottom 12-well and 24-well plates (MatTek, P12G-1.5-14-F and P24G-1.5-13-F). #2 Micro coverglass, 12 mm diameter (Electron Microscope Sciences, 72226-01). O.C.T. Compound (Fisher, 23-730-571). 16% PFA, EM grade (Electron Microscope Sciences, 15710-S). Methanol for HPLC (Sigma-Aldrich, 34860-1L-R). PBS, 7.4 (Gibco, 10010-023 for 1× and 70011-044 for 10×). Tween-20, 10% solution (Calbiochem, 655206). Triton-X-100, 10% solution (Sigma-Aldrich, 93443). OmniPur Formamide (Calbiochem, 75-12-7). 20×SSC buffer (Sigma-Aldrich, S6639). Ribonucleoside vanadyl complex (New England Biolabs, S1402S). Sheared salmon sperm DNA (Invitrogen, AM9680). SUPERase·In (Invitrogen, AM2696). T4 DNA ligase, 5 Weiss U/μL (Thermo Scientific, EL0011). Phi29 DNA polymerase (Thermo Scientific, EP0094). 10 mM dNTP mix (Invitrogen, 100004893). BSA, molecular biology grade (New England Biolabs, B9000S). 5-(3-aminoallyl)-dUTP (Invitrogen, AM8439). BSPEG9 (Thermo Scientific, 21582). Acrylic acid NHS ester, 90% (Sigma-Aldrich, A8060). Methacrylic acid NHS ester, 98% (Sigma-Aldrich, 730300). DMSO, anhydrous (Molecular Probes, D12345). Acrylamide solution, 40% (Bio-Rad, 161-0140). Bis Solution, 2% (Bio-Rad, 161-0142). Ammonium persulfate (Sigma-Aldrich, A3678). N,N,N',N'-Tetramethylethylenediamine (Sigma-Aldrich, T9281). OmniPur SDS, 20% (Calbiochem, 7991). Protease K, RNA grade (Invitrogen, 25530049). Shrimp Alkaline Phosphatase (New England Biolabs, M0371L). DAPI (Molecular Probes, D1306). NeuroTrace Fluorescent Nissl Stains, yellow (Molecular Probes, N-21480). PMSF (Sigma, 93482). Papain (Worthington, LS003127). Matrigel (Corning Life Sciences, 356234). Neurobasal-A medium (Invitrogen, 21103-049). FBS (HyClone, SH3007103). B-27 supplement (Gibco, 17504044). 2 mM Glutamax (Gibco, 35050-061). Fluorodeoxyuridine (Sigma, F-0503). Anti-NeuN antibody (Abcam, 190565).

Primary Mouse Cortical Neuron Culture

Neoortices or hippocampi from mouse pups were removed at postnatal day 0 ($P_0$), digested with 0.4 mg/mL papain and plated onto 24-well glass-bottomed plates pre-coated with 1:30 Matrigel at a density of 65,000 cells per well. Cultured neurons were maintained in Neurobasal-A medium containing 1.25% FBS, 4% B-27 supplement, 2 mM Glutamax and 2 mg/ml fluorodeoxyuridine, and kept in a humid culture incubator with 5% $CO_2$ at 37° C.

smFISH

Stellaris ShipReady smFISH probes of mouse Gapdh with Quasar 570 were purchased from LGC Biosearch Technologies (SMF-3002-1). smFISH experiments were performed according to the manufacturer's protocols for adhesive cell and frozen mouse brain tissue.

STARmap Probe Design

SNAIL probes were designed as follows: (1) the consensus cDNA sequence (CCDS) of all mouse proteins was downloaded from ncbi.nlm.nih.gov/pub/CCDS/current_mouse, and the reference transcriptome was downloaded from cse.ucsc.edu/goldenPath/mm10/bigZips. For genes with multiple transcript isoforms, only the shortest isoforms were considered; (2) Picky 2.2 (32 bit) was used to design the hybridization sequence of each probe pair with length restriction of 40-46 nucleotide; 4 sequences for each gene were designed; (3) the resulting complementary DNA (cDNA) sequences (40-46 nt) were split into halves of 20-25 nt, with an 0-2 nt gap in between, and with the best match of melting temperature (Tm) between the two halves. All the probes were under 60 nt and manufactured as 96-well plates by Integrated DNA Technologies (IDT). For the 160-transcript experiments, the homemade sequencing reagents included six reading probes (R1 to R6) and sixteen 2-base encoding fluorescent probes (2base_F1 to 2base_F16) labeled with Alexa 488, 546, 594 and 647. For the 28-transcript large-volume experiment, all SNAIL primer probes were ordered with Acrydite modification, and the sequencing was carried out using 11-nt orthogonal reading probes (OR1 to OR7) and four 1-base fluorescent probes (1base_F1 to 1base_F4). All sequences provided on the publisher site as an Excel data file.

STARmap Procedure for Cell Culture and Thin Tissue Sections

Sample Preparation

Glass-bottom 12- or 24-well plates were treated by methacryloxypropyltrimethoxysilane (Bind-Silane). For brain-tissue slices, 12-well plates were further treated with poly-L-lysine solution. #2 Micro coverglasses (12 mm) were pretreated with Gel Slick for later polymerization following manufacturer's instruction. Primary neuron cell cultures were fixed with 1.6% PFA in PBS for 10 min then transferred to pre-chilled (−20° C.) methanol and kept at −80° C. for at least 15 min (and up to 1 wk). For brain-tissues, freshly harvested mouse brains were immediately embedded in O.C.T. and snap-frozen. Tissues were either stored at −80° C. or transferred to the cryostat and cut as 16-µm slices. Slices containing primary visual cortex were mounted in the pretreated glass-bottom plates. Brain slices were fixed with 4% PFA in PBS at r.t. for 10 min, permeabilized with −20° C. methanol and then placed at −80° C. for 15 min before hybridization.

Library Construction

SNAIL probes were dissolved at 100 or 200 µM in ultrapure RNase-free water and pooled. The probe mixture was heated at 90° C. for 2 to 5 min and then cooled down at r.t. The samples were taken from −80° C. and equilibrated to r.t. for 5 min, washed by PBSTR (0.1% Tween-20, 0.1 U/µL SUPERase·In in PBS) for 2-5 min and incubated in 1× hybridization buffer (2×SSC, 10% formamide, 1% Tween-20, 20 mM RVC, 0.1 mg/ml salmon sperm DNA and pooled SNAIL probes at 100 nM per oligo) in 40° C. humidified oven with gentle shaking overnight. The samples were then washed for 20 min, twice, with PBSTR, followed by one 20 min wash in 4×SSC dissolved in PBSTR at 37° C. Finally, the sample was briefly rinsed with PBSTR once at r.t. The samples were then incubated for two hours with T4 DNA ligation mixture (1:50 dilution of T4 DNA ligase supplemented with 1×BSA and 0.2 U/µL of SUPERase-In) at room temperature with gentle agitation. Then samples were washed twice with PBSTR, incubated with RCA mixture (1:50 dilution of Phi29 DNA polymerase, 250 µM dNTP, 1×BSA and 0.2 U/µL of SUPERase-In and 20 µM 5-(3-aminoallyl)-dUTP) at 30° C. for two hours under agitation. The samples were next washed twice in PBST (PBSTR omitting SUPERase·In) and treated with 20 mM Acrylic acid NHS ester in PBST for two hours at r.t. The samples were briefly washed with PBST once, then incubated with monomer buffer (4% acrylamide, 0.2% bis-acrylamide, 2×SSC) for 30 min at RT. The buffer was aspirated and 10 µL of polymerization mixture (0.2% ammonium persulfate, 0.2% tetramethylethylenediamine dissolved in monomer buffer) was added to the center of the sample, which were immediately covered by Gel Slick coated coverslip and incubated for 1 hour at r.t., then washed by PBST twice for 5 min each. The tissue-gel hybrids were digested with Proteinase K (0.2 mg/ml) at 37° C. for one hour, then washed with PBST three times (5 min each).

Imaging and Sequencing

For single-gene detection, the 19-nt fluorescent oligo complementary to DNA amplicon was diluted at 500 nM in 1×SSC dissolved in PBST and samples incubated at r.t. for 30 min, then washed by PBST three times for 5 min each before imaging. For sequencing, each sequencing cycle began with treating the sample with stripping buffer (60% formamide, 0.1% Triton-X-100) at r.t. for 10 min twice, followed by three PBST washes, 5 min each. The sample was incubated with the sequencing mixture (1×T4 DNA ligase buffer, 1:25 dilution of T4 DNA ligase, 1×BSA, 10 µM reading probe and 5 µM fluorescent oligos) at r.t. for 3 hours. Then the sample was rinsed with washing and imaging buffer (2×SSC and 10% formamide) for three times (10 min) each before proceeding to imaging. DAPI staining was performed following manufacturer's instruction before Cycle 1 and after Cycle 6 for the purpose of registering sequencing images with Nissl staining. Nissl staining was performed after Cycle 6 following manufacturer's instruction for the purpose of cell segmentation. Images were acquired using Leica TCS SP8 confocal microscopy with a 405 diode, white light laser, 40× oil-immersed objective (NA 1.3), with voxel size of 78 nm×78 nm×315 nm.

Thin-Section STARmap Data Processing

All image processing steps were implemented using MATLAB R2017A.

Image Registration

Image registration was accomplished using a three-dimensional fast Fourier transform (FFT) to compute the cross-correlation between two image volumes at all translational offsets. The position of the maximal correlation coefficient was identified and used to translate image volumes to compensate for the offset. All images were registered to the first round of sequencing, first through a global transform across the entire field of view, and then separately for each tile (corresponding to the individual tiled fields of view used by the microscope during image acquisition).

Spot Calling

After registration, individual dots were identified separately in each color channel on the first round of sequencing. For the 160 gene experiment, dots of approximately 7 pixels in diameter were identified by first filtering the volume with a three-dimensional Laplacian of Gaussian filter, and then finding local maxima in 3D. For the 1020 gene experiment, dots were found using a similar approach but in which the Laplacian of Gaussian was computed at multiple scales and the maxima was found across these scales. After identifying each dot, the dominant color for that dot across all four channels was determined on each round in a 3×3×1 voxel volume surrounding the dot location.

Barcode Filtering

Dots were first filtered based on quality score. The quality score quantified the extent to which each dot on each sequencing round came from one color rather than a mixture of color. The barcode codebook was converted into color-space, based on the expected color sequence following 2-base encoding of the barcode DNA sequence. Dot color sequences that passed the quality threshold and matched sequences in the codebook were kept, and identified with the specific gene that that barcode represented; all other dots were rejected. The high quality dots and associated gene identities in the codebook were then saved out for downstream analysis.

2D Cell Segmentation

Nuclei were manually identified from a maximum intensity projection of the DAPI channel following the final round of sequencing. Cell bodies were first identified using a Random Forests classifier implemented in Ilastik, based on Nissl staining. The classifier was trained on a randomly selected subset of cropped regions from all samples, and then applied to the full image. The thresholded probability map was then pixel-dilated to fill in remaining holes. Finally, a marker-based watershed transform was then applied to segment the thresholded cell bodies based on the combined thresholded cell body map and identified locations of nuclei. A convex hull was computed around each cell body. Points overlapping each convex hull in 2D were then assigned to that cell, to compute a per-cell gene expression matrix.

Single-Cell Data Preprocessing

All single-cell analyses were implemented using a custom software package in Python for the analysis of STARmap experiments. The per-cell expression matrix was first normalized for the expression value Eij across all genes j for each cell i with the formula:

$$N_{ij} = \ln(1 + \text{median}(E_{i.}) * (E_{ij}/\Sigma E_{i.}))$$

For clustering, effects relating to the number of transcripts per cell, the identity of the sample, and the experimental condition (light vs dark) were regressed out using the linear model:

$$E_{ij} = n\text{Spots}_i + \text{exptID}_j + \text{exptCond}_j, \text{ with the assumption that } E_{ij} \text{ is Poisson distributed.}$$

Top-Level Single-Cell Clustering

After normalization and scaling, principal-components analysis was applied to reduce dimensionality of the cellular expression matrix. Based on the explained variance ratio, the top PCs were then used for top-level clustering, based on manual analysis of the explained variance ratio per PC. The top PCs were then clustered using the shared nearest neighbor (SNN) algorithm with Louvain distances. Clusters enriched for the excitatory neuron marker Slc17a7 (vesicular glutatamate transporter), inhibitory neuron marker Gad1, and non-neuronal marker Mqp were manually merged to form three major clusters representing these cell types. The cells were displayed using the Uniform Manifold Approximation and Projection (UMAP) (github.com/lmcinnes/umap). The cells for each cluster were then subclustered using PCA decomposition followed by Louvain SNN clustering to determine specific cell types.

Single-Cell Subclustering

The inhibitory, excitatory, and non-neuronal clusters were then subclustered using the same approach as applied to the major clusters.

Differential Expression Analysis

Genes specifically variable in this subcluster were selected by computing the P value of differential expression of each gene between each cluster and all other clusters, using a bimod test (likelihood-ratio test). The P values were FDR corrected based on the number of clusters.

STARmap Procedure for Thick Tissue Sections

Sample Preparation

Glass-bottom 12-well plates and micro coverglass (12 mm) were pretreated the same as for thin tissue sections. The mice were perfused with PFA, post-fixed on ice for 2-3 hours, transferred to PBS on ice for 30 min, and cut as 150-μm slices. The slices containing primary visual cortex were transferred into the pretreated glass-bottom plates and washed once with ice-cold PBS.

Library Construction

The samples were precleared with −20° C.-chilled methanol at 4° C. for 1 hour, then incubated in 1× permeabilization and hybridization buffer (2×SSC, 10% formamide, 1% Triton-X-100, 20 mM RVC, 0.1 mg/ml salmon sperm DNA and pooled SNAIL probes at 100 nM per oligo, and 0.2% SDS) in 40° C. humidified oven with gentle shaking for two days. The methanol treatment protects samples from expansion and deformation; for co-detection of protein and RNA (Thy1-YFP), methanol preclearance was skipped. The samples were then washed with PBSTV (0.1% Triton and 2 mM RVC) at 37° C. twice for 1 hour each, then PBS once for another hour. The samples were next incubated with polymerization mixture I (4% Acrylamide, 0.2% bis-acrylamide, 2×SSC, 0.5% VA-044) for 1 hour at 4° C. The buffer was aspirated and 40 μL of polymerization mixture II (0.1% ammonium persulfate, 0.1% tetramethylethylenediamine dissolved in polymerization mixture I) was added to the center of the samples, which were immediately covered by Gel Slick coated coverslip and incubated for 1 hour at 40° C. The samples were then washed by PBSTV twice for 20 min each. The tissue-gel hybrids were digested with Proteinase K (0.2 mg/ml in 2×SSC, 1% SDS) at 37° C. overnight, then washed with PBSF (2 mM PMSF in PBS) and PBSTR twice times (30 min each). The samples were next incubated for 12 hours with T4 DNA ligation mixture (1:50 dilution of T4 DNA ligase supplemented with 1× BSA and 0.2 U/μL of SUPERase-In) at room temperature with gentle agitation. Then the samples were washed twice with PBSTR (1 hour each), then incubated with RCA mixture (1:50 dilution of Phi29 DNA polymerase, 250 μM dNTP, 1×BSA and 0.2 U/μL of SUPERase-In and 20 μM 5-(3-aminoallyl)-dUTP) at 30° C. for 12 to 24 hours. Finally, the samples were crosslinked by BSPEG9.

Imaging and Sequencing

The samples were first stained with DAPI overnight then rinsed by PBS for 1 hour. Each cycle began with treating the sample with stripping buffer (60% formamide, 0.1% Triton-X-100) at r.t. for 20 min twice, followed by three PBST washes, 20 min each. The sample was incubated with large volume sequencing mixture (1×T4 DNA ligase buffer, 1:50 dilution of T4 DNA ligase, 1×BSA, 5 μM orthogonal reading probe and 400 nM 1-base fluorescent oligos) at r.t. for 4 hours. Then the sample was rinsed with PBS twice (20 min each) before proceeding to imaging. Images were acquired using Leica TCS SP8 confocal microscopy with a 405 nm diode, white light laser, and 25× water-immersion objective (NA 0.95), with voxel size of 0.9 μm×0.9 μm×1 μm.

Large-Volume STARmap Data Processing

Image Registration 3D FFT registration was again applied, except using the DAPI channel for registration. Specifically, the DAPI channel on each round was registered to the first round globally, and then piece-wise in a 4×5 grid corresponding to the field-of-view tiles used to acquire the image.

Cell Finding and Quantification

After registration, cells were identified using minima of a Laplacian-of-Gaussian filter applied to the DAPI channel.

To quantify the expression of each gene, the average intensity in each color channel was averaged in a 10×10×3 voxel volume around each nucleus.

3D Cellular Analysis

Cells were first clustered into inhibitory, excitatory, and non-neuronal using Gad1, Slc17a7, and several non-neuronal genes using K-means clustering. Each cluster was then subclustered using K-means clustering. The initial values of the K-means clustering were set to the average expression of each marker genes. To compute distances between cell types, the nearest-neighbor distance was computed between cells in all excitatory neurons and each inhibitory neuron subtype, using a kD-tree for fast nearest neighbor computations with Euclidean distance.

Actb Spike-In to Evaluate the Physical Limits of STARmap

The 100 and 1000 genes all shared a common 18 nt sequence (sequence A) in the padlock which would be amplified in the final nanoballs. Another set of SNAIL probes were designed for Actb with a different 18 nt sequence (sequence B). The SNAIL probes of Actb and those of 0, 100, or 1000 genes were mixed together and used in the hybridization. Both the Actb spike-in and 100 & 1,000 genes had gone through the same ligation and amplification step to ensure equal efficiency. For readout, two fluorescent detection oligos (Alexa488-probes complementary to sequence B and Alexa 647-probes targeting sequence A) were added to the samples; the amplicons of Actb and amplicons of the rest of the genes were be imaged in two separate channels. The amplicons of Actb RNA were then tested to determine whether the number of amplicons would be diluted by increased numbers of other genes, as an indication of molecular crowding (FIG. 16A-16E).

Immunostaining of CLARITY Tissue

PFA fixed tissue was processed as described previously in Shendure et al (2005). Briefly, 200 µm thick PFA fixed brain sections were placed in a 1% acrylamide embedding solution at 4° C. for 23 hours, embedded at 37° C. for 4 hours, and then passively cleared for 5 days. Cleared sections were washed in PBST for 2 days, stained with anti-NeuN (1:100) for 24 hours at RT, and then washed for 24 hours in PBST. Sections were imaged using confocal microscopy.

Devices for Automated In Situ Sequencing (Prophetic)

The automated steps of the experimental procedure would include three buffers that are kept at room temperature in larger volumes: 1) wash buffer, 2) imaging buffer, and 3) strip buffer. A tube of ligase enzyme mixture will be kept at 4° C. There will be 8 tubes containing fluorescently labeled imaging materials, also kept at 4° C. Six of the tubes will contain fluorescently labeled oligonucleotides and probes for hybridization. One of the tubes will contain small molecule Nissl stain and one will contain small molecule DAPI stain. If it is not possible to mix the ligase and oligos at the time of imaging, they can potentially be premixed and kept at 4° C.

The sequencing process includes a sample mounted in the custom imaging chamber and connected to fluidics. On each of the six rounds, the ligase mixture, the ligase mixture and one of the 6 oligonucleotide mixtures will need to be mixed (200-400 µl total volume), and then applied to the sample for 3 hours. Next, wash buffer will be flowed over the sample for 10 min. The wash buffers will then be exchanged with imaging buffer. The system will then send a trigger to the microscope, which will perform fluorescence imaging. After imaging is complete, the microscope will send a trigger to the system to start the next round. The system will flow stripping buffer over the sample for 10 min. Wash buffer will be flowed for 5 min to remove residual stripping buffer. The next round of ligase and fluorescently labeled oligos will be applied. After repeating this process six times, the laser round will be stripped and washed, and then the Nissl and DAPI solutions will be applied at the same time for an hour. This will then be washed and imaged in imaging buffer. Finally, after the experiment is complete, the whole system should be flushed with bleach to clean it out for the next run.

The computer-controlled fluidics pump the various solutions, mix the ligase and oligo solutions, and select which oligo solution is used on each round. All of the parameters (flow speed, time, etc.) in this sequence should be programmable.

Figure 24A:
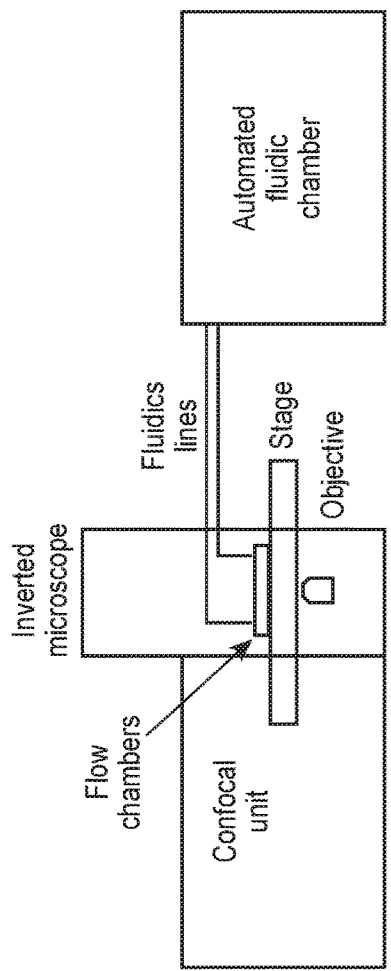
FIG. 24A-24B depict a graphic layout of an exemplary fluidics system used to perform the methods described herein.
Figure 24B:
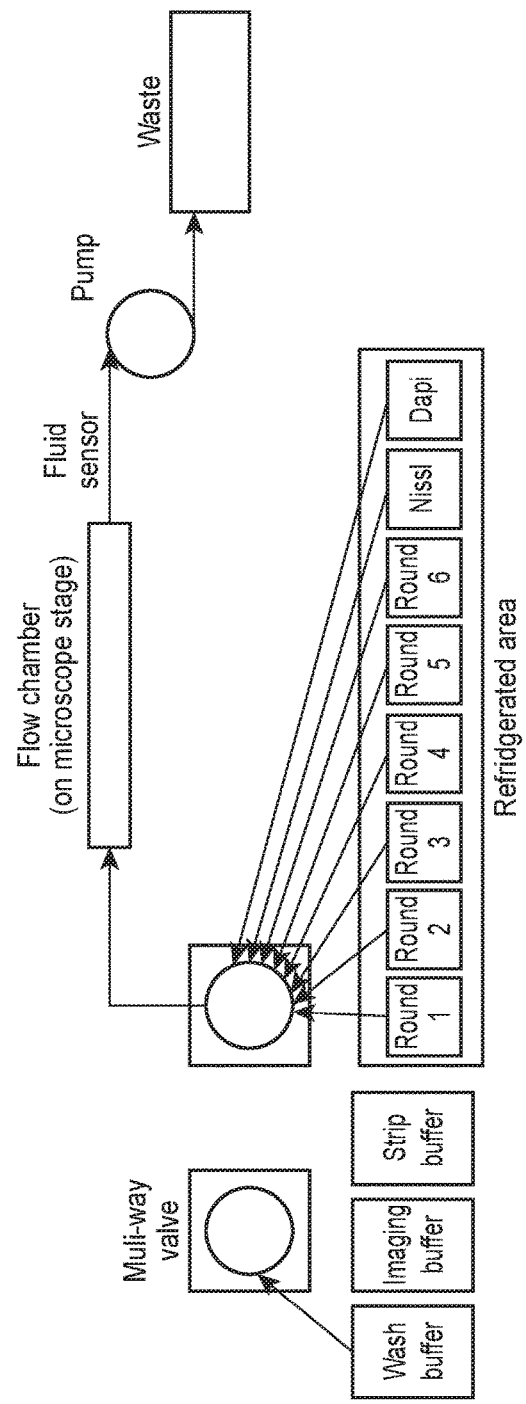

For all of this, a custom imaging chamber holds a section of tissue sealed in a small volume, with an inflow and outflow ports, and adapts to a microscope with a 24 plate holder. FIG. 24A depicts the overall hardware setting for STARmap sequencing and FIG. 24B depicts a design of an exemplary fluidic system described herein.

Results

Example 1

STARmap

The methods disclosed herein including the in situ sequencing technology enabled highly-multiplexed gene detection (up to 1000 genes) in intact biological tissue. The methods began with raw biological tissue (fresh or preserved, as little as one-cell or as large as millimeter(s) in size) and resulted in output image-based gene quantification at subcellular and cellular resolution and with high efficiency, low error rate, and fast processing time.

Figure 2A:
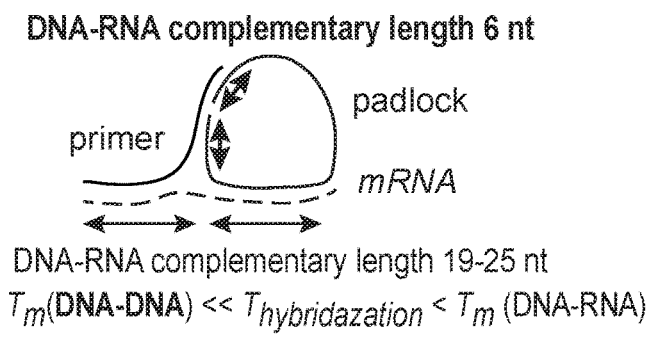
FIG. 2A-2I depict Specific Amplification of Nucleic Acids via Intramolecular Ligation (SNAIL) probes for high-quality RNA imaging and mouse brain instantiation.

A schematic diagram of STARmap as described herein was depicted in FIG. 1A. After the brain tissue was prepared (see Methods for mouse brain protocols), the custom SNAIL probes (FIG. 2A) that encountered with and hybridized to intracellular mRNAs (dashed lines) within the intact tissue were enzymatically replicated as cDNA amplicons. The amplicons were constructed in situ with an acrylic acid N-hydroxysuccinimide moiety modification and then copolymerized with acrylamide to embed within a hydrogel network (wavy lines), following by clearance of unbound lipids and proteins (FIG. 3A-3F). Each SNAIL probe contained a gene-unique identifier segment which is read-out through in situ sequencing with 2-base encoding for error correction (SEDAL, FIG. 4A-4L). Finally, highly multiplexed RNA quantification in 3D revealed gene expression and cell types in space.

Figure 1C:
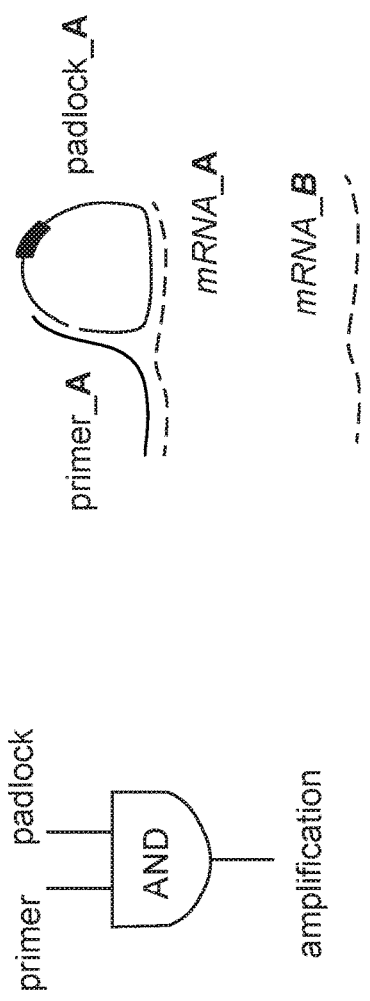
Figure 1D:
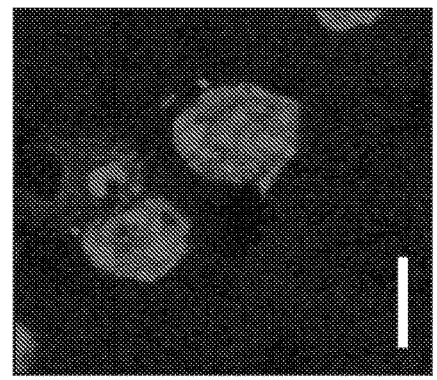
Figure 1D:
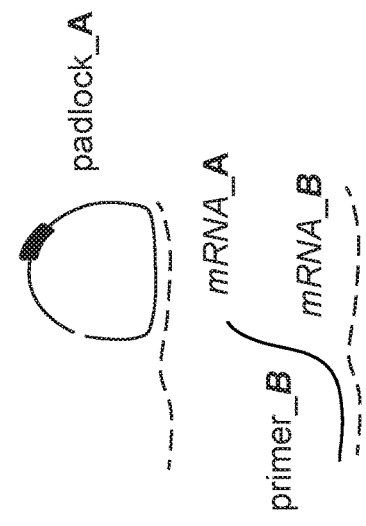
Figure 1E:
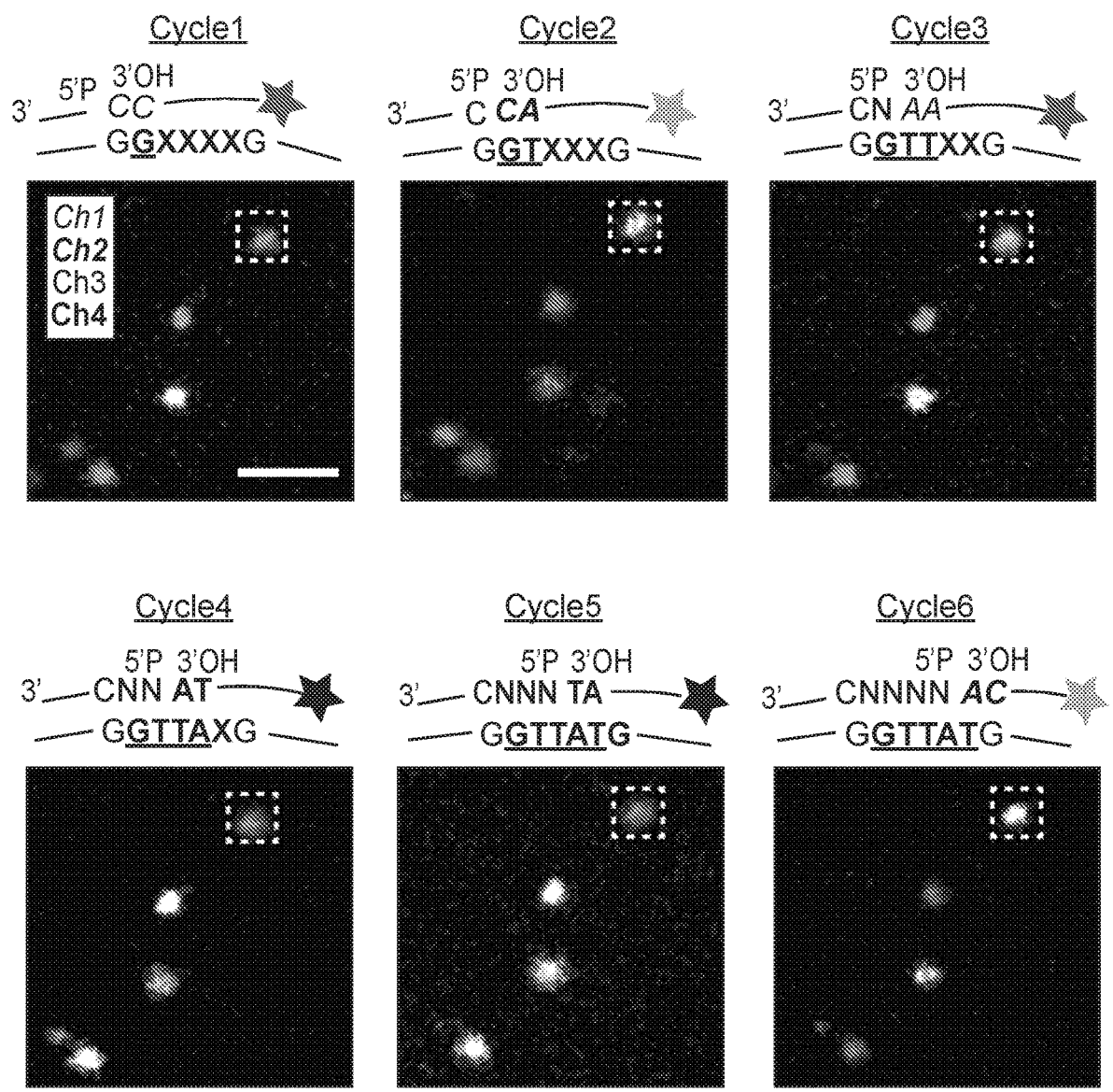

FIG. 1A depicted the following method regarding SNAIL: a pair of primer and padlock probes amplified target-specific signals and excluded noise known to commonly arise from non-specific hybridization of a single probe. FIGS. 1C and 1D depicted that only adjacent binding of primer and padlock probes lead to signal amplification. mRNA A represented Gapdh and mRNA B represented Actb. Both fluorescent images showing Gapdh mRNA and cell nuclei labeling in mouse brain slice; noted the absence of labeling with mismatched primer and padlock (FIG. 1D, right). Scale bar indicated 10 µm. FIG. 1E depicted in situ sequencing of DNA amplicons in the tissue-hydrogel complex via SEDAL, an improved sequencing-by-ligation method devised for STARmap. For each cycle, the reading probes (line without star-symbol label) contained an incrementally increasing-length run of degenerate bases (N representing an equal mixture of A, T, C and G) with phosphate at the 5' end (5'P) to set the reading position; the decoding probes (line with star-symbol label) were labeled by fluorophores with color coding for the dinucleotide at the 3' end. The two kinds of probes were ligated to form a stable product with high melting-temperature only if both probes were perfectly complementary to the DNA template (lower sequence), allowing later imaging after unligated probes were washed away. After each imaging cycle, probes were stripped away from the robust tissue-hydrogel using 60% formamide so that the next cycle could begin. X indicated the unknown base to be read; "underline" indicated decoded sequence; Ch1-4 indicated fluorescence channels. The scale bar indicated 2 µm.

Example 2

SNAIL

Reverse transcription may be the major efficiency-limiting step for in situ sequencing, and SNAIL bypassed this step with a pair of primer and padlock probes (FIG. 2A) designed such that only when both probes hybridize to the same RNA molecule. Design of SNAIL probes (one component of STARmap) included the following: each primer or padlock probe (19-25 nucleotides; nt) had a designed $T_m$ (melting temperature of nucleic acids) of 60° C. or higher to hybridize with target RNA, while the complementary sequence between primer and padlock was only 6 nt on each arm with Tm below room temperature, so that primer-padlock DNA-DNA hybridization was negligible during DNA-RNA hybridization at 40° C., but allowed DNA ligation by T4 DNA ligase in the following step.

Figure 2B:
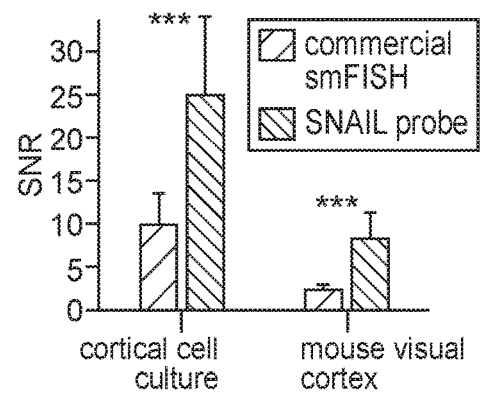
Figure 2C:
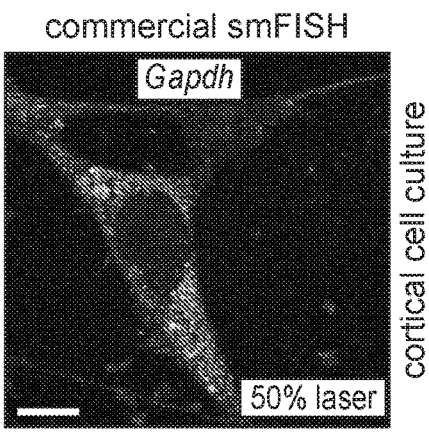
Figure 2D:
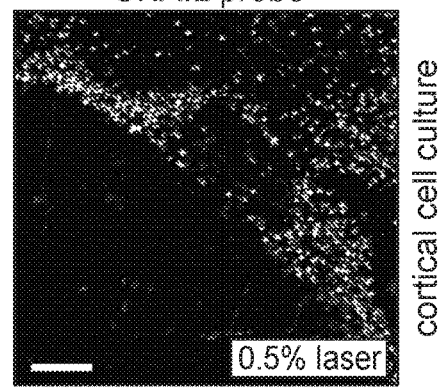
Figure 2E:
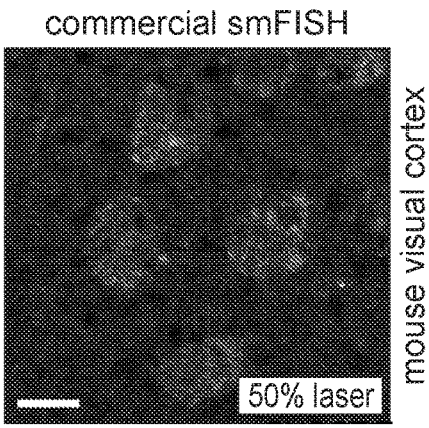
Figure 2F:
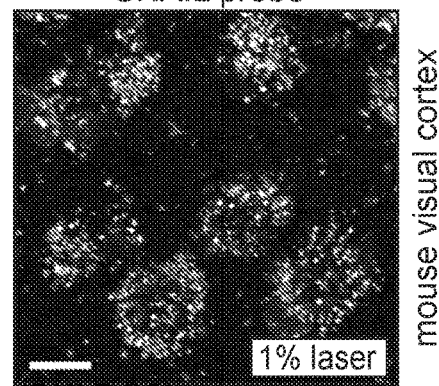
Figure 2G:
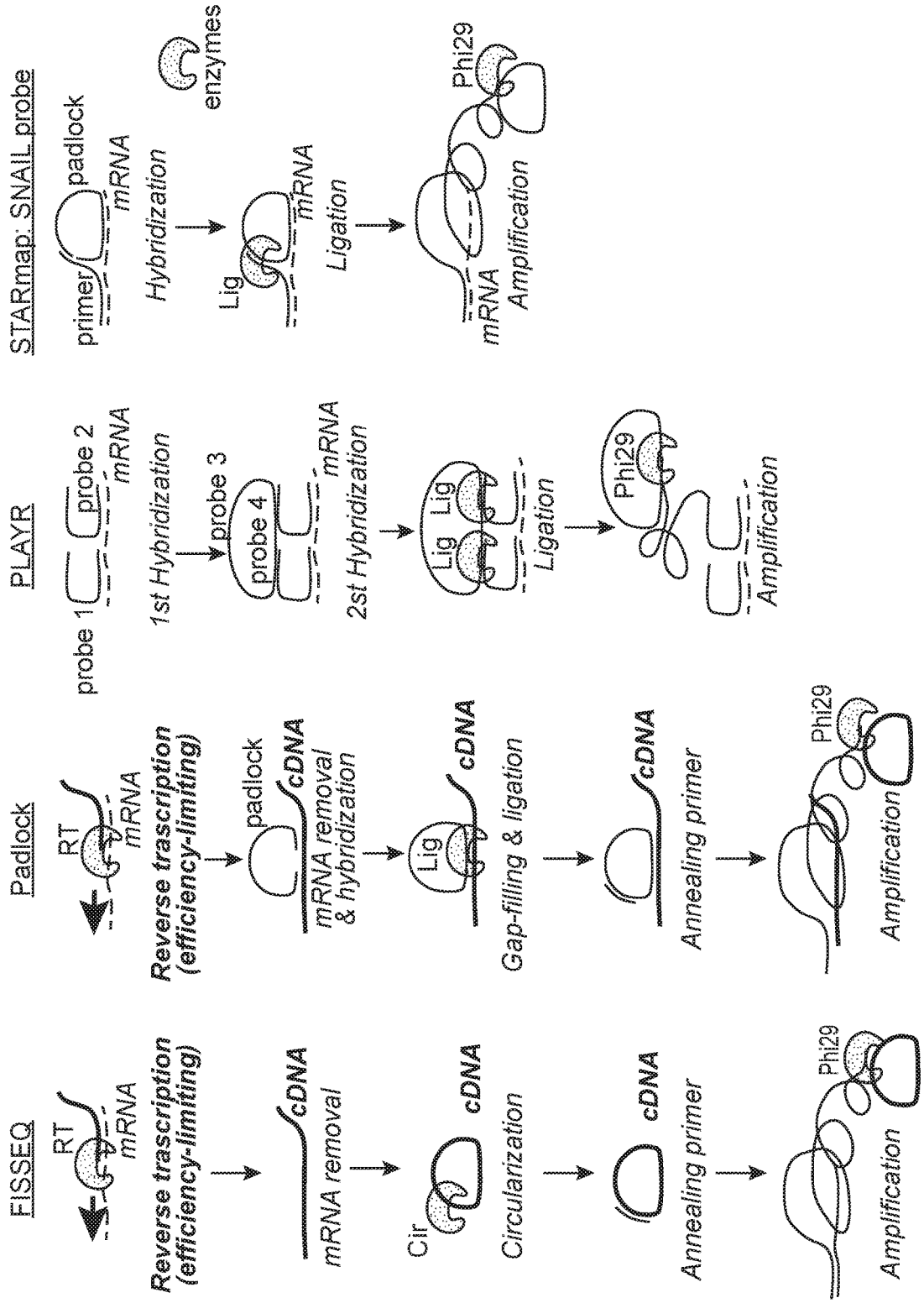
Figures 2H, 2I:
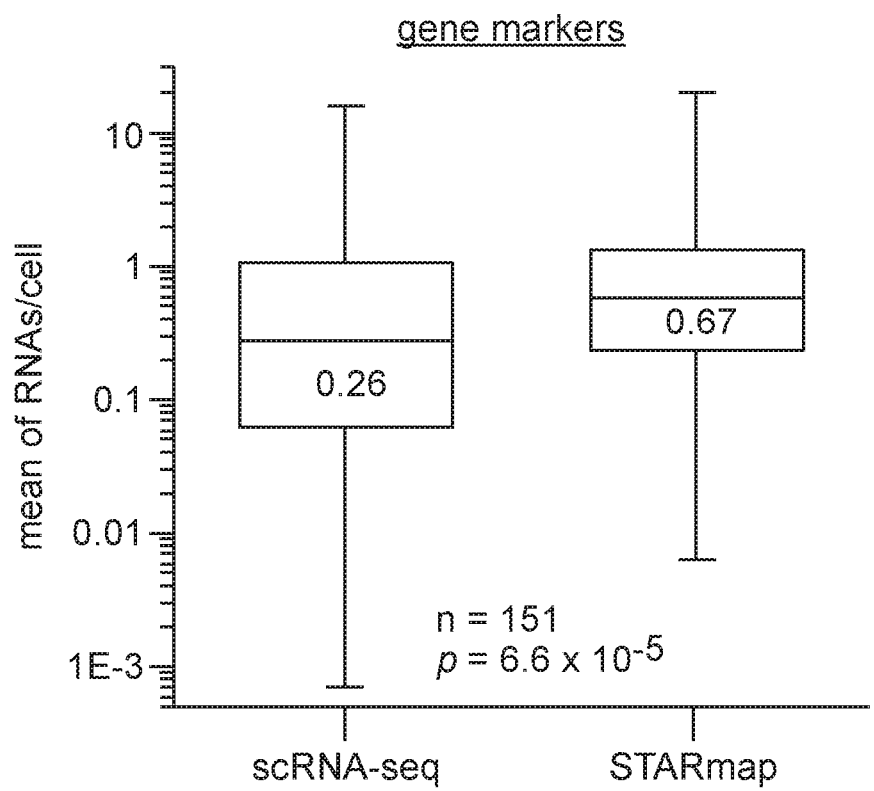

The padlock probe was circularized and rolling-circle amplified to generate a cDNA nanoball (amplicon) containing multiple copies of the cDNA (FIG. 1A-1D). This mechanism ensured target-specific signal amplification and excluded noise that invariably otherwise arose from non-specific hybridization of single probes. Indeed, the outcome was much higher absolute intensity and signal-to-noise ratio (SNR) compared to commercial single-molecule fluorescent in situ hybridization (smFISH) probes (FIG. 2B-2F). FIG. 2B depicted the comparison of signal-to-noise ratios (SNR; mean intensity of signal spots/mean intensity of background) of commercial smFISH probes and SNAIL probes targeting Gapdh mRNAs in mouse cortical cell cultures and mouse visual cortex sections. Error bars indicated standard deviation (s.d.) of spot intensity. Error bars represented s.d. of 39,398 pixels; 30,297 pixels; 97,555 pixels; and 19,392 pixels corresponding to RNA signals out of 640,000 pixels in acquired images; ***P<0.0001, Student's t-test. FIG. 2C-2F depicted fluorescence images of Gapdh smFISH (FIGS. 2C and 2E) and SNAIL probes (FIGS. 2D and 2F) in cortical cell cultures (FIGS. 2C and 2D) and visual cortex sections (FIGS. 2E and 2F); scale bars indicated 10 µm. FIG. 2G depicted a comparison of multiplexed RNA imaging methods using rolling circle amplification (RCA). In comparison with FISSEQ and padlock probes, SNAIL probes have overcome the efficiency-limiting step of reverse transcription and greatly simplified the experimental procedure; while PLAYR requires four probes, one additional step and two ligation sites, SNAIL only requires a pair of probes and one ligation site. Boxplots of RNAs per cell of 151 cell type gene markers were measured by single-cell RNA sequencing (scRNA-seq, ref) and STARmap (extracting from 160-gene mapping of visual cortex) (FIG. 2G). The box plot depicted the first and third quartiles; middle line as the median; whiskers as the 5% and 95% data points; P value as the rank-sum test. A summary of single-cell RNA sequencing and RCA-based multiplexed RNA detection methods, numbers were extracted from references (FIG. 2I).

Example 3 cDNA Amplicon Embedding in the Tissue-Hydrogel Setting

Figure 3D:
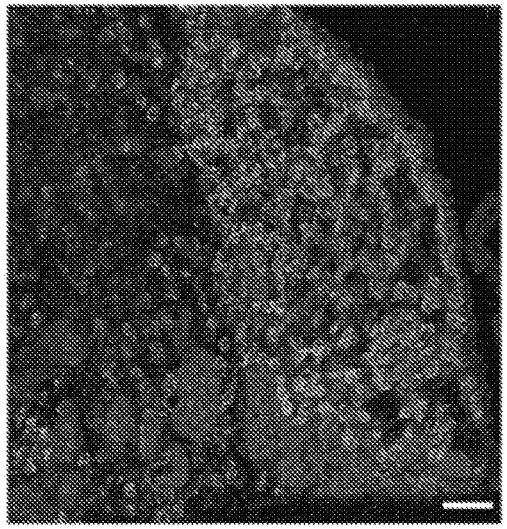
Figure 3E:
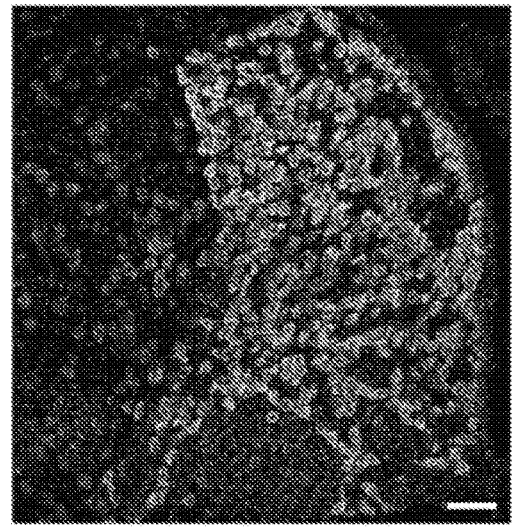
Figure 3F:
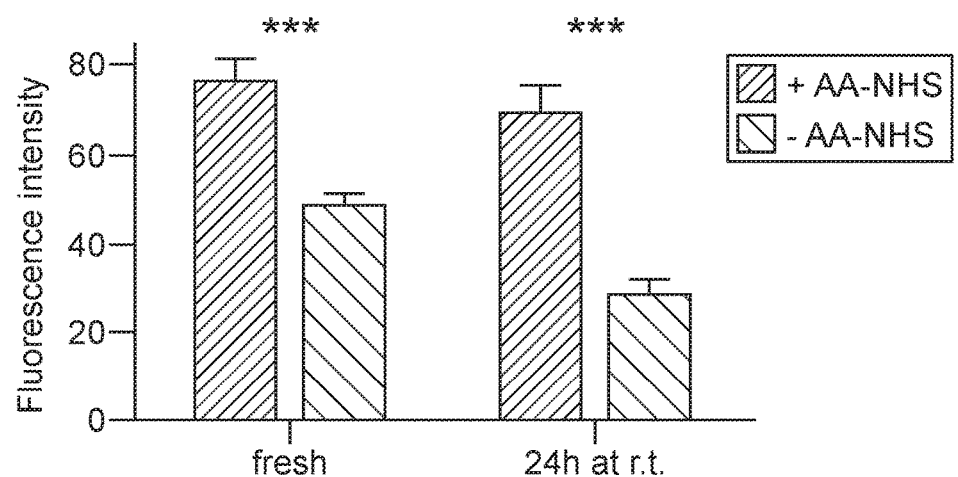
Figure 3G:
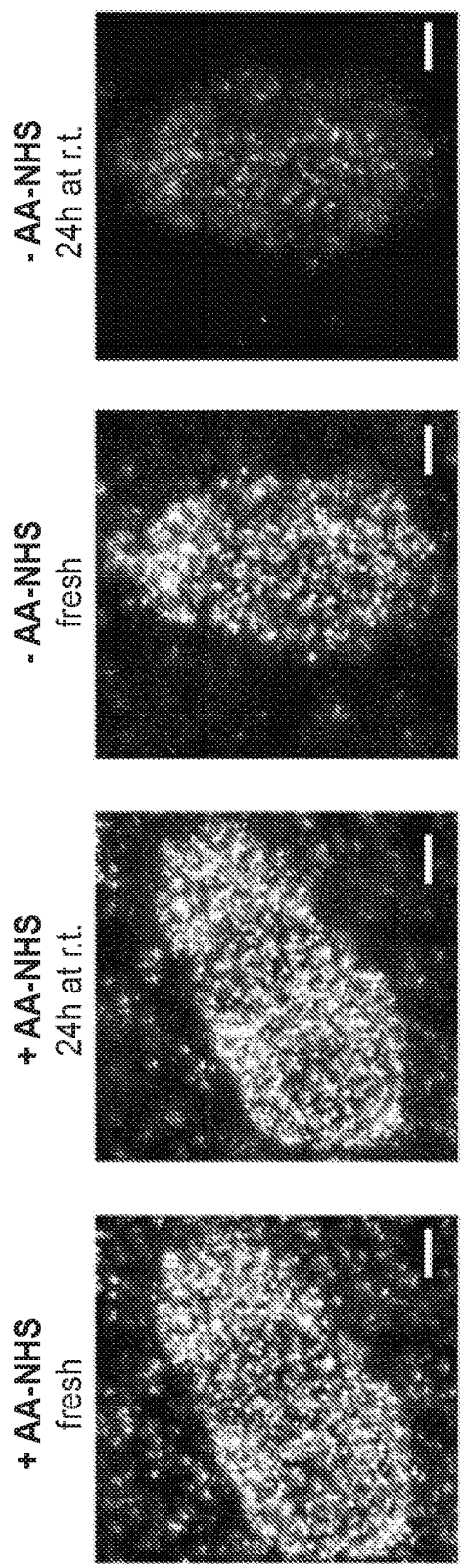

To enable cDNA amplicon embedding in the tissue-hydrogel setting, amine-modified nucleotides were spiked into the rolling circle amplification reaction, functionalized with an acrylamide moiety using acrylic acid N-hydroxysuccinimide esters, and copolymerized with acrylamide monomers to form a hydrogel (FIG. 1A, FIG. 3A). A schematic diagram of hydrogel-tissue chemistry for STARmap in thin tissue slices was depicted in FIG. 3A. DNA amplicons were synthesized in the presence of minor levels of 5-(3-aminoallyl)-dUTP, which replaced T at a low rate and allowed further functionalization with the polymerizable acrylamide moiety using acrylic acid N-hydroxysuccinimide ester (AA-NHS), so that the DNA amplicons were covalently anchored within the polyacrylamide network at multiple sites (FIG. 3A, right). The resulting tissue-hydrogel was then subjected to protein digestion and lipid removal to enhance transparency (FIG. 3B-3E). Fluorescence images (summed intensity from all four fluorescent channels) represented 160-gene detection in mouse visual cortex (FIGS. 3B and 3C) and 16-gene detection in mouse medial habenula (FIGS. 3D and 3E). Compared to untreated samples (FIGS. 3B and 3D), samples treated with 5-(3-aminoallyl)-dUTP HTC and clearing of lipids and proteins (FIGS. 3C and 3E) showed reduced opacity and autofluorescence. Scale bars indicated 50 µm. DNA-gel crosslinking maintained DNA amplicons in the gel. 160-gene samples were prepared with or without AA-NHS and imaged within medial prefrontal cortex (FIG. 3F-3G). Fresh samples prepared without AA-NHS had 36% signal loss compared to AA-NHS treated samples and had suffered from further 40% signal loss after stored at room temperature for 24 hours, while AA-NHS treated sample only had 9% signal change (FIG. 3F). Fluorescence intensities were the mean of four technical replicates with the imaging dimension of 120 µm×120 µm×3 µm. Error bar showed mean±s.d.; ***p<0.001, two-sided t-test. Fluorescence images were depicted in FIG. 3G with scale bars of 3.5 µm.

Figure 3H:
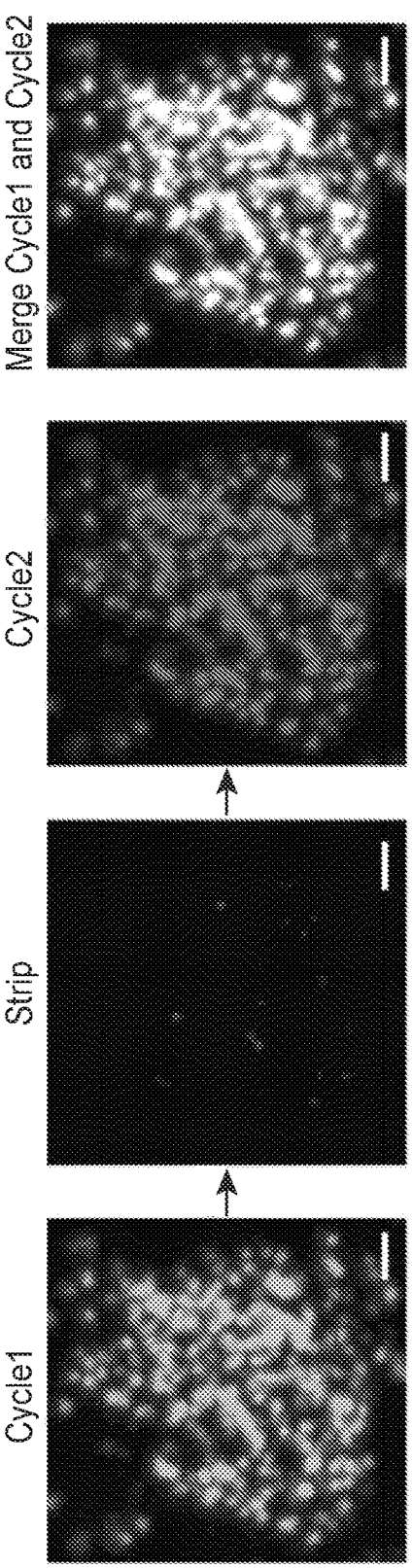

Since this design chemistry dictated that amplicons were covalently linked with the hydrogel network, the position and shape of the targets were maintained through many cycles of detection. FIG. 3H depicted zoomed-in fluorescence images of one neuron in visual cortex detecting Gapdh RNA by STARmap for Cycle 1, stripping, Cycle 2 and merged images of Cycle 1 and Cycle 2, demonstrating stable spatial position of DNA amplicons over sequencing cycles. Scale bars indicated 2 µm.

Example 4

SEDAL

A 5-base barcode (library size of 1,024) was designed and built into each padlock probe as a gene-unique identifier to be sequenced, thus enabling multiplexed gene detection (FIG. 1A). Sequencing-by-synthesis paradigms were avoided as these required elevated reaction temperatures, which in turn were problematic for imaging and sample stability in comparison to sequencing-by-ligation methods that were implemented at room temperature. However, none of the reported or commercially available sequencing-by-ligation methods approach the necessary SNR or accuracy for this challenging intact-tissue application (FIG. 4A-4L).

For this reason, a new approach termed SEDAL was devised specifically for STARmap (FIG. 4A-4L).

A schematic diagram of SEDAL is depicted in FIG. 4A. SEDAL involved a T4 DNA ligase with activity strongly hindered by base mismatches, and two kinds of sequencing probes: reading probes that set the base position to be interrogated, and fluorescent decoding probes that transduced base information into colors for imaging. Unlike other sequencing-by-ligation methods which used pre-annealed reading probes (or equivalent), the reading probe in SEDAL was short (11 nt, with $T_m$ near room temperature), partially degenerate (e.g. as shown in FIG. 4A, for cycle 4, the first two base at 5' end are N, equal amount mixture of A, T, C and G), and mixed with decoding probes and T4 DNA ligase for a one-step reaction. At room temperature, the reading probe remained in a dynamic state of annealing with and detaching from the DNA template. T4 DNA ligase ligated it to the fluorescent 8-nt decoding probe only when the reading probe perfectly matched the DNA template. That is, the two probes ligated to form a stable product for imaging only when a perfect match occurred. The short reading and decoding probes were then washed away, leaving fluorescent 19-nt products stably hybridized to the DNA amplicon for imaging. For the next cycle, previous fluorescent products were stripped and the reading probe included one more degenerate base to shift the reading frame by one base (FIG. 1E). 5'P indicated 5' phosphate. 3'InvT indicated 3' inverted dT base that prevented self-ligation of the reading probe; 3'OH indicated 3' hydroxyl group.

After each cycle corresponding to a base readout, the fluorescent products were stripped by formamide, which eliminated error accumulation as sequencing proceeded (FIG. 1E and FIG. 4B). Comparison of key properties of all sequencing-by-ligation methods were shown in FIG. 4C-4F. Background problems associated with the commercial SOLiD sequencing kit when applied to mouse brain tissue was depicted in FIGS. 4C and 4D while custom SEDAL reagents exhibited minimal background in FIGS. 4E and 4F. Signal images (FIGS. 4C and 4E) represented the first cycle of sequencing for the Malat1, Actb, Calm1 and Snap25 genes. Background images (FIGS. 4D and 4F) were acquired after cleavage/stripping of the first cycle. Scale bars indicated 50 µm.

Schematic diagrams of the 1-base and 2-base encoding paradigms, along with example results with or without a single sequencing error (wrong color) during cycle 3 were depicted in FIGS. 4G and 4H. For 1-base encoding, a single sequencing error led to one base mutation and thus the wrong 5-base code (FIG. 4G). For 2-base encoding, the six-cycle paradigm played an error-reduction role. Since a single error during any sequencing cycle propagated and caused the flanking known base G to mutate into other bases, erroneous reads were rejected (FIG. 4H). A 2-base encoding scheme was designed and implemented to mitigate any residual errors related to imaging high densities of spots (FIG. 4G-4H).

Figure 4K:
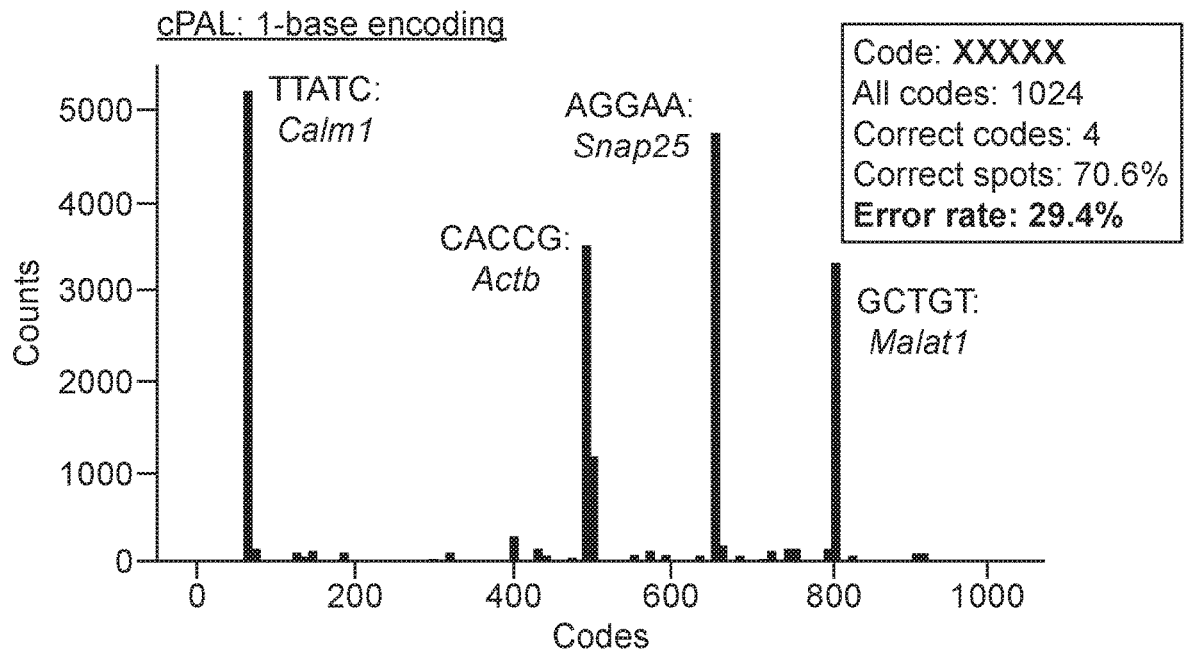
Figure 4L:
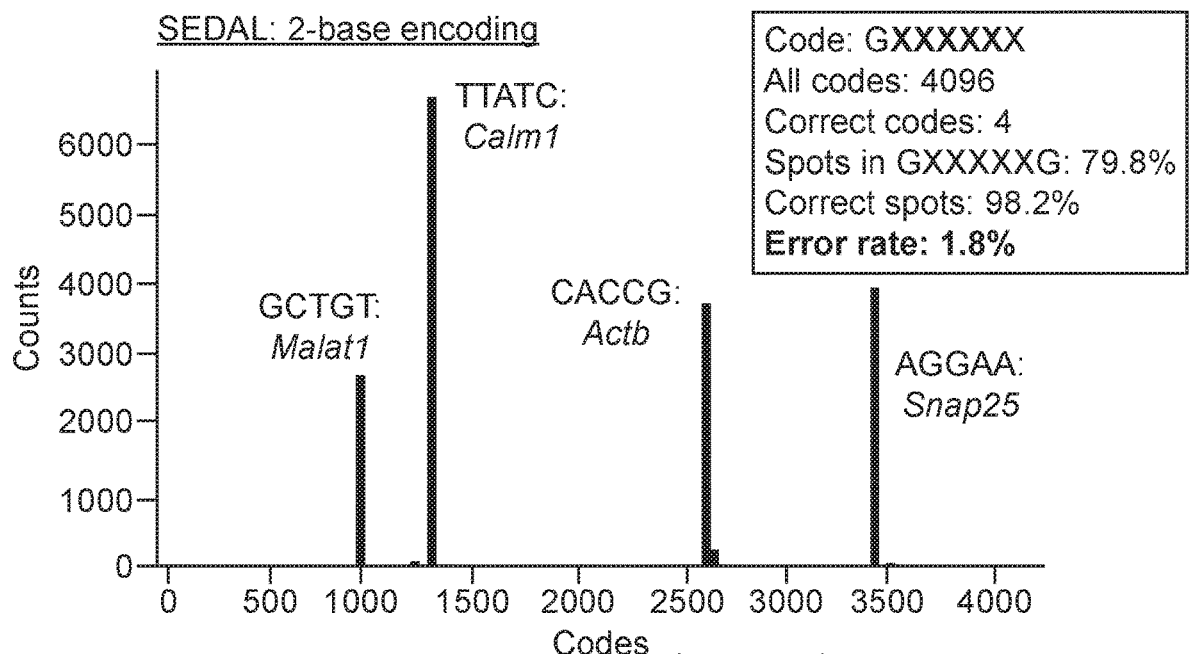

Based on a panel of four highly expressed test genes, the error rate of STARmap was more than an order of magnitude lower than that of prior methods (~1.8% versus 29.4%; FIG. 4I-4L). Actual data from cPAL (representing a 1-base encoding scheme) and SEDAL (representing a 2-base encoding scheme) were applied to 4-gene detection in mouse visual cortex. The SNAIL probes for Malat1, Actb, Calm1 and Snap25 were identical for the two conditions and the Hamming distance for each pair of the four 5-base codes was 5 (i.e. complete non-homology); with such sparse coding, the sequencing error rate was estimated by the percentage of wrong spots (not the four 5-base codes used) out of all detected spots. (FIG. 4I-4J). A spatial map of the four genes detected by cPAL was shown in FIG. 4I and SEDAL was shown in FIG. 4J. The error rate of cPAL in the 4-gene experiment (FIG. 4I) was 29.4% (FIG. 4K) while the error rate of SEDAL (FIG. 4J) was 1.8% after the built-in error reduction (FIG. 4L).

Example 5

Cell Classification of Cell Types in Primary Visual Cortex Using STARmap

To test if STARmap could deliver on the initial goal of high-content 3D intact-tissue sequencing of single-cell transcriptional states with the necessary sensitivity and accuracy, STARmap was applied to a pressing current challenge in neuroscience: detecting and classifying cell types and corresponding tissue-organization principles in neocortex of the adult mouse brain. The anatomy and function of mouse primary visual neocortex has been extensively studied, which allows validation of the results by comparison with prior findings that span multiple papers, methodologies, and data sources, but the full diversity of deeply molecularly-defined cell types within visual cortex has not yet been spatially resolved in a single experiment, which has precluded identification of potentially fundamental joint statistics and organizational principles across 3D volumes. Among many examples of the experimental leverage such information could provide, joint 3D cell-typology mapping was employed to help decode the spatiotemporal logic of neural-activity-triggered gene expression as a function of cell type and spatial location.

Figure 5A:
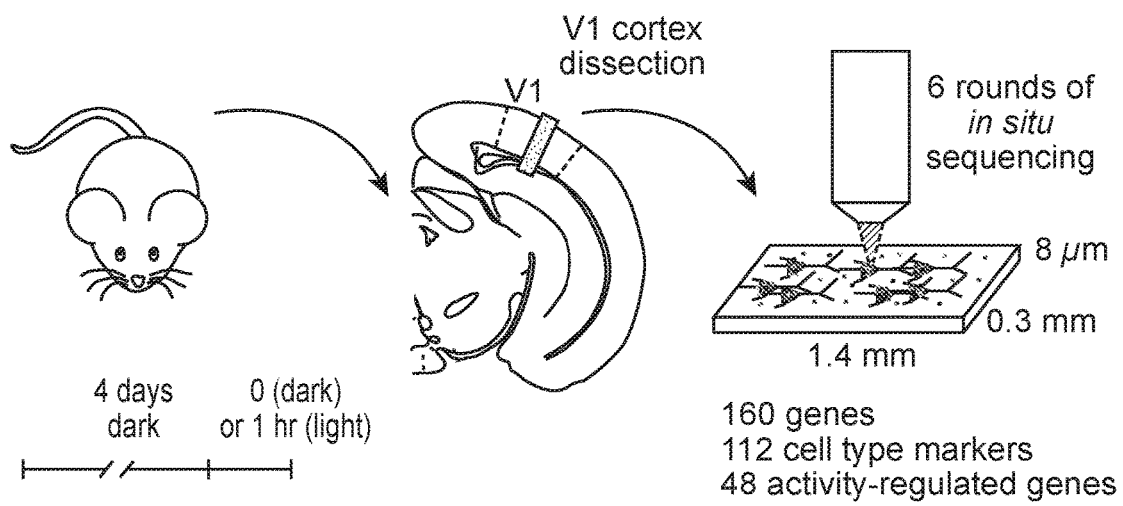
FIG. 5A-5N depict classifying cell types in primary visual cortex using the methods described herein.
Figure 5B:
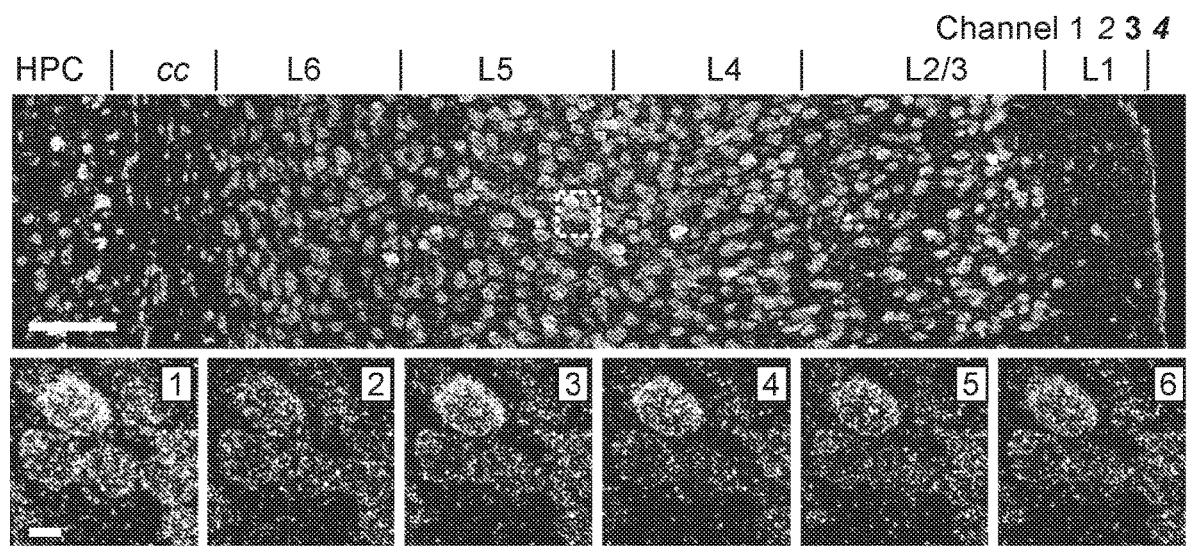

Primary visual cortex (V1) was coronally sectioned and 5-base barcoded SNAIL probes were used over six rounds of in situ SEDAL sequencing in coronal mouse brain slices (FIG. 1A, FIG. 5A-5B) to survey a large curated gene set of 160 genes including 112 putative cell-type markers collated from mouse cortical single-cell RNA sequencing and 48 activity-regulated genes (ARGs). In one arm of the mouse cohorts, visually-evoked neural activity was provided via 1 hr light-exposure after four days of housing in the dark; other mice were kept continuously in the dark prior to sacrifice. 8 µm-thick volumes containing 600-800 cells covering all cortical layers were imaged. FIG. 5B depicted raw fluorescence images of in-process STARmap with the full view of Cycle 1 (FIG. 5B, top) and zoomed views across all six cycles (FIG. 5B, bottom). Full field indicated 1.4 mm×0.3 mm, scale bar indicated 100 µm; zoomed region indicated 11.78 µm×11.78 µm, scale bar indicated 2 µm; channel indicated color code for the four fluorescence channels; L1-6 indicated the six neocortical layers; cc indicated corpus callosum; HPC indicated hippocampus.

Figure 6B:
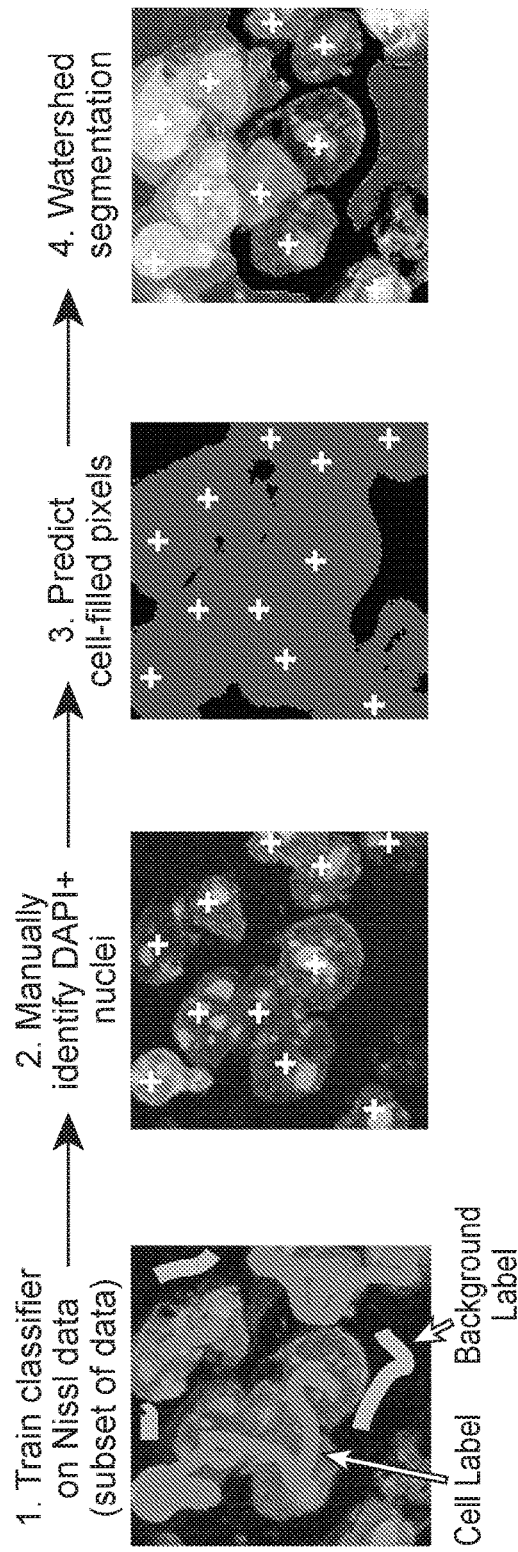

After six rounds of sequencing, fluorescent Nissl staining was used to segment cell bodies, allowing attribution of amplicons to individual cells (FIG. 6A-6B). FIG. 6A depicted a diagram showing processing pipeline to extract decoded reads from raw imaging data (see also Methods for detail corresponding to each step): (1) samples were imaged over multiple rounds; (2) samples were registered across rounds, showing two rounds with a misalignment that must be corrected by registration; (3) spots were automatically identified in each color channel (independently in the first round) as putative amplicons that will be decoded based on the color values at the point in each round; (4) reads were called based on comparing the maximum intensity of each spot in each round across channels with the predicted color sequences for each barcoded DNA sequence (colorspaceencoded barcodes); (5) cells were detected using machine learning-based segmentation that took into account various intensity and texture features in order to segment Nissl containing cells from background (described in (FIG. 6B)); and (6) reads were assigned to cells by computing the overlap between each valid read's position and a convex hull of the segmented area for each cell.

The gene encoded by a read that overlapped with a cell's convex hull was assigned to that cell. FIG. 6B depicted a method for determining cell extents: (1) a random forest classifier (a non-parametric machine learning algorithm for label prediction) was trained on a subsampled set of Nissl-stained data to discriminate cell-containing areas vs. background; (2) cell locations were manually selected using the DAPI (cell nucleus) channel; (3) the classifier was applied to the whole image to predict the location of cells; and (4) cells were segmented from this prediction using marker-based watershed, which segmented the cell-labeled areas of the image into discrete cell bodies based on the known locations of nuclei.

Figure 5C:
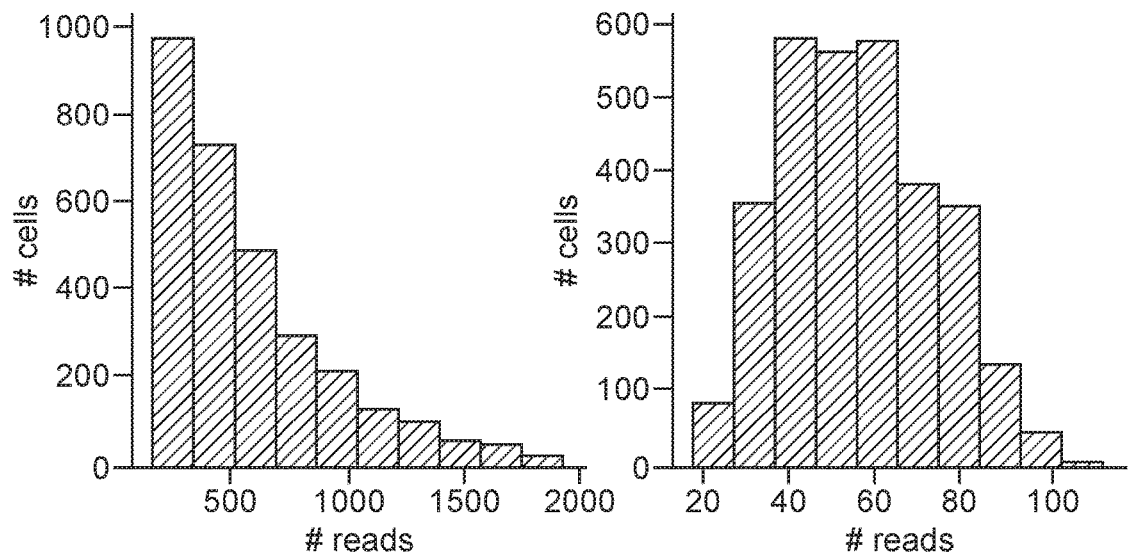
Figure 5D:
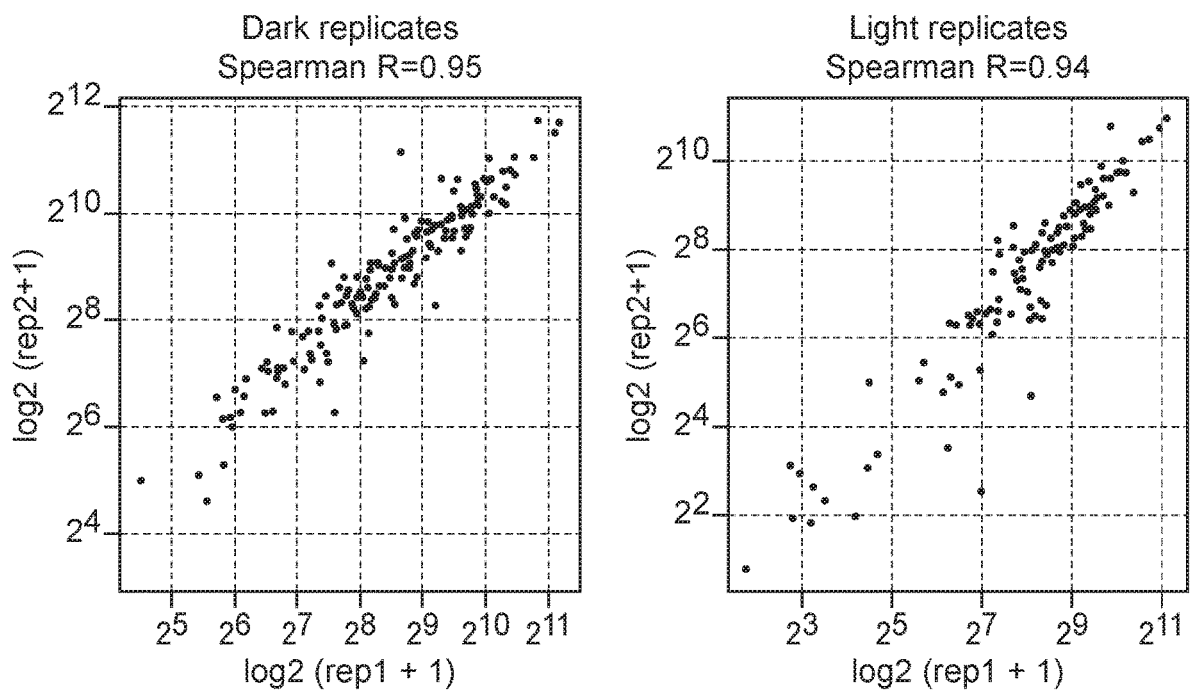

Histograms in FIG. 5C detected reads (DNA amplicons) per cell (FIG. 5C, left), and genes per cell (FIG. 5C, right). The values corresponding to amplicons-per-cell and genes-per-cell varied substantially (FIG. 5C), while the 160-gene expression pattern was consistent between biological replicates (R=0.94-0.95, FIG. 5D), revealing reliable detection of transcript diversity at the single-cell level. Quantitative reproducibility of biological replicates was shown in FIG. 5D, whether in the light or dark condition: $\log_2$ (amplicon quantity) for 160 genes across the whole imaging region plotted. Rep1 indicated expression value in first replicate, rep2 indicated expression value in second replicate.

Figure 5E:
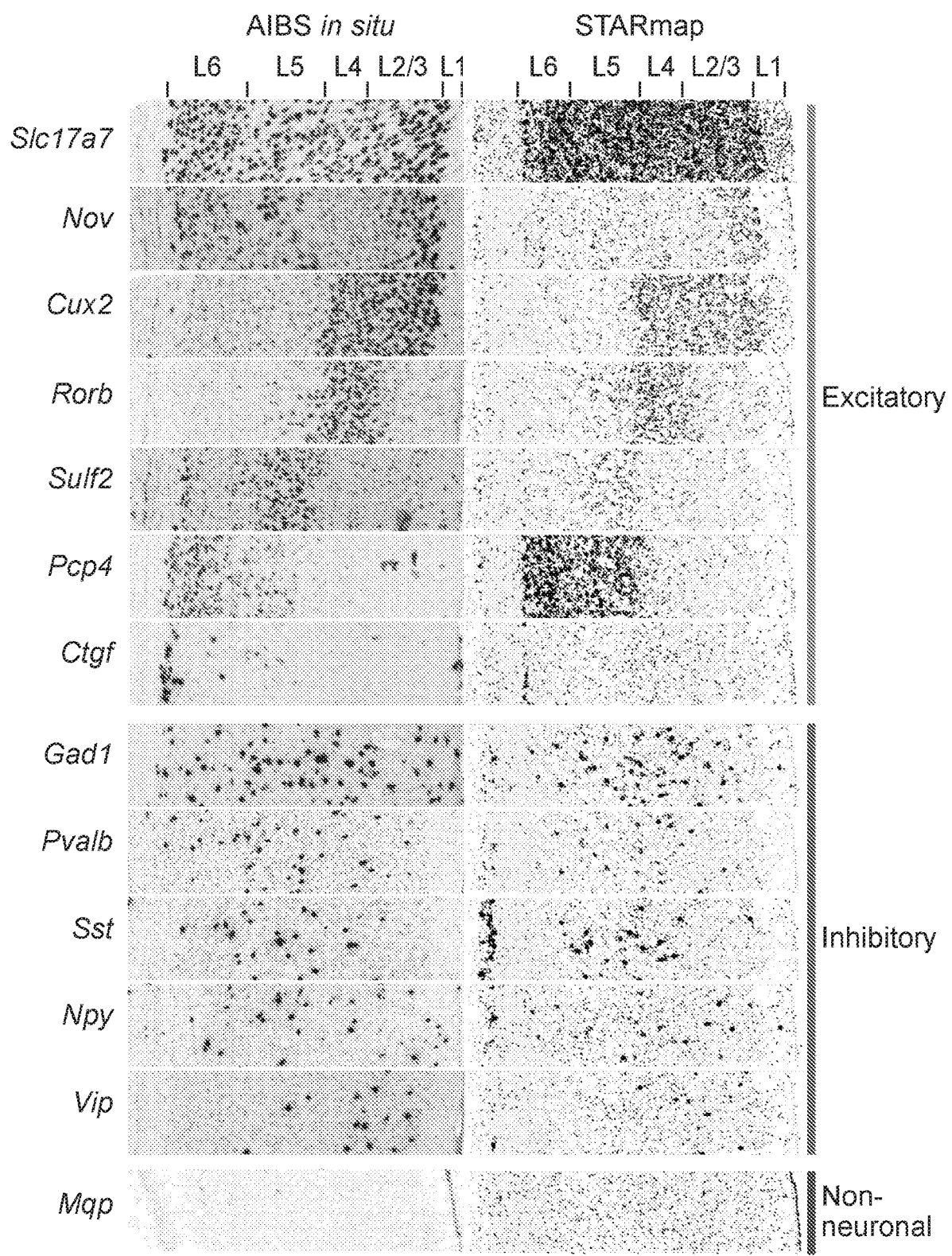

This 160-gene pilot faithfully reproduced the spatial distribution of known cortical layer markers and interneurons, illustrated here via comparison of in situ images from paired public atlases and STARmap results (FIG. 5E). Validation of STARmap shown in FIG. 5E depicted in situ images from Allen Institute of Brain Science (AIBS) (FIG. 5E, left column) and RNA pattern of individual genes extracted from 160-gene STARmap, which reliably reproduced the spatial gene expression pattern from AIBS (FIG. 5E, right column).

Figure 5F:
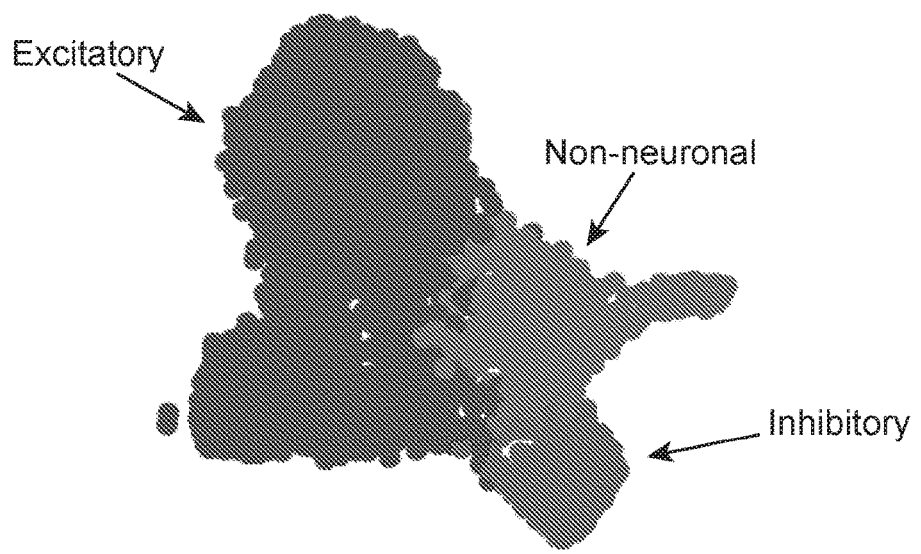
Figure 5G:
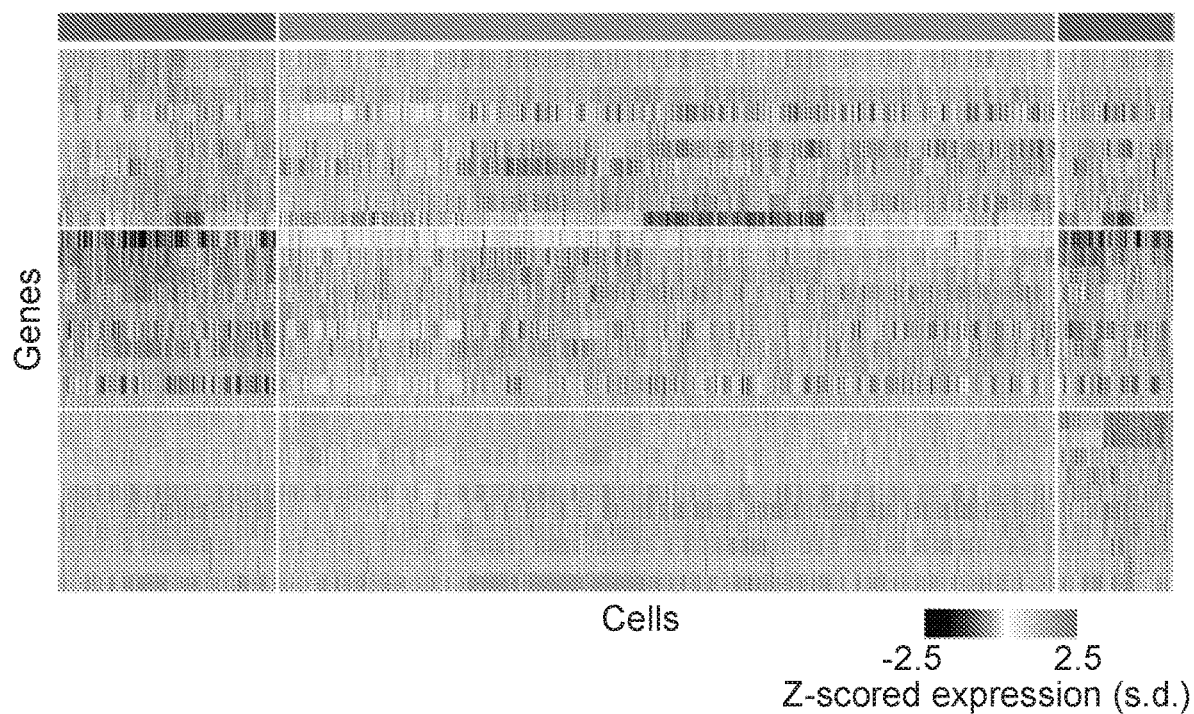
Figure 5H:
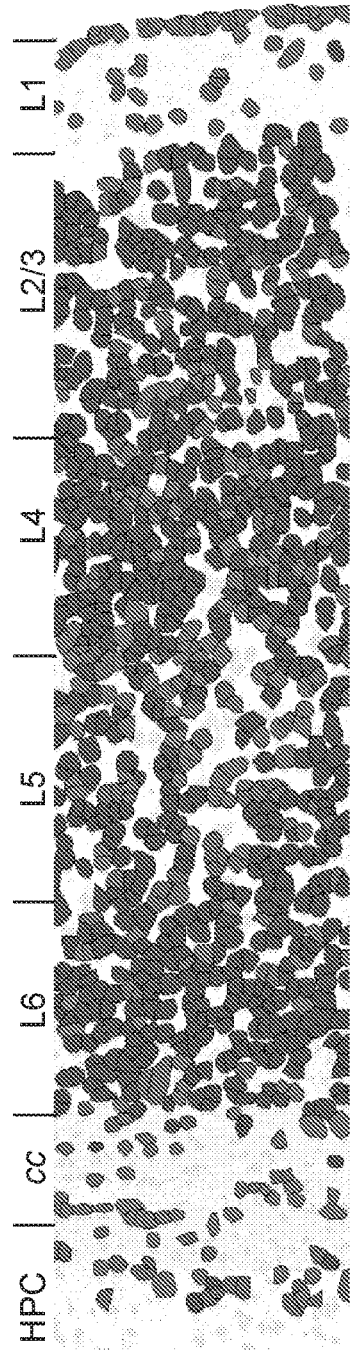
Figure 5J:
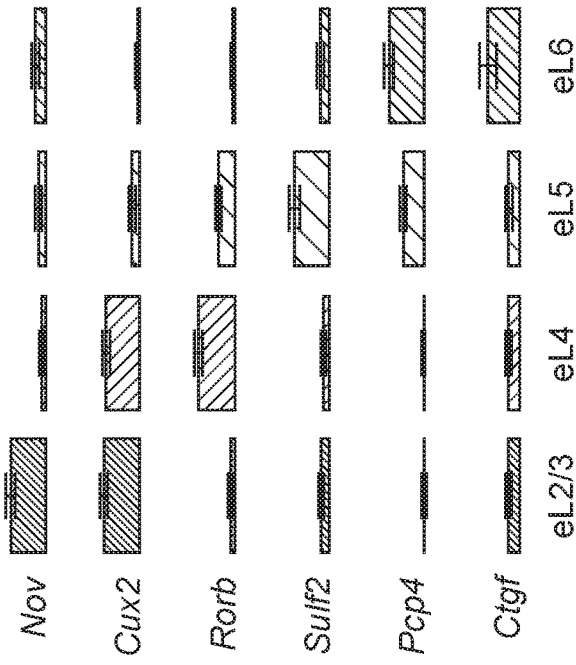
Figure 5I:
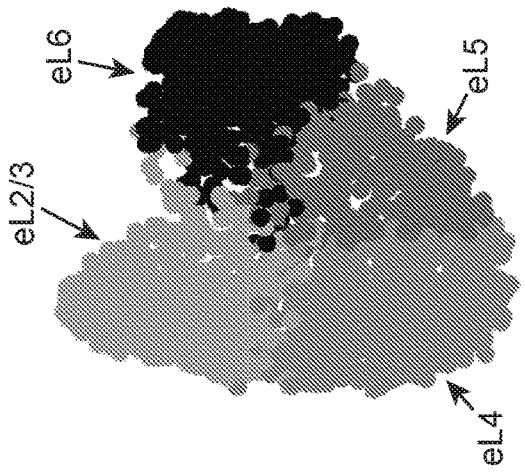
Figure 5K:
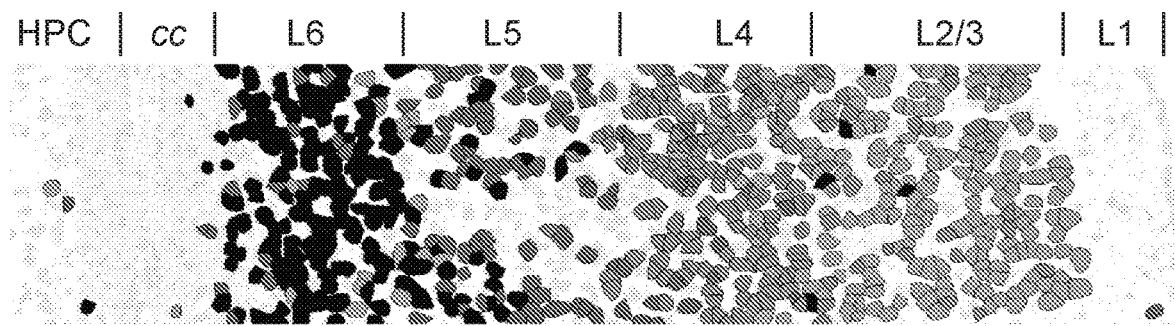
Figure 5L:
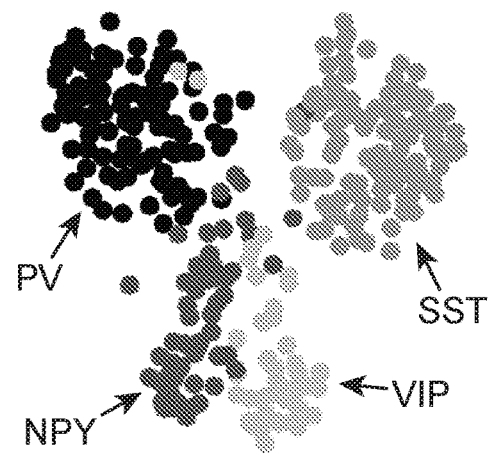
Figure 5M:
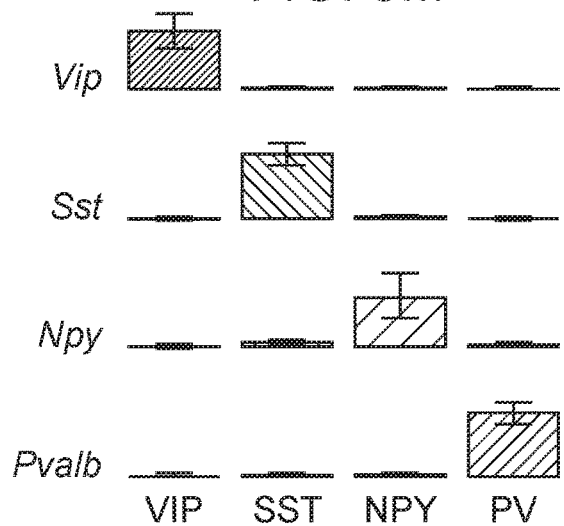
Figure 5N:
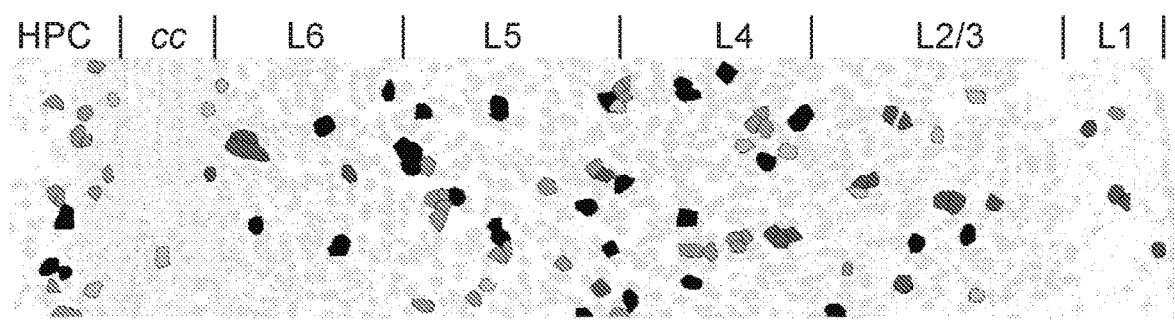

Cell classification was performed using expression data of the 112 cell-type markers. First, over 3,000 cells pooled from four biological replicates were clustered into three major cell types (excitatory neurons, inhibitory neurons and non-neuronal cells) using graph-based clustering following principal-component decomposition, and then further sub-clustered under each category (FIGS. 5F-5H and FIG. 6C). A Uniform Manifold Approximation (UMAP) plot, a non-linear dimensionality reduction technique used to visualize the similarity of cell transcriptomes in two dimensions, showed consistent clustering of major cell types across 3,142 cells pooled from four biological replicates: 2,199 excitatory neurons, 324 inhibitory neurons and 619 non-neuronal cells (FIG. 5F). A gene expression heatmap for 112 cell-type markers shown in FIG. 5G aligned with each cell cluster, showing clustering by inhibitory, excitatory, or non-neuronal cell types. Expression for each gene was z-scored across all genes in each cell. Representative cell-resolved spatial map in neocortex and beyond was shown in FIG. 5H and the cell-types were coded as in FIG. 5F. The clustering of excitatory and inhibitory subtypes (FIG. 5I-5N) depicted UMAP plots (FIGS. 5I and 5L), bar plots of representative genes (FIGS. 5J and 5M) (mean±S.E.M. expression across all cells in that cluster, with each bar scaled to the maximum mean expression across all clusters), and in situ spatial distribution (FIGS. 5K and 5N) of excitatory (FIGS. 5I-5K) and inhibitory (FIGS. 5L-5N) neurons. The number of cells in each cluster was as follows: L2/3: 589; L4: 649; L5: 393; L6: 368; Pv neurons: 111; Vip neurons: 46; Sst neurons: 46; Npy neurons: 56. Inclusion of cells in clusters was guided entirely by amplicon representation in each cell without using spatial information; excitatory cell clusters were then named according to the spatial layering observed for that cluster, while inhibitory cell clusters were named according to the dominant cell-type amplicon based on the strong segregation of amplicon markers.

Figure 6C:
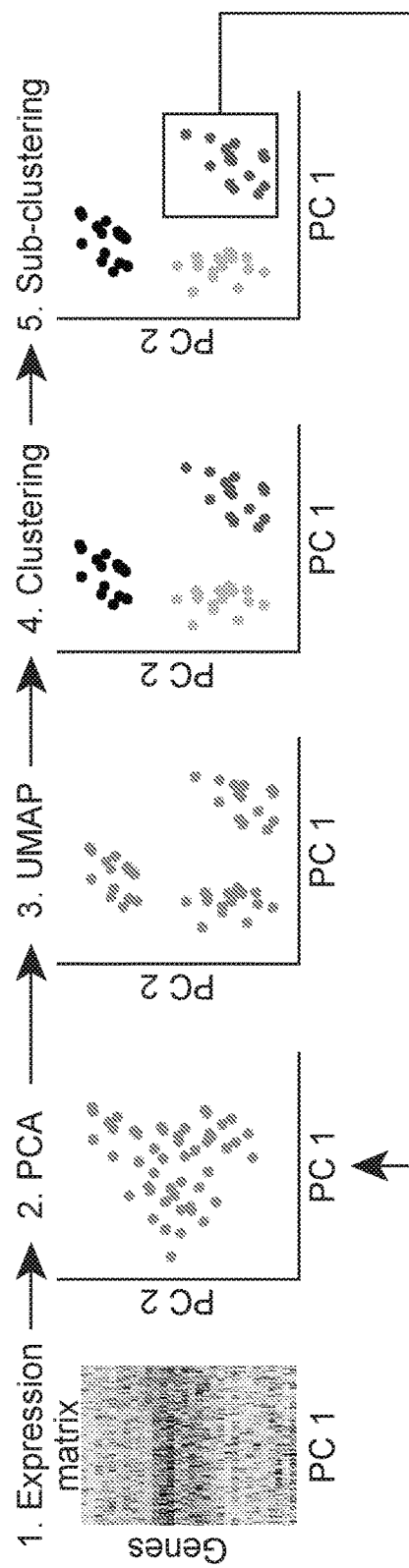

FIG. 6C depicted a method for clustering and subclustering per-cell expression data: (1) data were represented in a matrix of cells-by-genes, as z-scored log-transformed counts; (2) principal components analysis (PCA) was applied to the matrix to reduce to a cells-by-factors matrix; (3) the location of cells was plotted using uniform manifold approximation for visualization (UMAP) (a nonlinear dimensionality reduction technique for the 2D visualization of high-dimensional data); (4) cells were clustered by PCA values using shared-nearest-neighbor-based graph clustering; and (5) the expression values of cells corresponding to individual clusters are then taken and used again for sub-clustering.

Figure 7C:
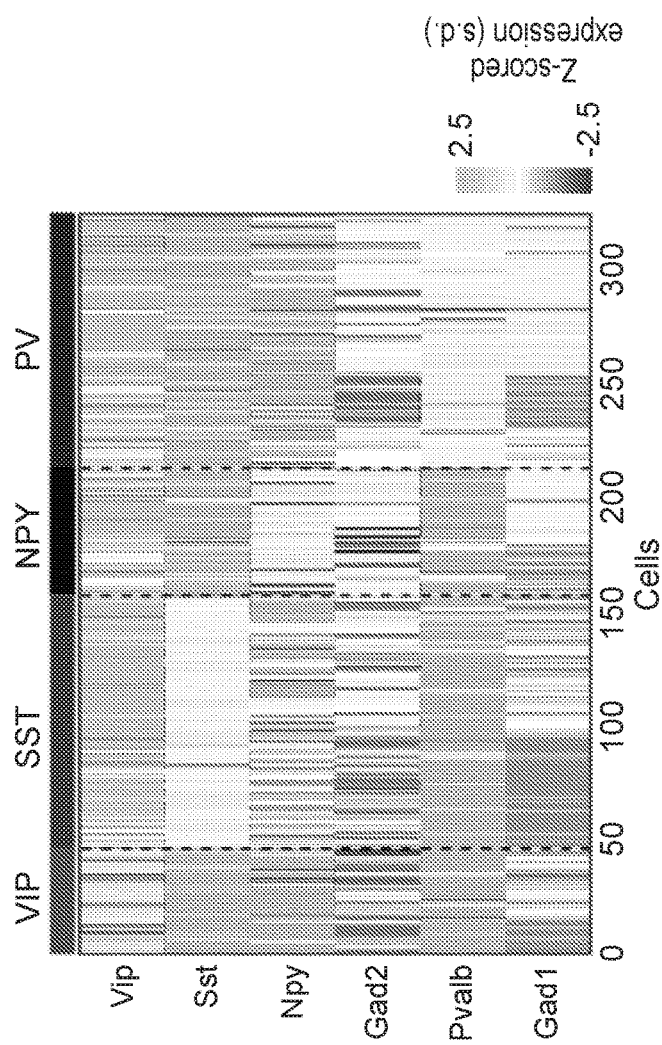
Figure 7D:
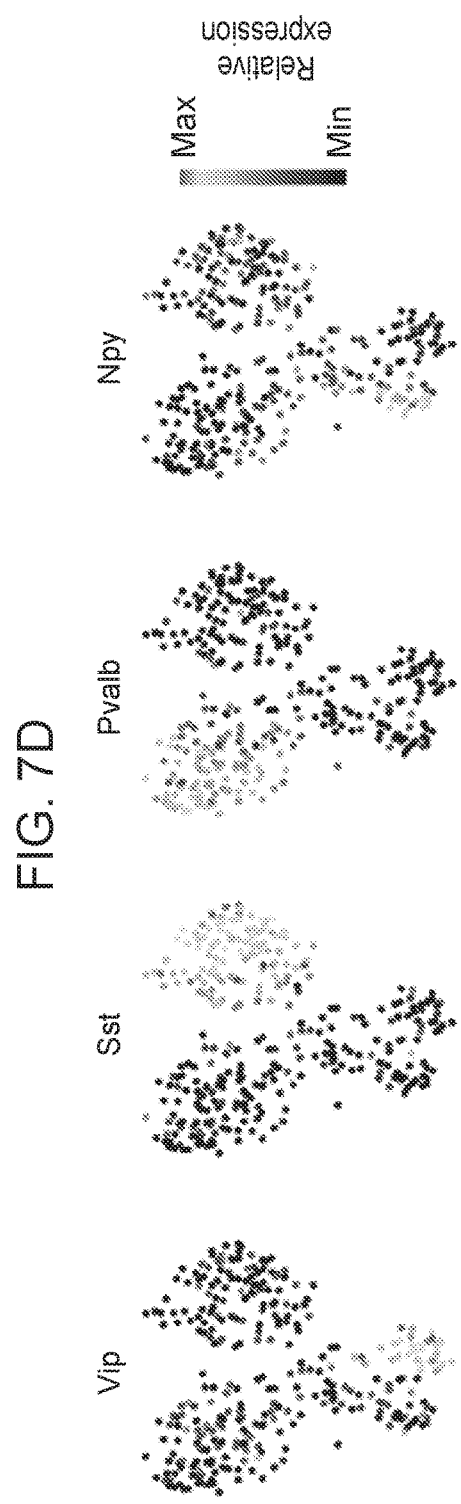

The richly-defined excitatory neurons segregated into four major types, denoted (eL2/3, eL4, eL5 and eL6; FIGS. 5I-5K and FIGS. 7A-7B) by spatial correspondence with anatomic cortical layers and expression profiles of known layer-specific gene markers. A Z-scored expression matrix of excitatory cell types in FIG. 7A showed clustering of multiple differentially-expressed genes per cell type. Genes shown were selected based on a false discovery rate (FDR)-adjusted P value threshold of $10^{-10}$ and a minimum log 10 fold change of 0.1, using a likelihood-ratio test, for genes that were expressed in cells within each cluster versus cells in any other cluster. FIG. 7B depicted UMAP visualization of relative expression (normalized to min and max across all excitatory cells) of multiple known layer-specific genes enriched in each cluster across cells, showing that most are enriched in a specific excitatory subtype. FIG. 7C depicted expression matrix of inhibitory cell types, selected as in FIG. 7A. FIG. 7D depicted UMAP visualization showing relative expression of known interneuron marker genes, showing each is enriched specifically in an inhibitory neuronal subtype.

Although spatial organization of the four excitatory types exhibited a layered pattern, there was extensive intermixing among different cell types within each layer. Inhibitory neurons were also clustered into four major types, denoted by the dominant interneuron marker of each subtype (Vip, Sst, Npy and Pvalb, FIGS. 5L-5N and FIGS. 7C-7D); the Vip and Npy type were observed to distribute more to the upper layers (L1-3) while Sst and Pvalb types were found more commonly in the lower layers (L4-6).

Figure 8B:
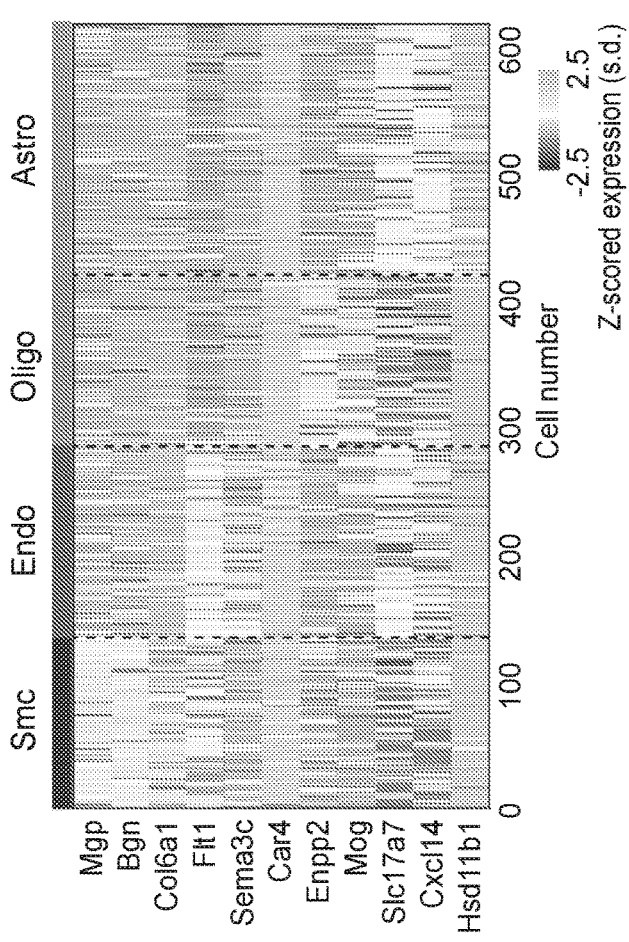
FIG. 8A-8C depict the subclustering of non-neuronal cell types.
Figure 8A:
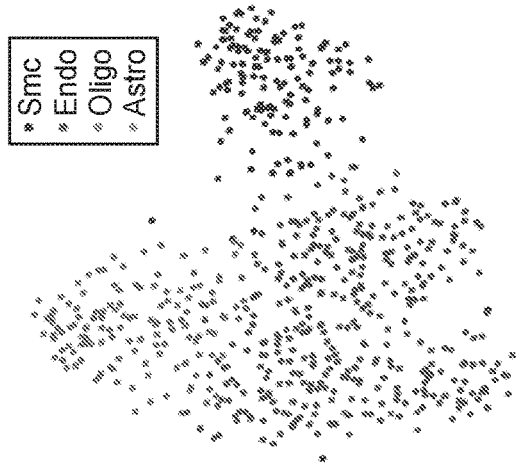
Figure 8C:
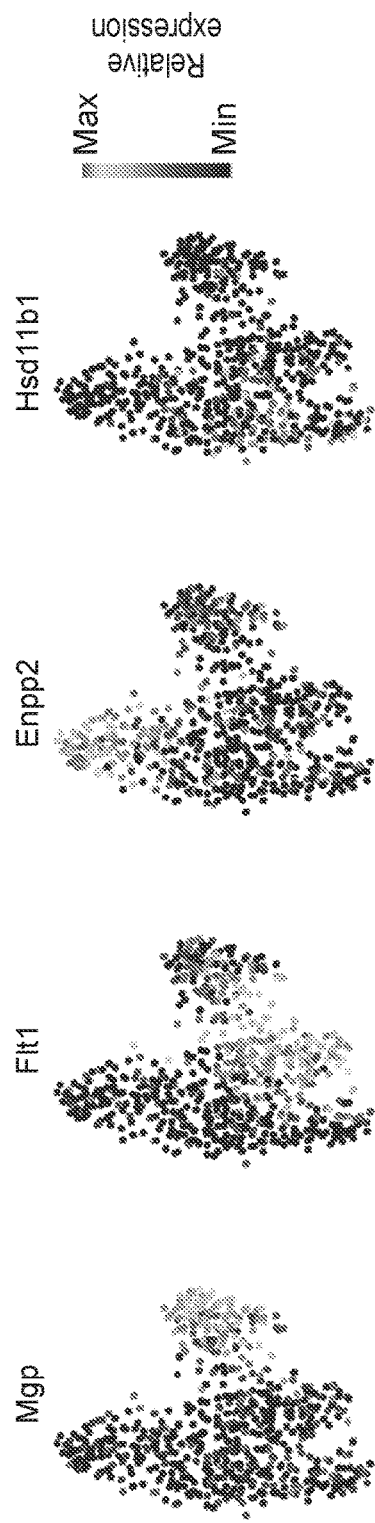

Non-neuronal cell types, including astrocytes, oligodendrocytes, endothelial cells, and smooth muscle cells were also detected (FIGS. 8A-8C). The number of major cell-types illustrated here (12 in total) can be further broken down (single-cell RNA sequencing can lead to subtyping into 40 or more, consistent with the readily-apparent heterogeneity of gene expression within each type; FIGS. 7A-7D; FIGS. 8A-8C). UMAP visualization of 4 non-neuronal cell types was depicted in FIG. 8A. A Z-scored expression matrix of non-neuronal cell types was depicted in FIG. 8B. Genes shown were selected based on a false discovery rate (FDR)-adjusted P value threshold of $10^{-10}$ and a minimum log 10 fold change of 0.1, using a likelihood-ratio test, for genes that are expressed in cells within each cluster versus cells in any other cluster. FIG. 8C depicted UMAP visualization of per-cell expression of marker genes (top differentially expressed genes per cluster) for non-neuronal cell types, showing specificity for that cluster. Color indicated relative expression (normalized to min and max) of each gene across all non-neuronal cells.

Figure 9A:
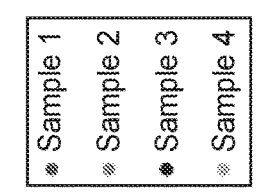
Figure 9A:
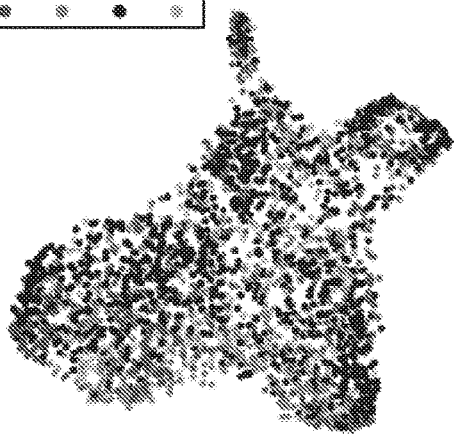
Figure 9C:
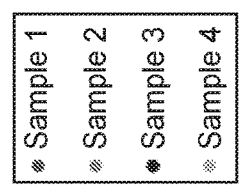
Figure 9C:
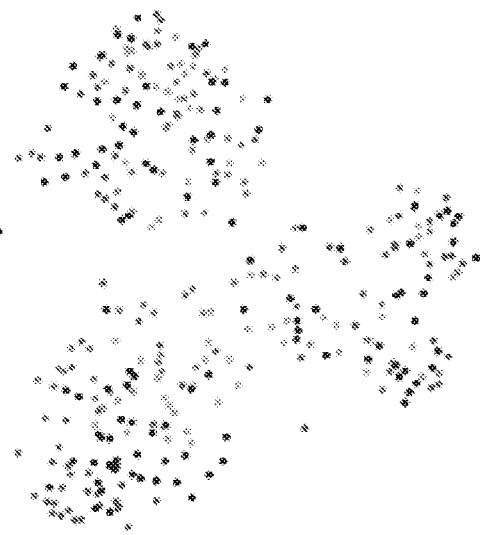
Figure 9B:
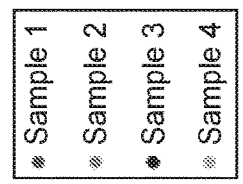
Figure 9B:
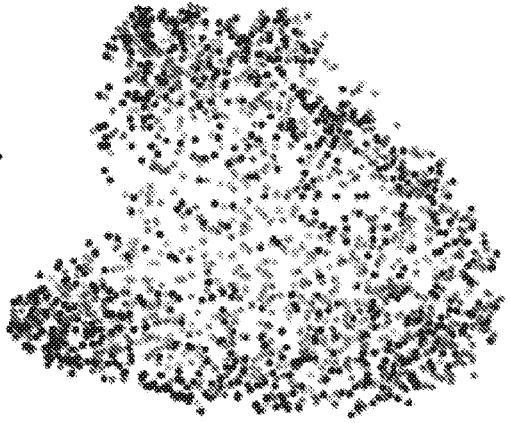
Figure 9F:
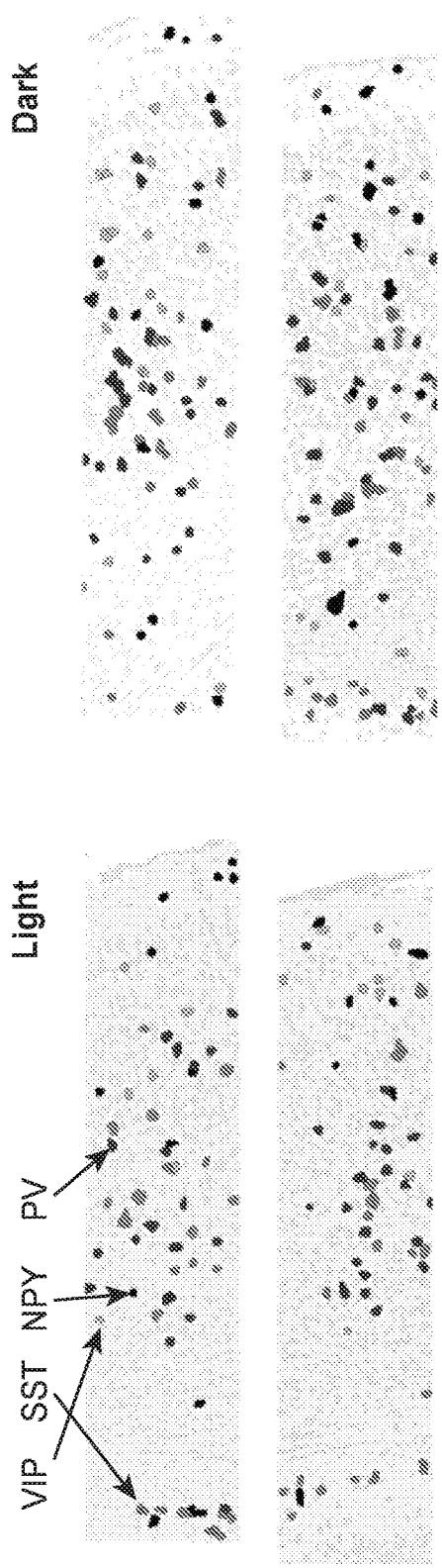
Figure 9G:
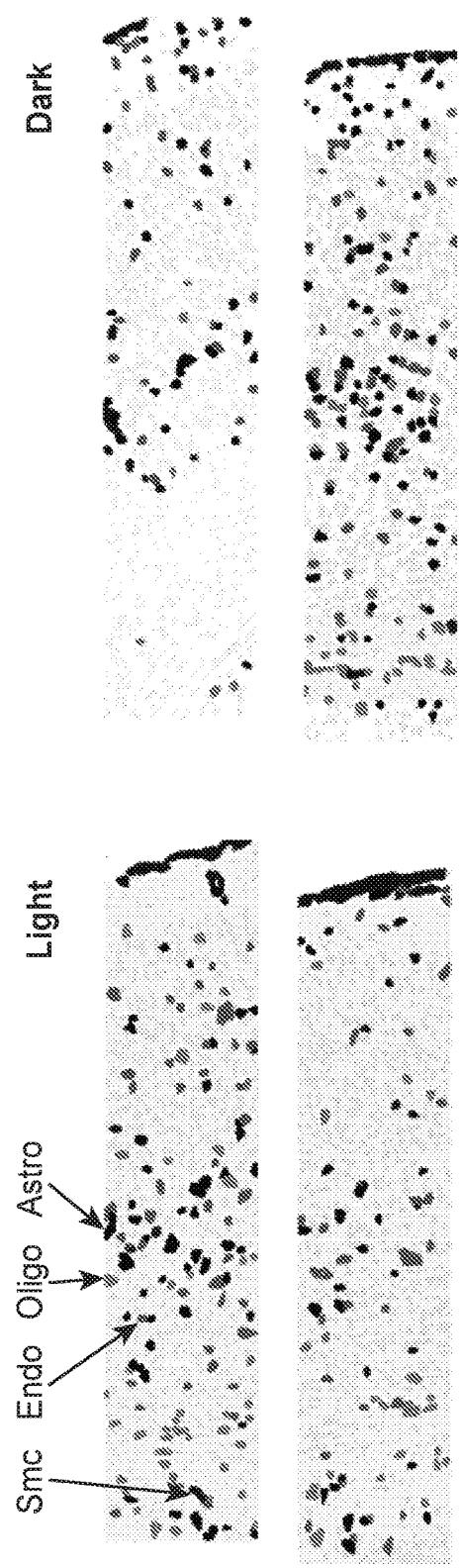

With the targeted 112-gene set and at the size of 600-800 cells per sample, all 12 major cell types were reliably detected without batch effects and with highly similar spatial patterning among four biological replicates (FIGS. 9A-9G). FIGS. 9A-9C depicted UMAP visualization of cells coded by sample replicates, and then grouped by major clusters (FIG. 9A), excitatory subclusters (FIG. 9B), and inhibitory subclusters (FIG. 9C). Spatial maps of light and dark replicate pairs (FIGS. 9D-9G, top and bottom) of all cell types (FIG. 9D), excitatory cell types (FIG. 9E), inhibitory cell types (FIG. 9F), and non-neuronal cell types (FIG. 9G).

Example 6

Single-Cell RNA Sequencing

Figure 10A:
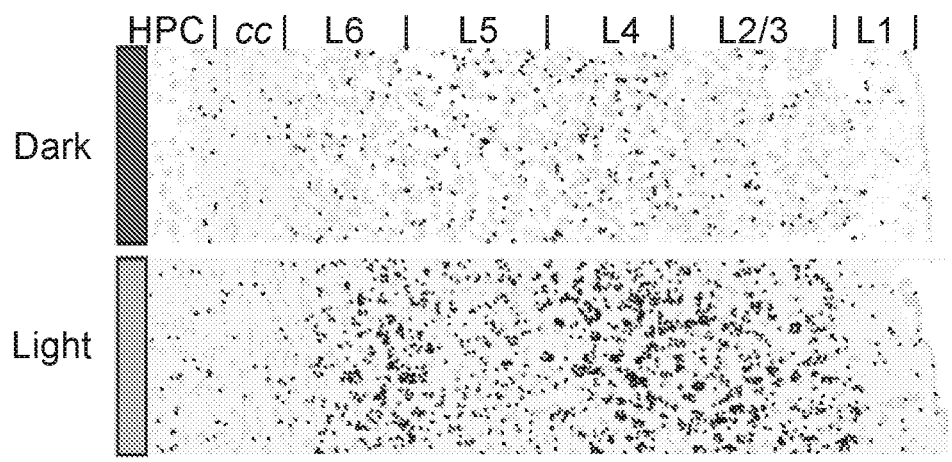
FIG. 10A-10D depict the behavioral experience of detecting and quantifying cell type-specific-regulation of activity-regulated genes (ARGs) using the methods described herein.
Figure 10A:
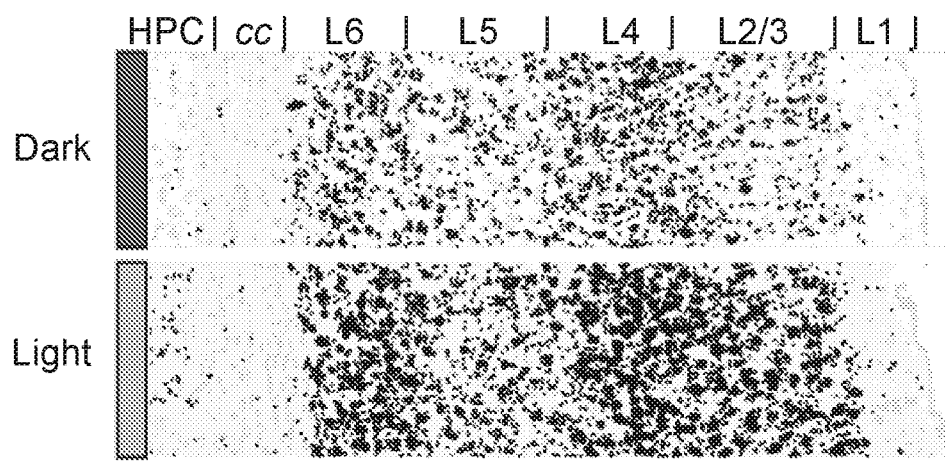
Figure 10A:
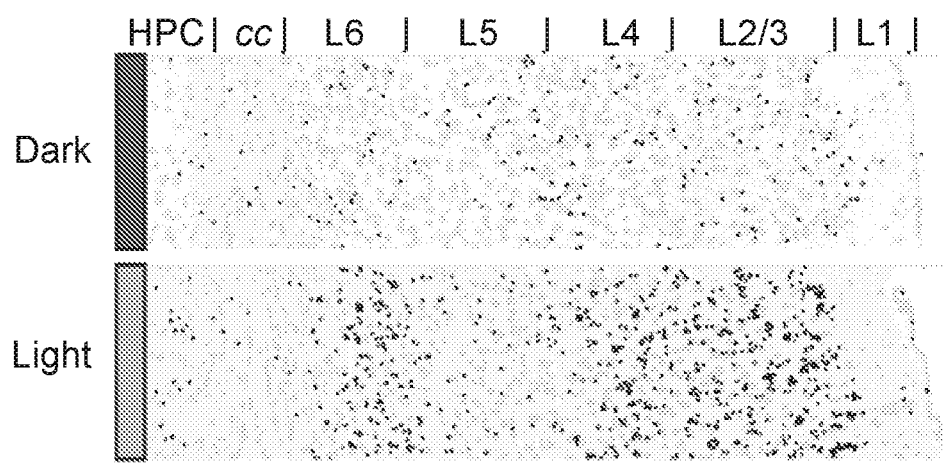
Figure 10B:
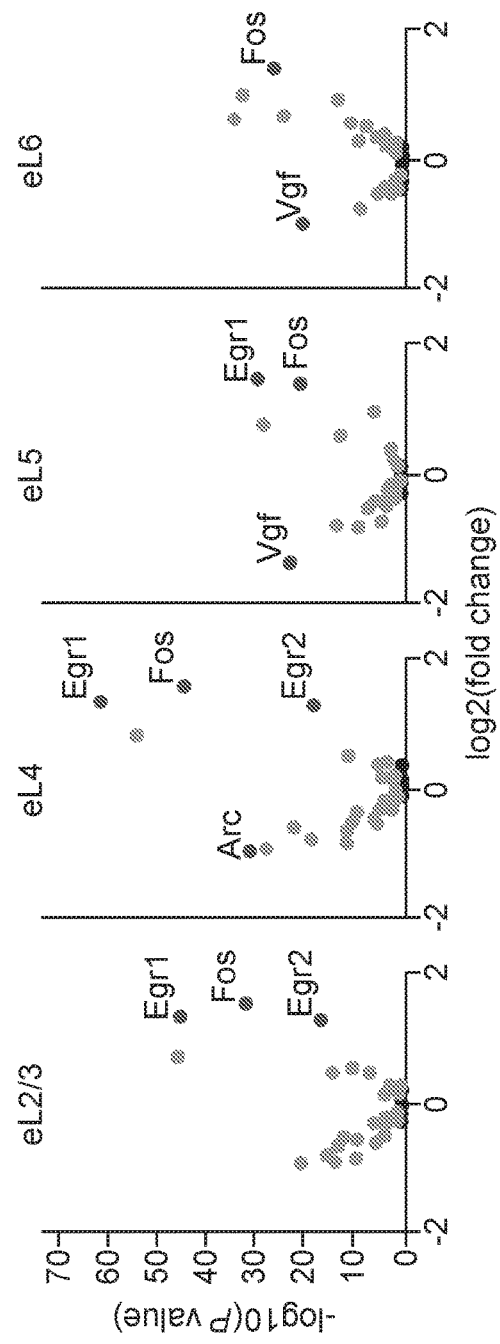
Figure 10C:
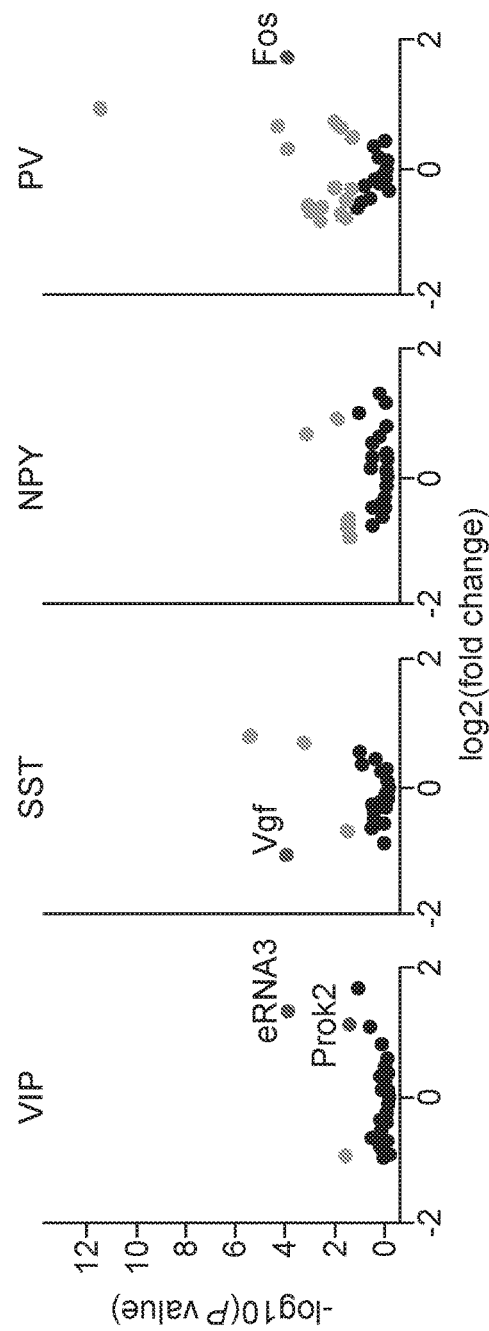
Figure 10D:
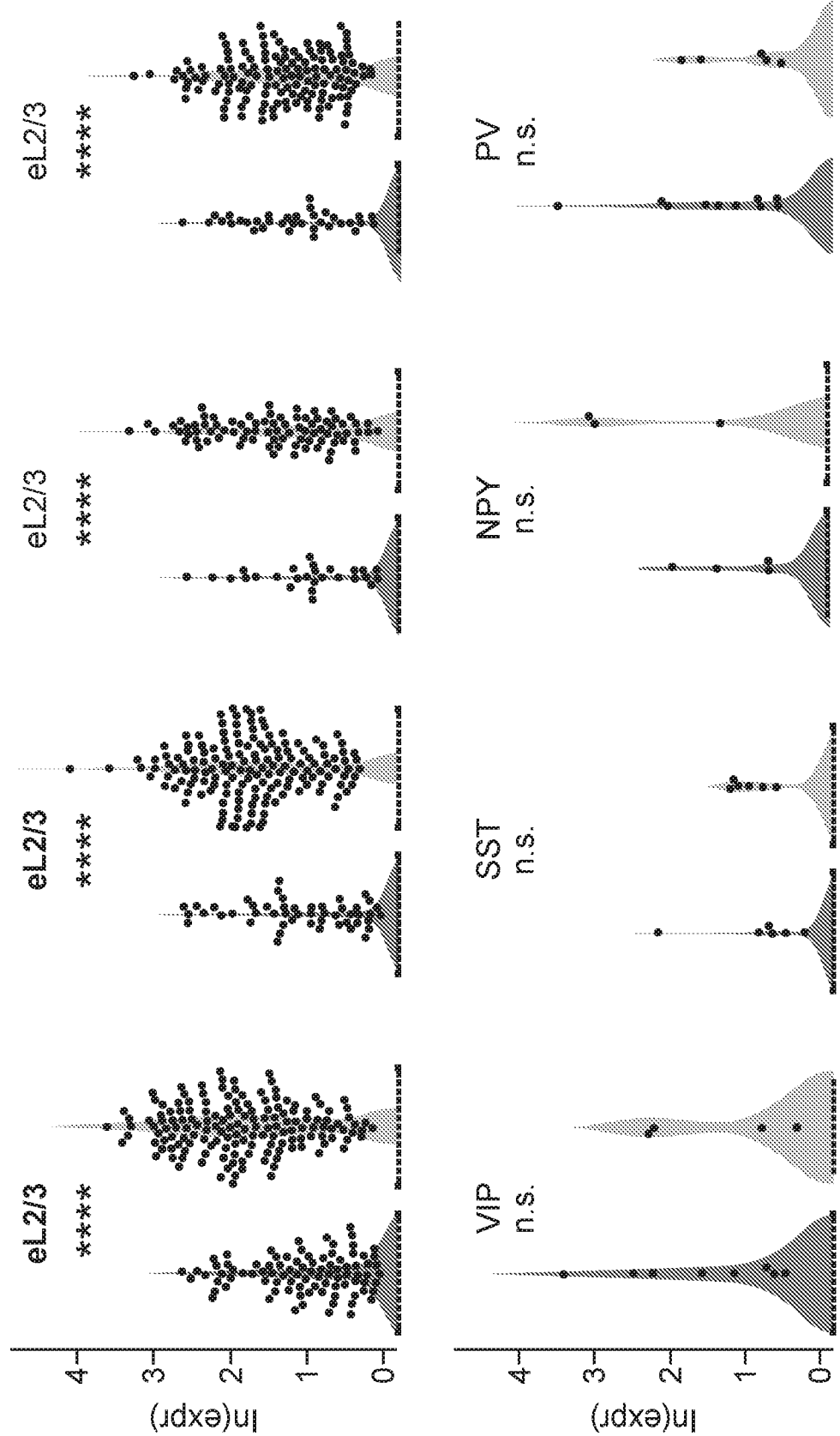

STARmap's quantitative capabilities at the single-cell level were evaluated to test differential gene expression analyses across experimental conditions, in molecularly-defined cell types. Visual-stimulus-dependent gene expression patterns (via 48 defined ARGs with single-cell resolution in situ) were assessed. Further developing the single-cell RNA sequencing procedure, mouse brains were flash-frozen with minimal handling time after sacrifice (less than 5 min) and without drug treatment, for maximal preservation of native transcriptional signatures. Global induction of known immediate-early genes (Fos, Egr1 and Egr2, FIGS. 10A-10D) was observed in primary visual cortex upon 1-hour of light exposure. At single-cell resolution, the quantitative extent (fold change in expression) of ARG changes exhibited striking diversity across neuronal cell types (FIGS. 10B-10C and FIGS. 11A-11C). FIG. 10A validated spatial expression pattern in visual cortex of prototypical ARGs known as immediate early genes (IEGs). Sacrifice was in darkness or after 1 hr light exposure. FIGS. 10B and 10C depicted volcano plots of log fold-change in gene expression between light and dark conditions in inhibitory and excitatory cell types. Genes with significantly increased or decreased expression (false discovery rate adjusted P value <0.05, Wilcoxon rank-sum test) were labeled. Many ARGs showed cell-type specificity pointing to discovery of unanticipated cell type-specific logic of excitation-transcription coupling. FIG. 10D depicted a violin plot of Egr2 expression by cell type. **** $P<0.0001$, n.s. indicated not significant, Wilcoxon rank-sum test; cell types, fold change indicated more than 2. In general, ARG expression programs in excitatory neurons across different layers were highly similar, whereas ARG expression programs in inhibitory cells exhibited much more distinct cell-type specific characteristics (FIG. 11B); for example, Egr2 exhibited light-induction across excitatory neurons (FIG. 10D) but not in inhibitory neurons, while in contrast, Prok2 was upregulated in Vip inhibitory neurons (FIG. 10C).

Figure 11A:
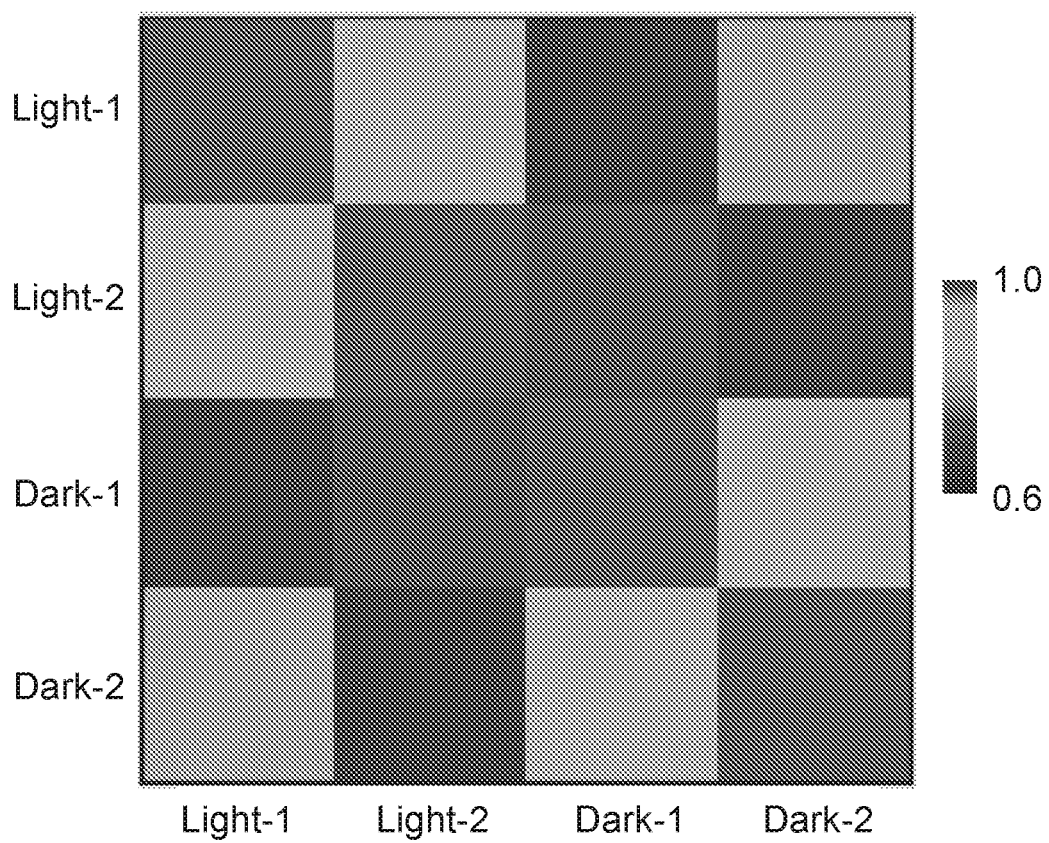
FIG. 11A-11C depict the expression information of dark and light samples and ARGs using the methods described herein.
Figure 11B:
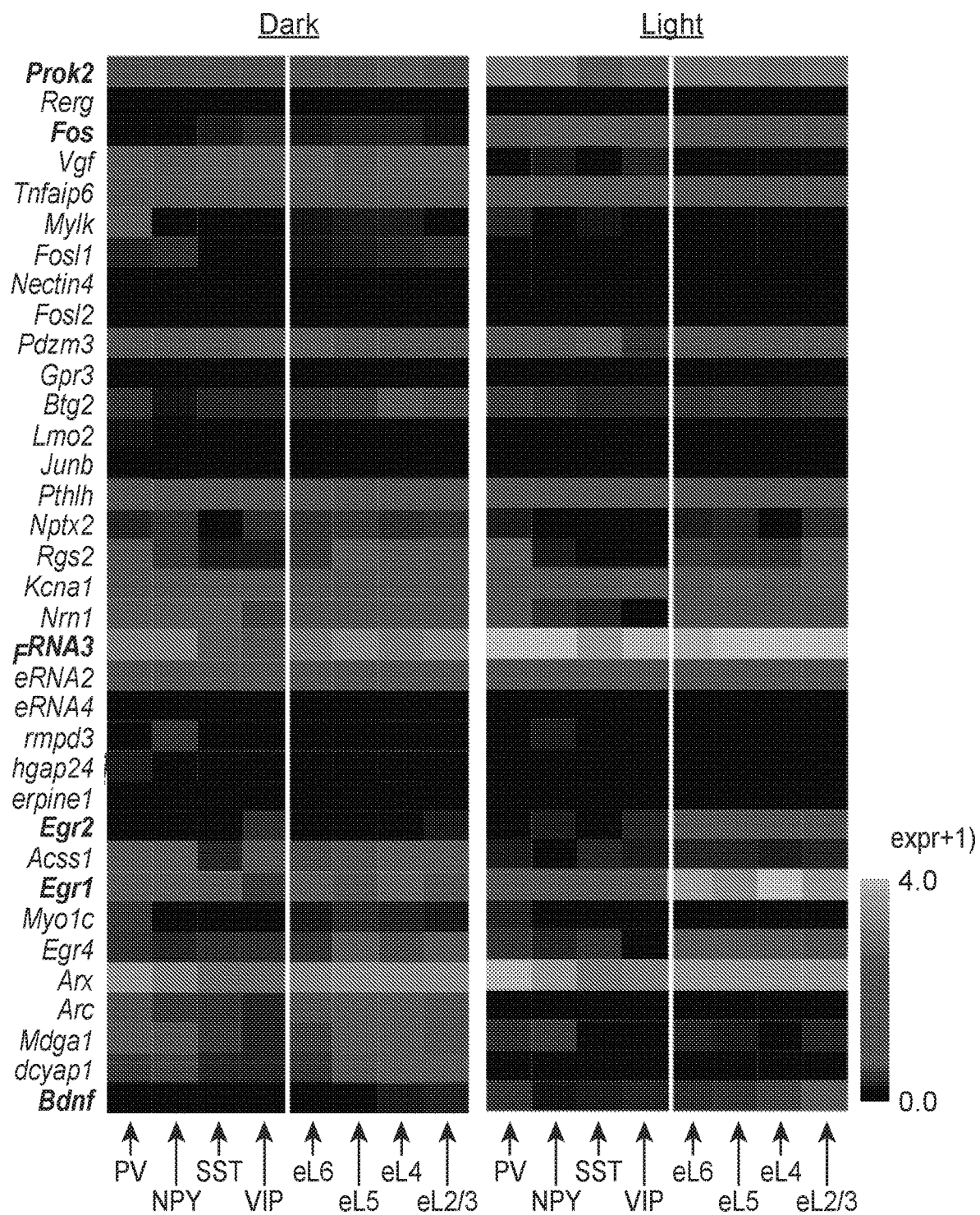
Figure 11C:
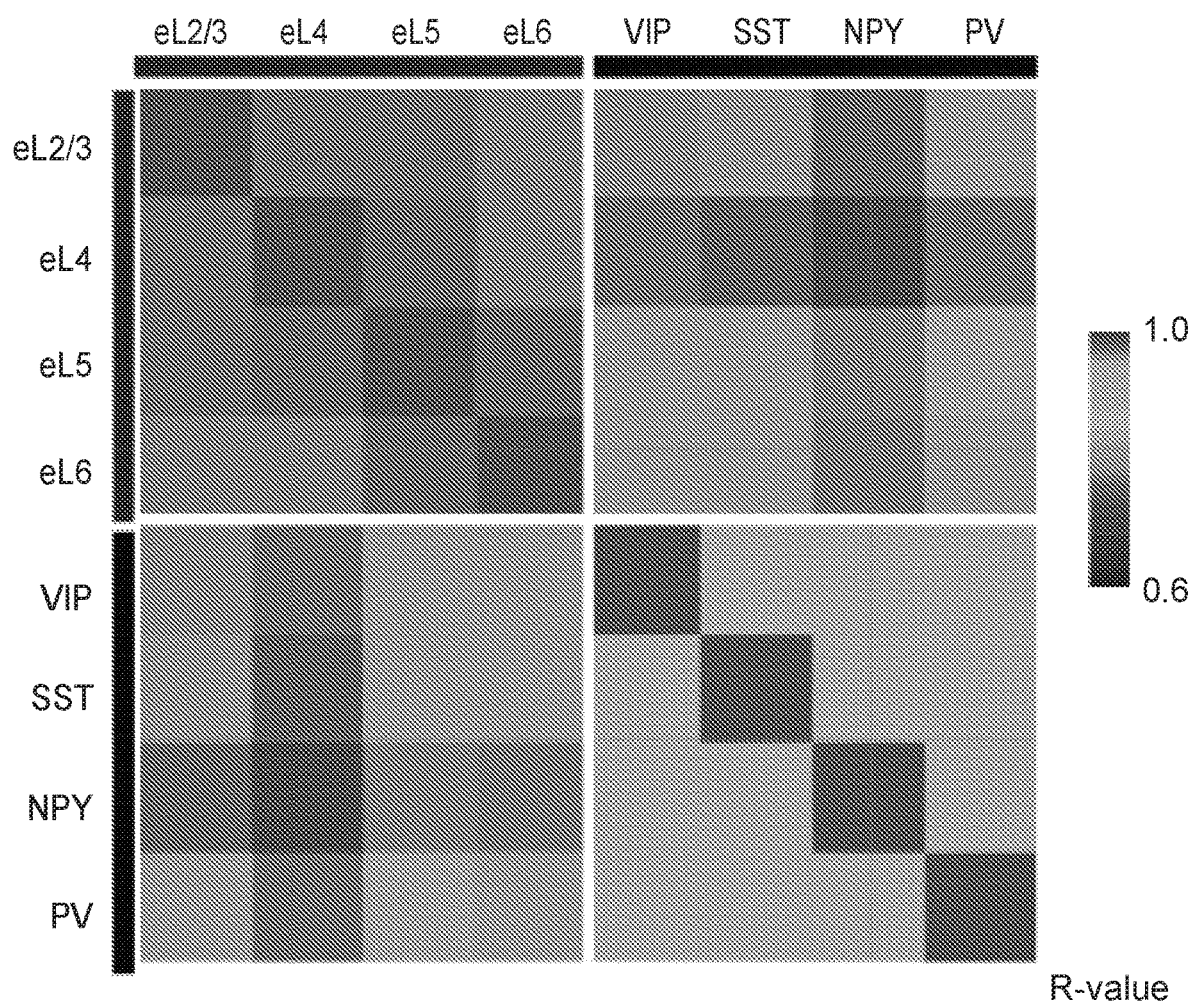

Finally, since neural activity can trigger co-transcription of noncoding RNAs from within enhancers of ARGs, exemplars of these enhancer RNAs were studied (eRNAs 1-5 of the Fos gene); these transcripts, not polyadenylated, were very difficult to measure with current single-cell RNA sequencing. However, eRNA3 was identified as the most significant and consistent ARG marker (FIG. 11B). FIG. 11A depicted a correlation of 160 genes of dark/light biological replicates showing that samples of the same condition were highly correlated than samples under different conditions; scale, Spearman R-value. FIG. 11B depicted log-scaled expression data (counts per cell) of ARGs in inhibitory and excitatory neuron subtypes. Genes with significantly increased expression in any cell type were highlighted. FIG. 11C depicted a heatmap of the correlation of neuronal subtypes based on the correlation of mean expression of all ARGs in that cluster in response to light, showing that cells from inhibitory cell types were more correlated with other inhibitory cell types than with excitatory cell types, and vice versa. Note that scale ranged from R=0.8 to R=1.

Example 7

STARmap Method Applied to Large Tissue Volumes

Figure 12:
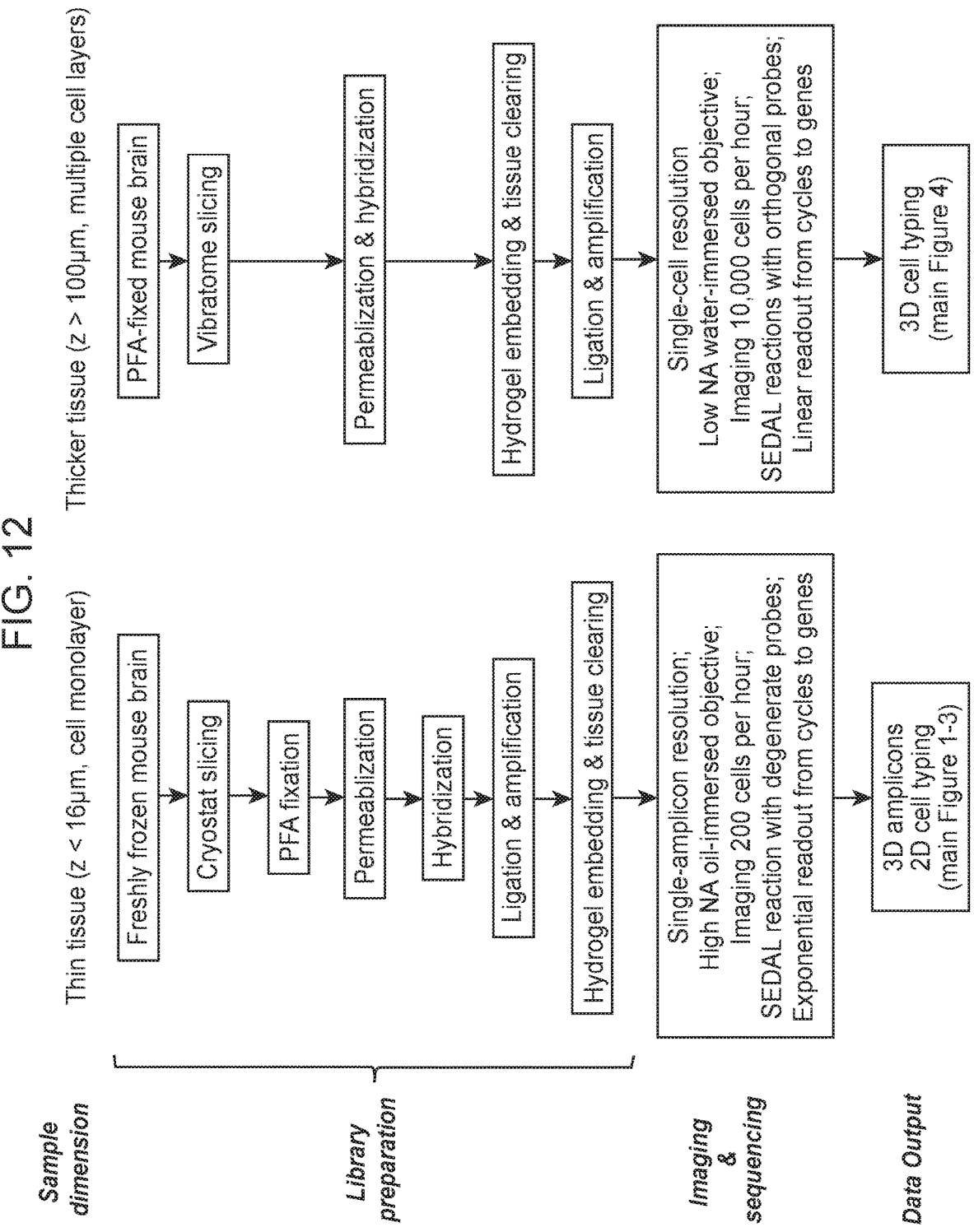
FIG. 12 depicts experimental flowcharts of STARmap for thin and thick tissue sections.

The 160-gene experiments were carried out in brain slices no more than 1 cell body thick, thus capabilities of the STARmap method for capturing 3D organization of cells in tissue volumes were not yet tested. STARmap was further developed to overcome limitations in diffusional access and imaging throughput for intact tissue volumes, with a strategy for linearly reading out gene expression at cellular resolution to enable high-throughput molecular analysis in tissue volumes (FIG. 12 and FIG. 13). FIG. 12 depicted methods disclosed herein including the steps of sample dimension, library preparation, imaging and sequencing, and data output. For thin tissue (z<16 µm, cell monolayer), the library was prepared using freshly frozen mouse brain, followed by cryostat slicing, PFA fixation, permeabilization, hybridization, ligation and amplification, and hydrogel embedding and tissue clearing. Imaging and sequencing included single-amplicon resolution; high NA oil-immersed objective; imaging 200 cells per hour; SEDAL reaction with degenerate probes; and exponential readout from cycles to genes. Data output included 3D amplicons and 2D cell typing (FIG. 1A-1E, FIGS. 5A-5N, and FIGS. 10A-10D). For thicker tissue (z>100 µm, multiple cell layers), the library was prepared using PFA-fixed mouse brain, followed by vibratome slicing, permeabilization and hybridization, hydrogel embedding and tissue clearing, and ligation and amplification. Imaging and sequencing included single-cell resolution; low NA water-immersed objective; imaging 10,000 cells per hour; SEDAL reaction with orthogonal probes; and linear readout from cycles to genes. Data output included 3D cell typing (FIGS. 13A-13I).

Figure 13A:
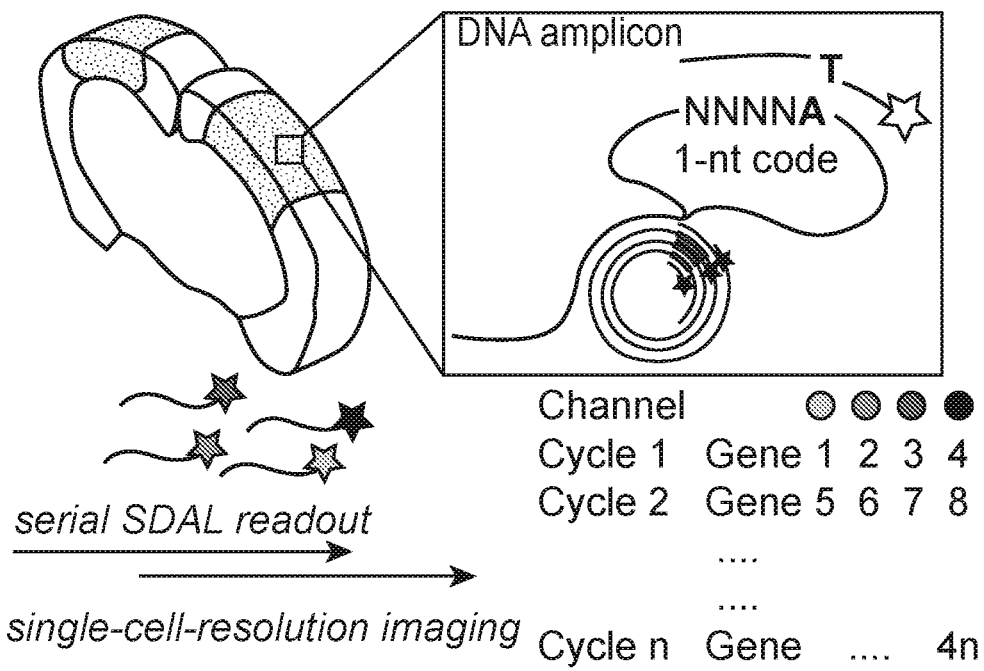
Figure 13B:
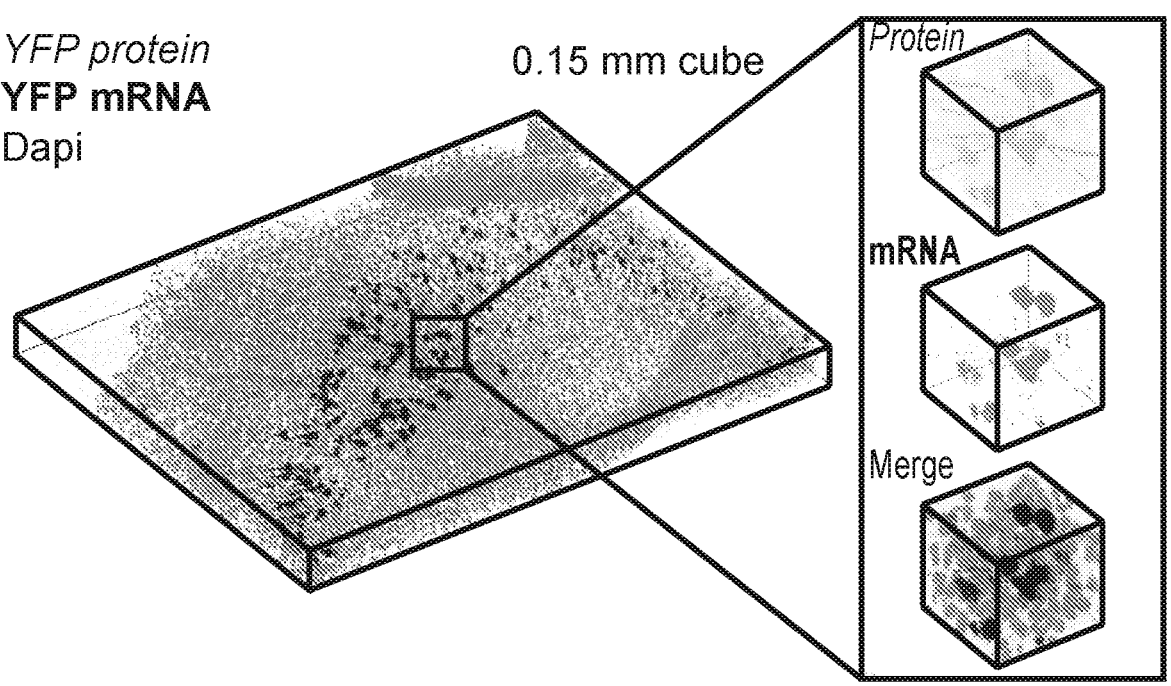

FIG. 13A depicted volumetric STARmapping via sequential SEDAL gene readout. Using a modified STARmap procedure (FIG. 12, right) and cyclic gene readout (4 genes in each cycle), large tissue volumes were rapidly mapped at single-cell resolution without oversampling each amplicon. Specificity and penetration depth of large-volume STARmap were tested initially using Thy1::YFP mouse brains, wherein STARmap successfully detected YFP mRNA across 150 µm of tissue thickness, and specifically co-localized YFP protein and mRNA at single-cell resolution (FIG. 13B) without labeling the tens of thousands of interspersed neighboring cells. Validation showed specific STARMAP labeling of YFP-expressing neurons (from transgenic Thy1::YFP mouse line) in 3D cortical volume. Scale bar indicated 0.5 mm.

Figure 13C:
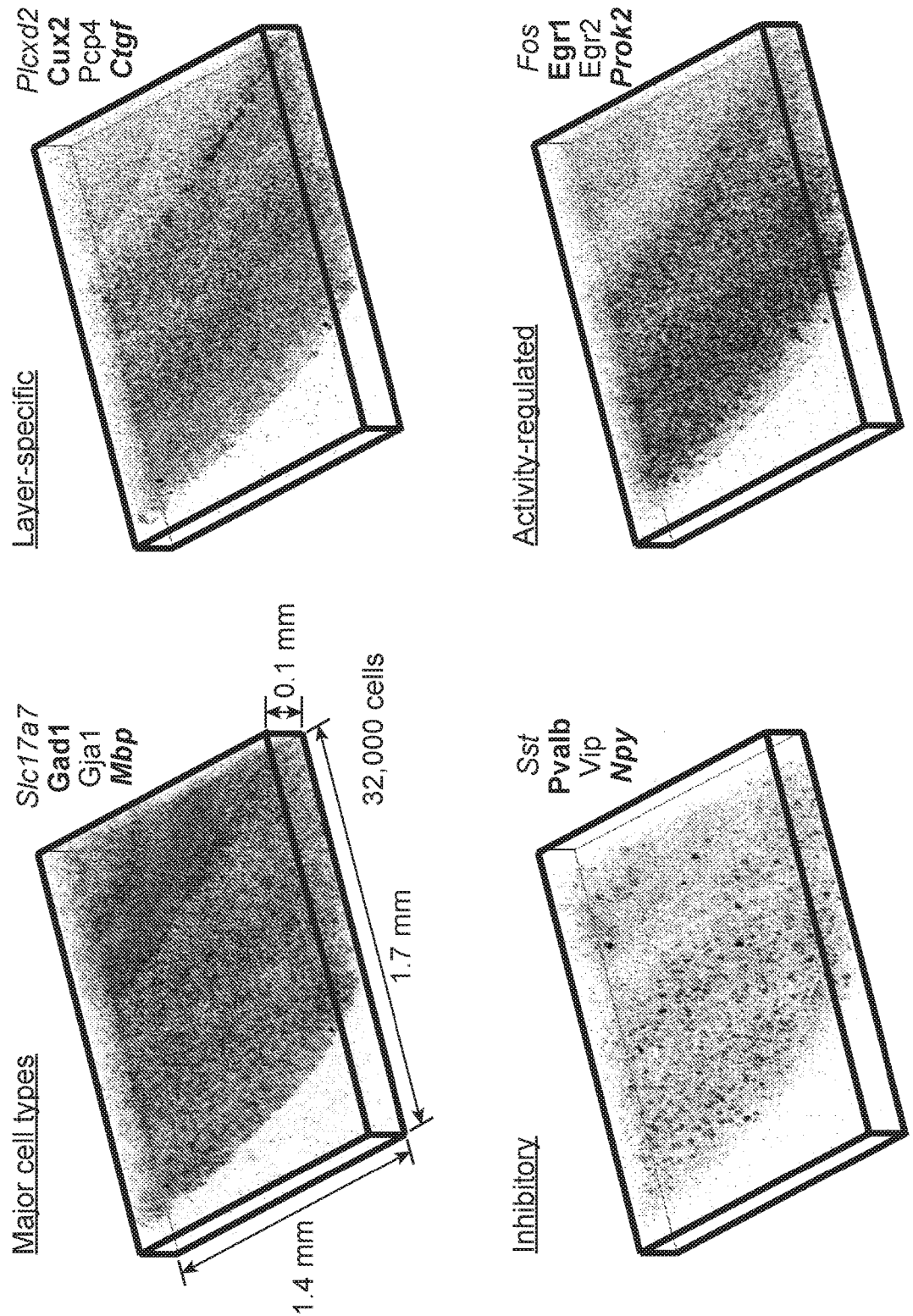

The spatial cell-typing of mouse primary visual cortex was extended to more than 30,000 cells across volumes spanning all six layers and the corpus callosum. Using 28 genes including 23 cell type markers and 5 ARGs read out over 7 cycles of linear SEDAL sequencing (FIGS. 13C-13D and FIGS. 14A-14B), K-means clustering of marker genes (Methods) was applied for each cell-type (recovering 11 cell types corresponding to the majority of those extracted by the 160-gene experiment, but here with only 28 genes). FIG. 13C depicted representative labeling of major cell types (FIG. 13C, left), layer-specific markers (FIG. 13C, left center), inhibitory markers (FIG. 13C, right center), and activity-regulated genes (FIG. 13C, right) acquired over multiple rounds in visual cortex STARmap volumes.

Figure 13D:
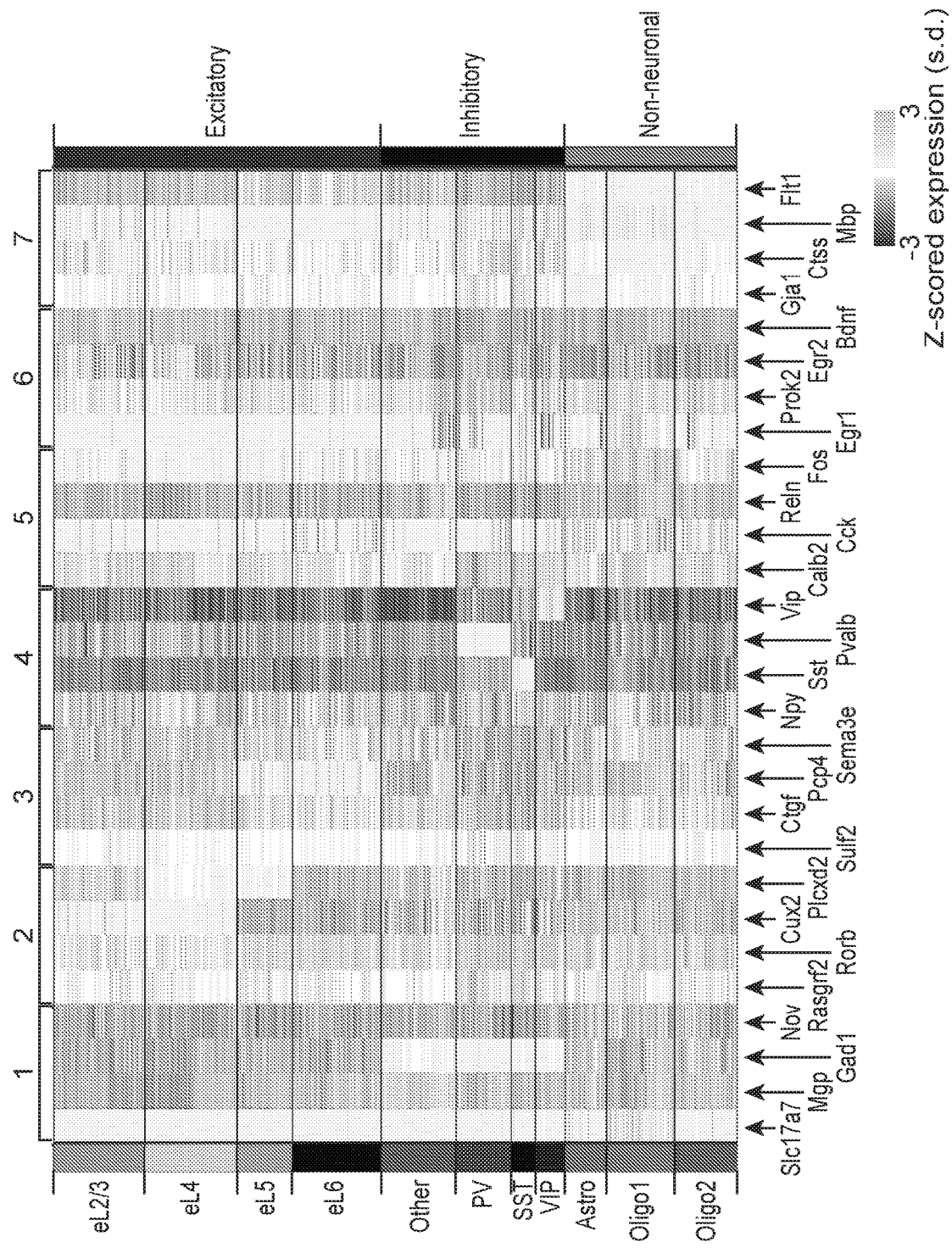
Figure 13E:
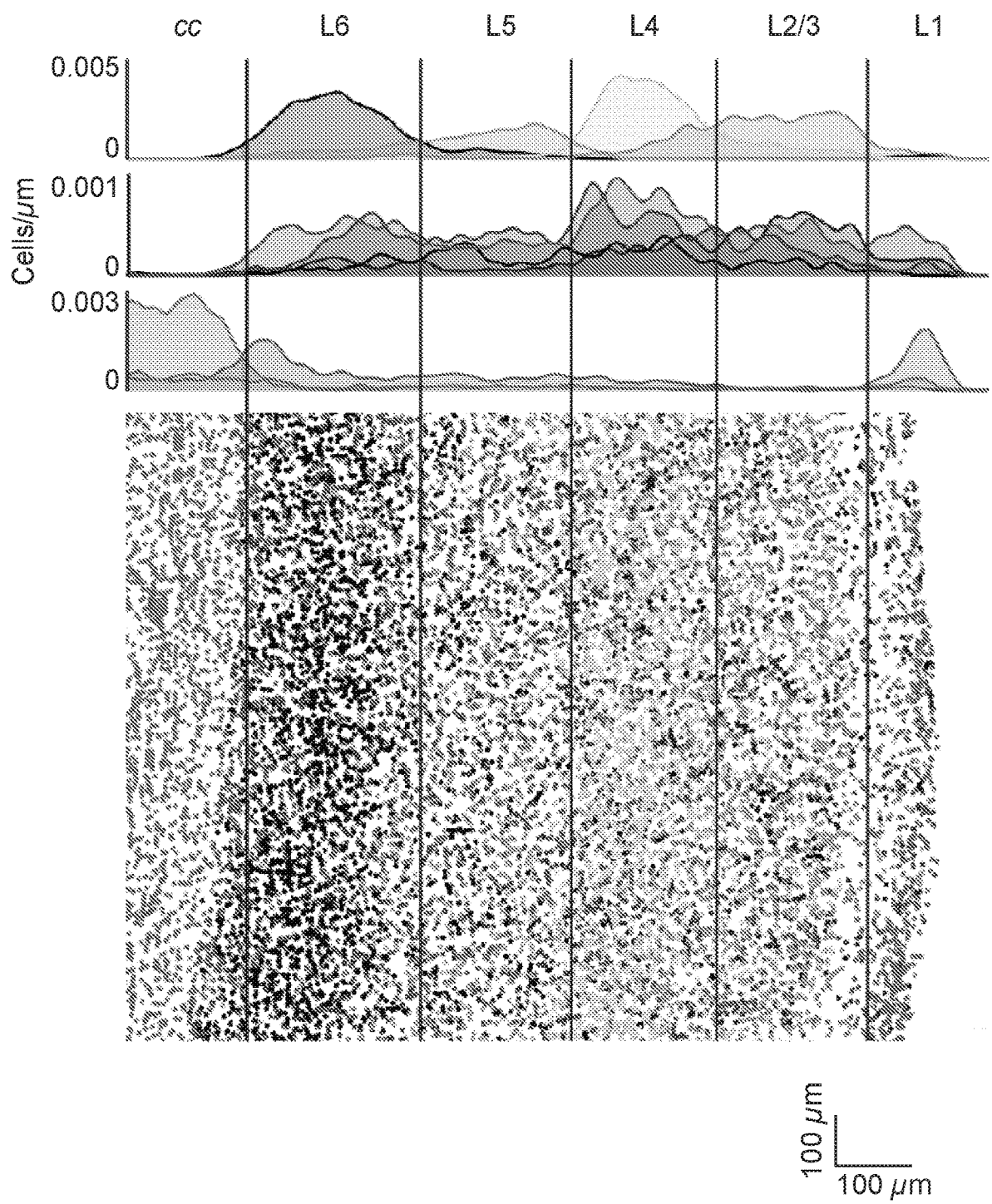
Figure 13F:
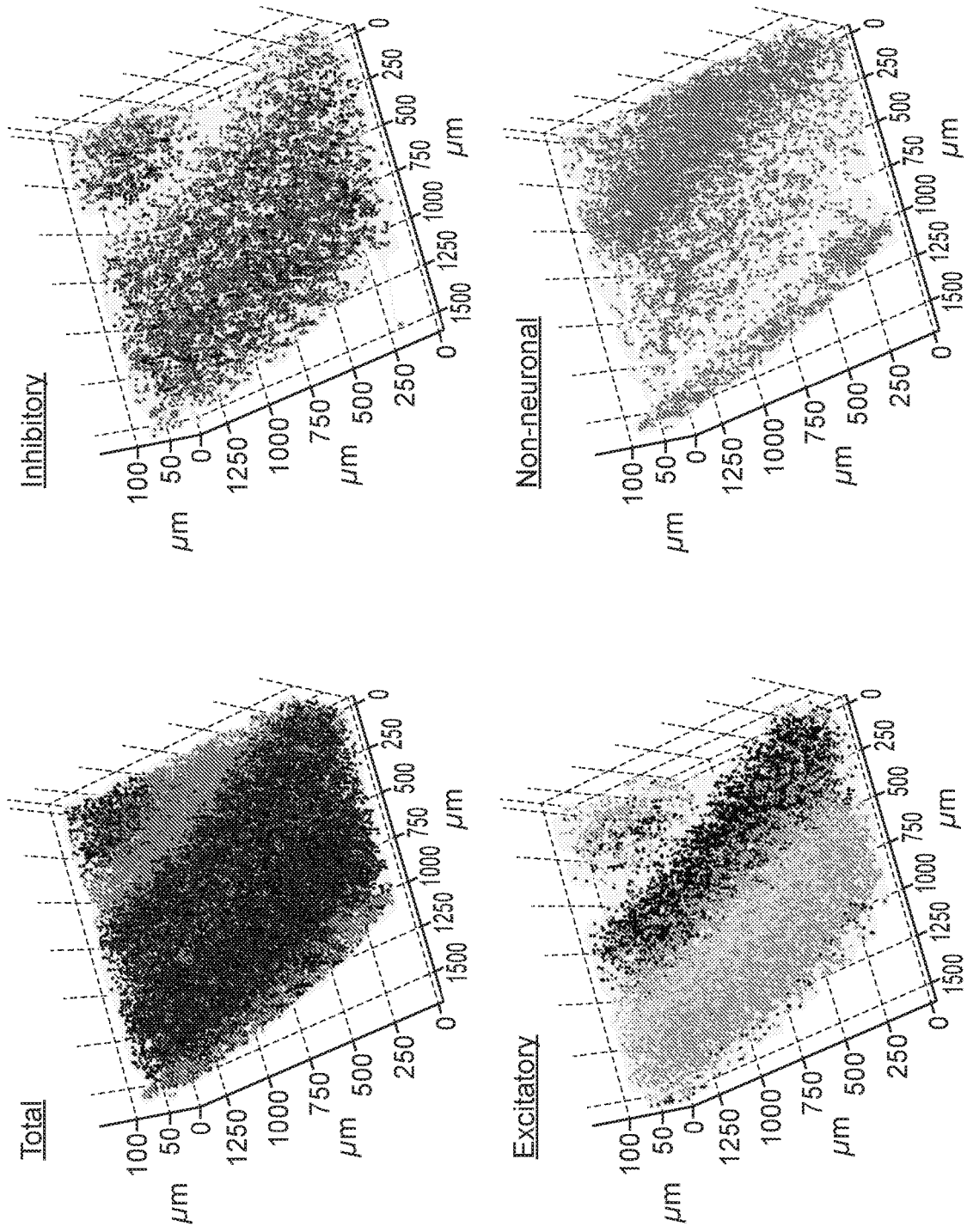
Figure 14A:
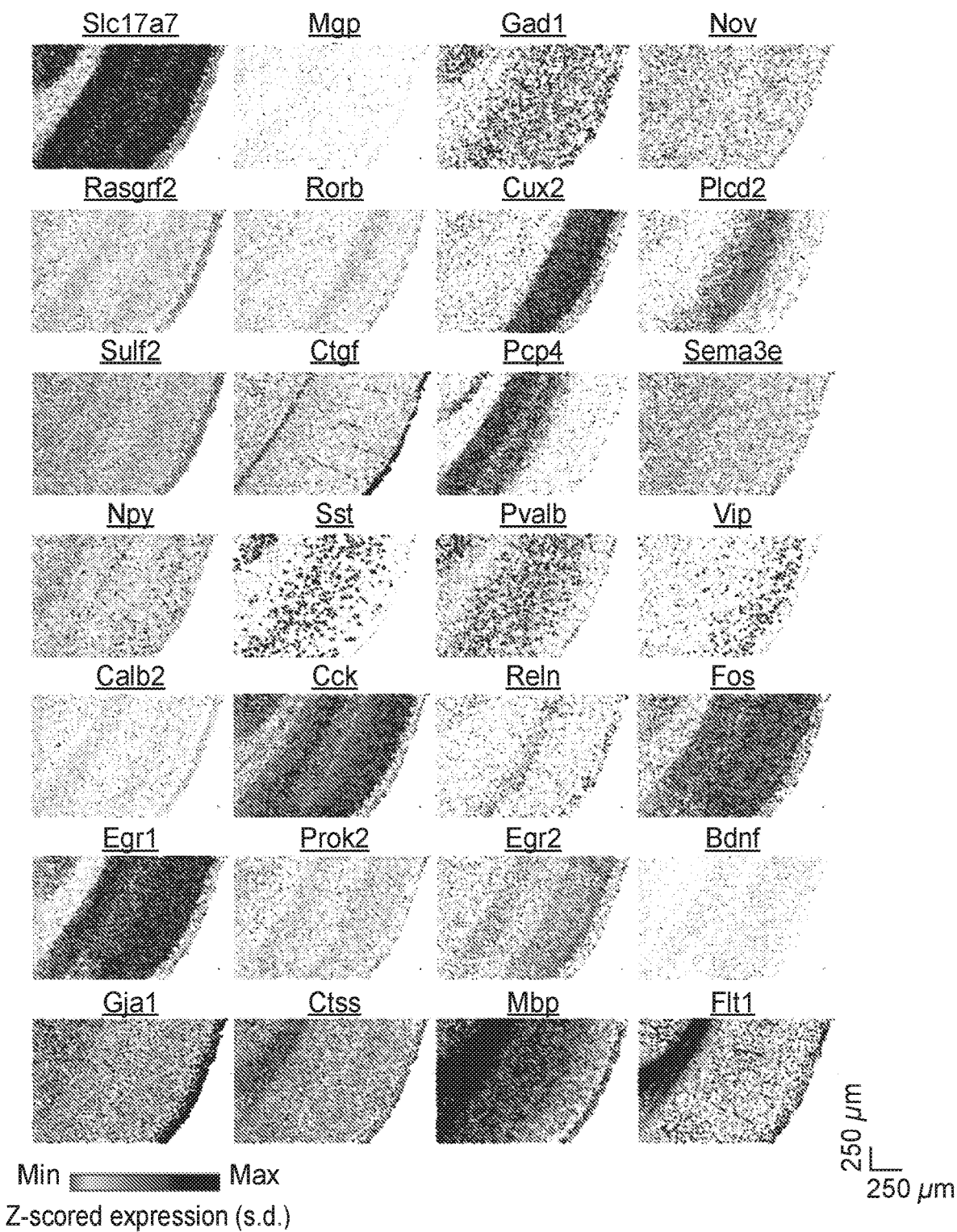
FIG. 14A-14B depict sequential SEDAL readout, the expression of multiple marker genes.
Figure 14B:
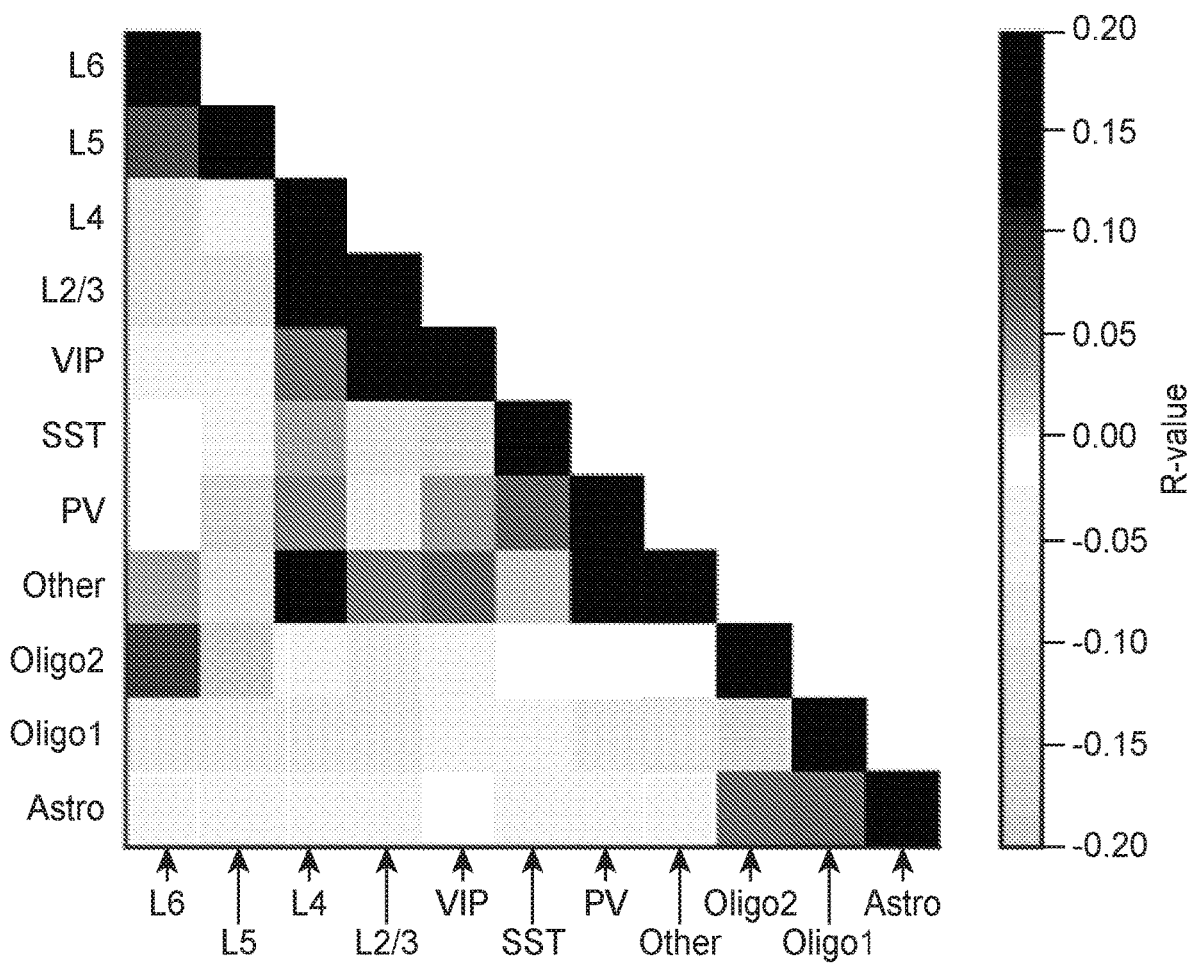

3D patterning of the 11 cell types (FIGS. 13E-13F) was consistent with the 160-gene thin-section tissue findings, but provided accurate and quantitative profiling of cellular distribution across space, with much larger cell numbers. Spatial histograms of excitatory, inhibitory, and non-neuronal cell types used the same labels as in FIG. 13D (FIG. 13E). Cells were counted in 5 µm bins in a 2D max-projection, and plotted in cell count/µm units as a function of distance from the corpus callosum (cc) to pia, averaged across the bins perpendicular to the cortical layers. A plot of max-projected cell locations was coded by cluster as in FIG. 13D (FIG. 13E, bottom). As reflected by both spatial-histogram (FIG. 13E) and correlational analyses (FIG. 14B), excitatory subtypes exhibited layered distribution, with the spatial density of each subtype decaying across space into adjacent layers. In contrast, inhibitory subtypes were more dispersed, albeit with layer preferences exhibited by the Vip subtype (largely located in layer 2/3), and the Sst and Pvalb subtypes (in layers 4 and 5). FIG. 14A depicted expression of each gene in 3D max projected in XY plane, showing spatial distributions of per-cell extracted gene expression values used for later clustering. Each gene z-scored per cell across all genes. FIG. 14B depicted voxel-wise correlation coefficient between distributions of each cell type, binned on a 25 µm grid.

Non-neuronal cells were largely seen in layer 1 and white matter. FIG. 13D depicted per-cell expression matrix of 28 genes from 32,845 single cells from one volume clustered into multiple excitatory, inhibitory, and non-neuronal cell types, z-scored across genes for each cell in order to normalize for mean differences in total signal between cells. Columns were sorted by order of sequencing rounds as conducted, in groups of 4. FIG. 13F depicted spatial distribution of each cell type (excitatory, inhibitory, non-neuronal) and subtypes in three dimensions. Each dot represented a single cell; spatial dimensions were in µm.

Figure 15A:
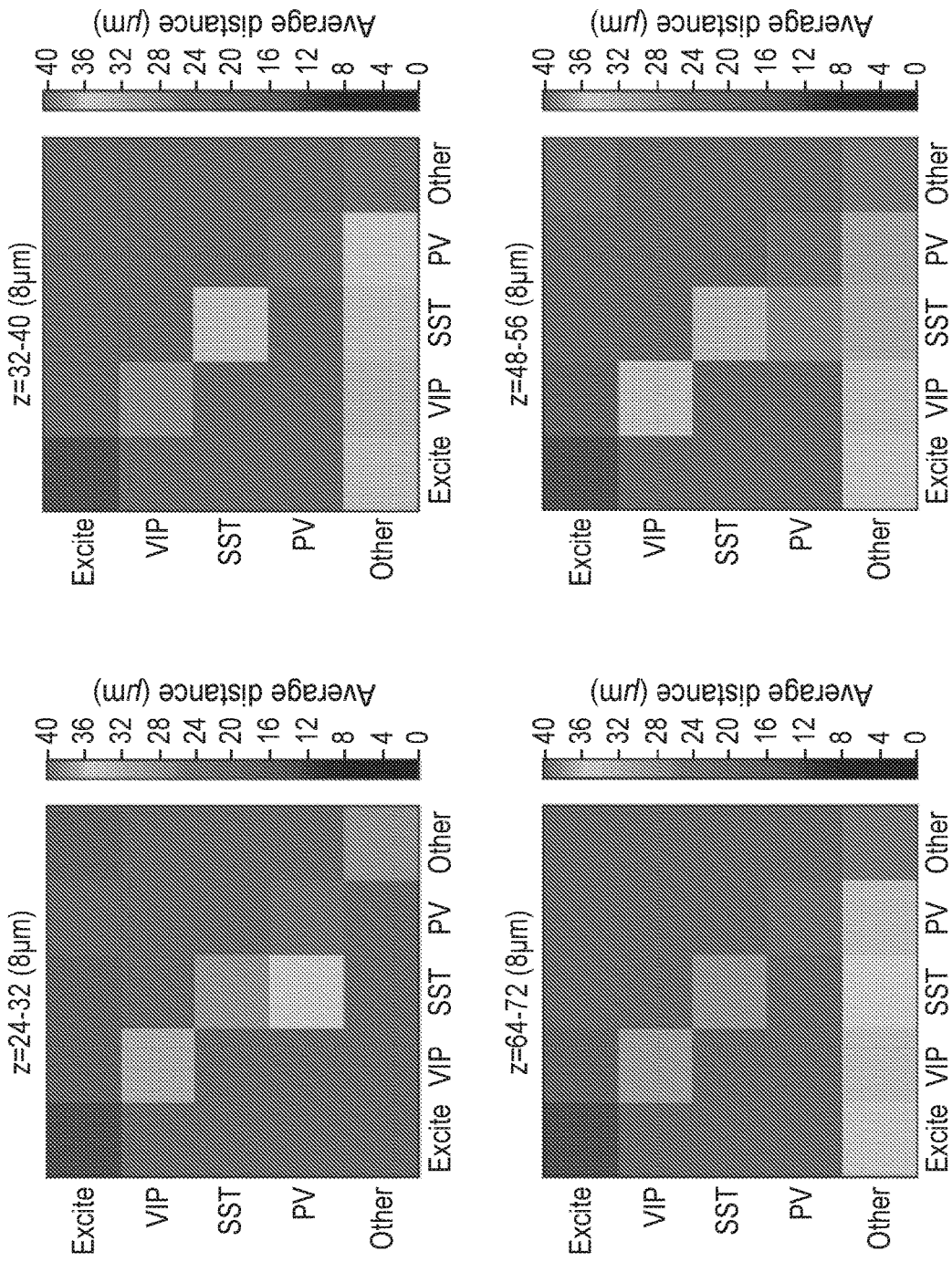
FIG. 15A-15C depict 2D nearest neighbor analysis of short-range inhibitory clusters in mouse primary visual cortex and cross-method validation.
Figure 15B:
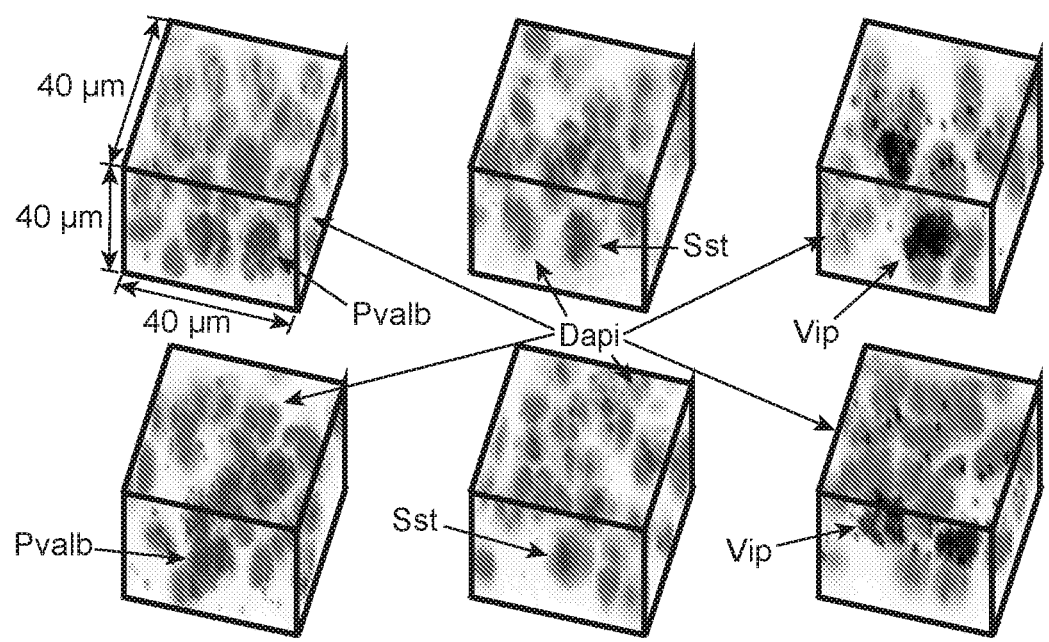
Figure 15C:
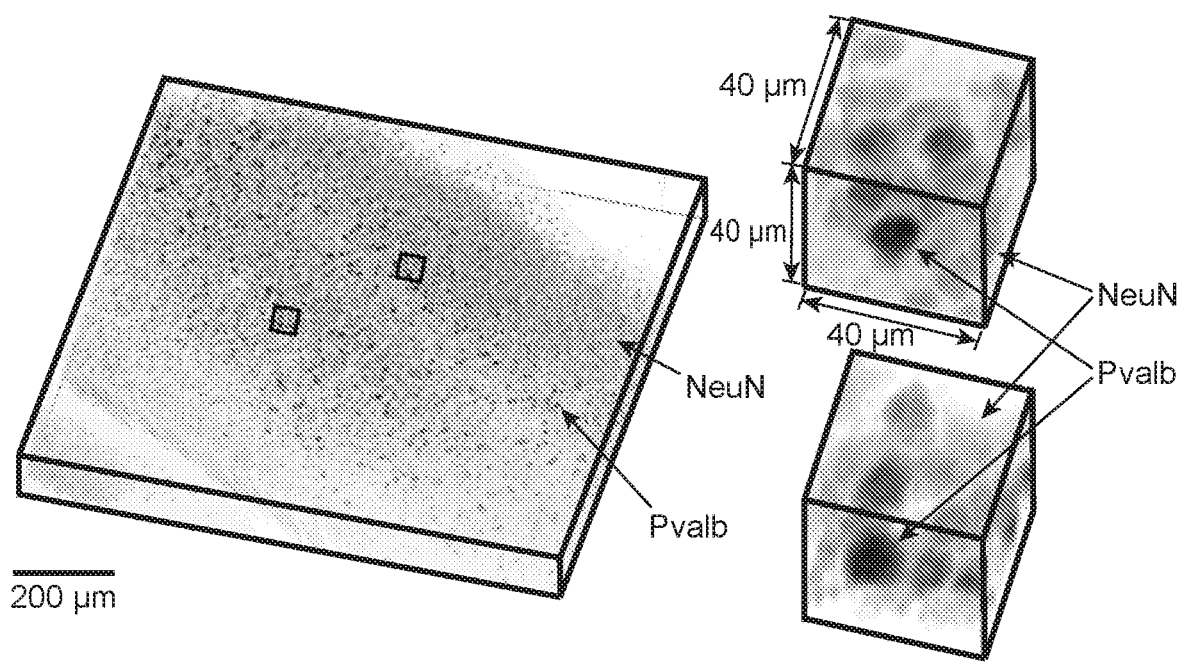

To discover finer volumetric patterns, the distribution of distances from each individual cell of each sequencing-defined subtype to its nearest-neighbours was analyzed, finding unexpectedly that the nearest neighbor of any inhibitory neuron tended to be its own subtype, rather than excitatory neurons or others inhibitory subtypes (FIG. 13G). Average nearest-neighbor distances computed in 3D between all excitatory cells (Excite) and each inhibitory cell type was depicted in FIG. 13G. For self-comparisons, the nearest neighbor was defined as the closest non-identical cell; the persistent self-correlation revealed self-clustering of inhibitory subtypes. If inhibitory neurons were randomly dispersed among the more abundant excitatory neurons in a purely salt-and-pepper distribution, the distance between inhibitory neurons would be larger than that from inhibitory to excitatory neurons (FIG. 13H). The same distances were analyzed as in FIG. 13H but shuffled (randomized) cell type labels were used. The actual intra-subtype distance of inhibitory neurons was much shorter (~15 µm, equivalent to the size of a single neuron, indicating direct somatic juxtaposition; FIG. 13I). FIG. 13I depicted nearest-neighbor distances computed in 3D between each inhibitory cell of a certain type and any member of the same type (Inhib·Inhib, eg VIP·VIP) or any excitatory neuron (Inhib·Excite); ****P<0.0001, Wilcoxon rank-sum test. FIG. 13I revealed a self-clustering organization of inhibitory subtypes across volumes that could only be accurately measured in 3D, but not in 2D (FIGS. 15A-15C). Average nearest neighbor distances between excitatory and different inhibitory cell types computed in the 2D projection of 8 µm (thinner than one cell) slices along z direction were taken within the same 3D volume shown in FIGS. 13A-13I (FIG. 15A). The 2D nearest-neighbor distances could not accurately estimate (overestimate) the 3D distances for the same cell types shown in FIG. 13D. Such patterning has the potential to be functionally relevant; for example, in-vivo imaging has suggested that inhibitory-neuron groupings in visual cortex could sharpen visual responses. FIG. 15B depicted examples of 3D short-range clusters of inhibitory neurons, zoomed view from FIG. 13C. FIG. 15C depicted short-range inhibitory neuron clusters observed in the primary visual cortex of transgenic mice (generated by crossing Parv-IRES-Cre and Ai14): Pvalb cells were by labeled tdtomato and all neuronal nuclei were immunostained with Alexa 647-conjugated anti-NeuN.

Example 8

Scalability of STARmap

Figure 16A:
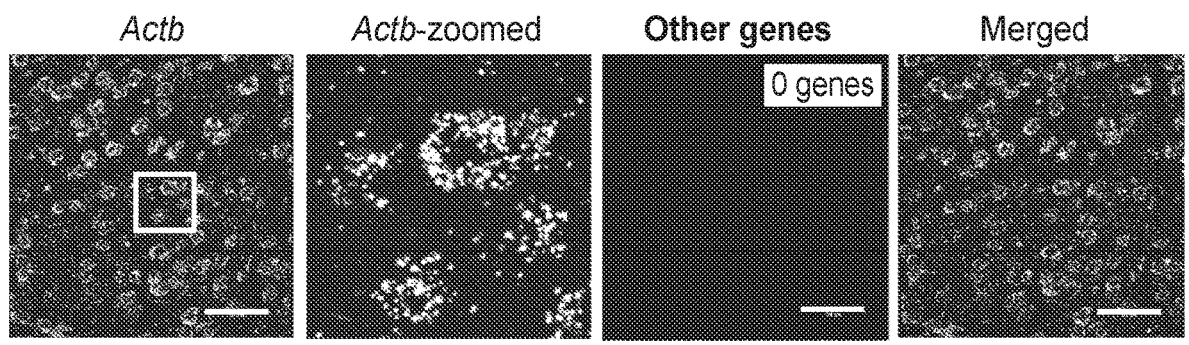
FIG. 16A-16E depict the scalability of STARmap.
Figure 16B:
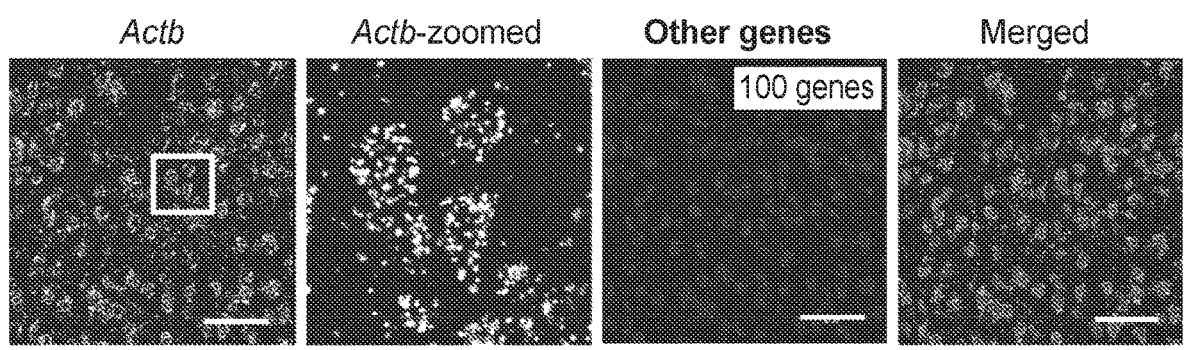
Figure 16C:
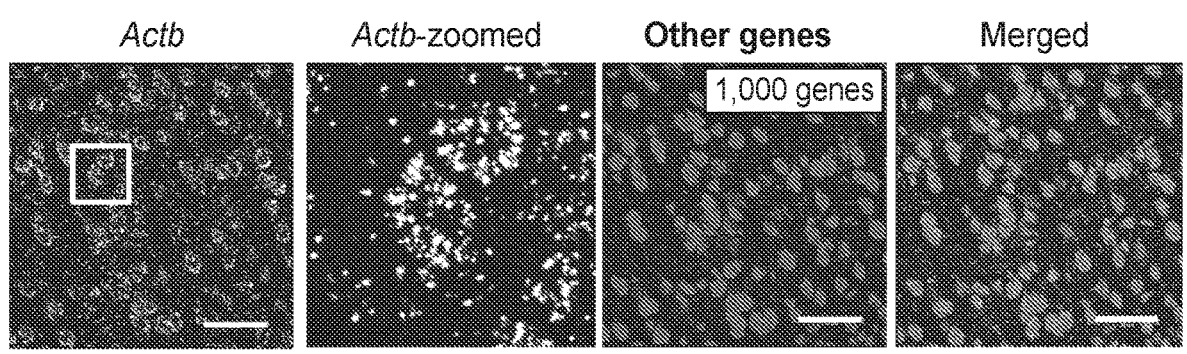
Figures 16D, 16E:
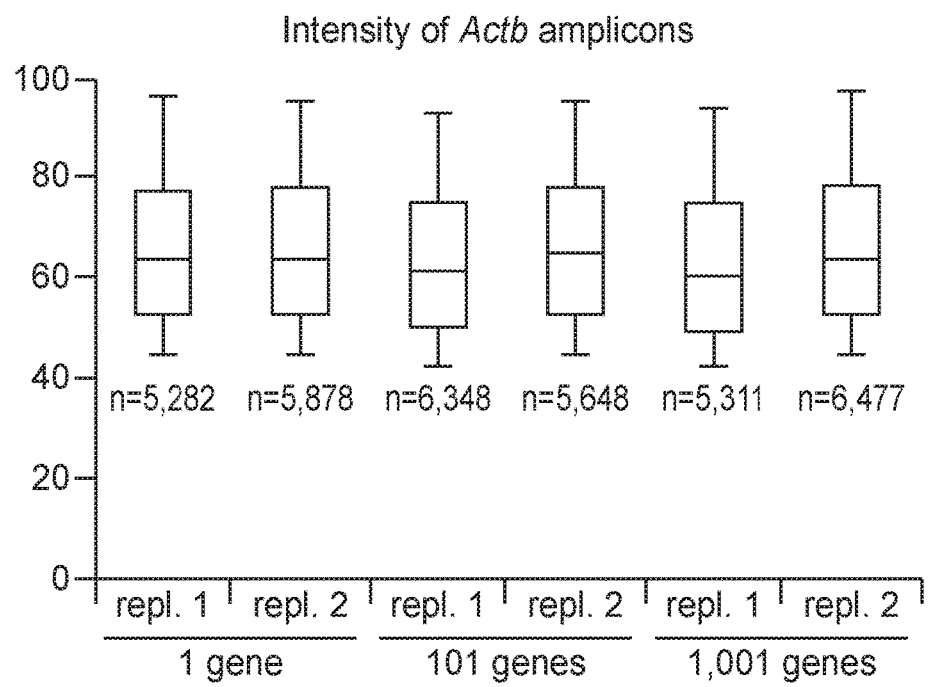

STARmap was adapted to longer sequencing lengths or higher gene numbers; there was no intrinsic limit to the number of genes or RNA species that can be simultaneously and quantitatively accessed by STARmap (FIGS. 16A-16E). FIG. 16A depicted the detection of Actb mRNA when increasing amounts of other RNAs were co-detected, to test for potential dilution effect of probe mixing along with the physical capacity of cells for SNAIL DNA amplicons. The SNAIL probe of Actb was designed with an orthogonal DNA sequence for detection and was spiked into the mix with probes of 0 (FIG. 16A), 100 (FIG. 16B) or 1,000 (FIG. 16C) other genes. If the SNAIL probe were less efficient when working in a mixture than working as a single probe, or if there were not enough space for rolling circle amplification, the Actb spike-in resulted in fewer amplicons, and/or the intensity of each amplicon was reduced. Fluorescence images were acquired in mouse visual cortex; Alexa546 channel of Actb amplicons; Alexa 647 channel of all other genes; DAPI staining of cell nuclei. Quantification of FIGS. 16A-16C was depicted in FIG. 16D. Box plots showed that any effects of dilution and cell space limitation were insignificant at least up to the scale of 1,000 genes. Box indicated first and third quartiles; middle line indicated median; whiskers indicated 5% and 95% data points; n indicated number of Actb amplicons across the 228×228×2 µm imaging volume; y axis: absolute fluorescence intensity. FIG. 16E depicted experimental and theoretical estimation of STARmap scalability. Coding indicated the 5-nt code can encode 1,024 genes; the SNAIL probe had 35-nt coding space in addition to the RNA-complementary sequence; SEDAL required 17-nt as a sequencing unit (11-nt docking region for reading probe plus 5-nt code and 1-nt flanking base) and thus the SNAIL probe held two such units and allowed $4^{10}$ ($10^6$) codes; with other sequencing methods for longer reads (e.g. SOLID, 18-nt for primer binding and 17-nt for coding), the upper limit approached $10^{11}$. Physical capacity was verified in mammalian neurons for up to 1,000 genes; since the physical size of the DNA amplicon was around 100-200 nm as determined by AFM and TEM, given that the diameter of a cell was around 15 µm and using a close-packed model (space efficiency 74%), estimated maximum capacity was 106 amplicons per cell. Optical volume was validated with the 1,020-gene experiments in mouse hippocampal cell culture and visual cortex experiments; amplicons/cell refers to those that had been successfully registered through all 6 sequencing rounds. As imaged by confocal microscopy, the mean diameter of the DNA amplicons is 400-600 nm; applying the same model as used in physical limits, the maximum capacity was $2 \times 10^4$ amplicons per cell. The experimental data for 1,020 genes approached this bound. Without being bound by any scientific theory, numerical differences between cell culture and tissue slices may be attributed to the following considerations: (1) whole cells were imaged in cell culture while cell fractions were imaged in tissue slices (8 µm, <1 cell thickness); (2) the hippocampal cell culture was less-differentiated compared to adult mouse brain, thus exhibiting a larger diversity of RNAs (more genes) per cell; (3) in contrast to the dense 3D packing of cells in brain tissue, cells cultured in vitro spread out considerably in the xy plane and became thinner in the z direction, while images in the xy plane exhibited higher optical resolution compared with in the z direction (voxel size 78×78×250 µm).

Example 9

Figure 17:
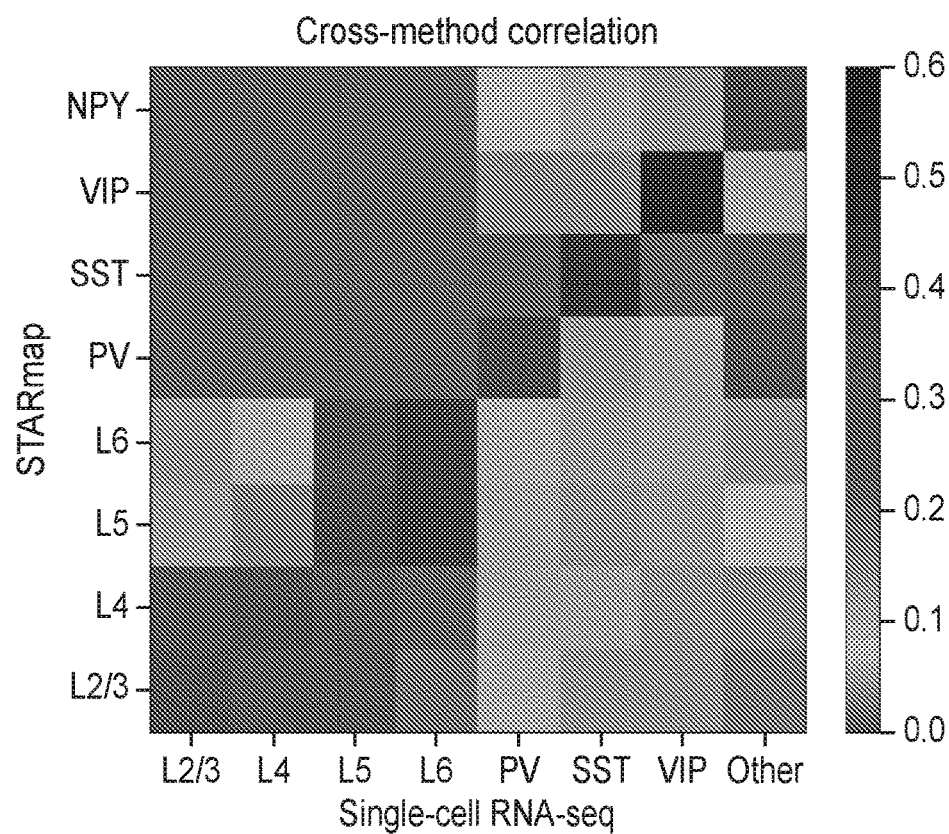
FIG. 17 depicts the correlation of neuron types identified in STARmap and published single-cell RNA sequencing results.

Correlation of Neuron Types Identified in STARmap 160-Gene Experiments and Published Single-Cell RNA Sequencing Results FIG. 17 depicted Pearson correlation of average gene expression across all genes within identified STARmap excitatory and inhibitory clusters, and corresponding clusters identified by single-cell RNA-seq from the Allen Brain Institute. See, e.g., Lein et al. (2007). For the single-cell RNA-seq data, the expression was averaged across all subtypes within a major type (e.g. L2/3), and only genes that were common between the single-cell RNA-seq and the 160-gene V1 experiment were used to compute the correlation; scale of 0-0.6, Pearson correlation coefficients.

Example 10

Figure 18A:
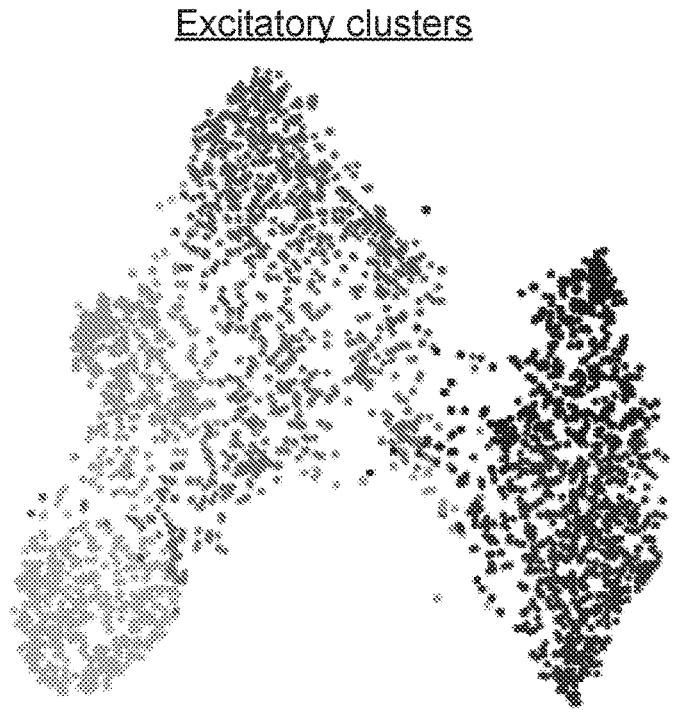
FIG. 18A-18F depict gene expression analysis of cell-type subclusters of medial prefrontal cortex (mPFC) using the methods described herein.
Figure 18B:
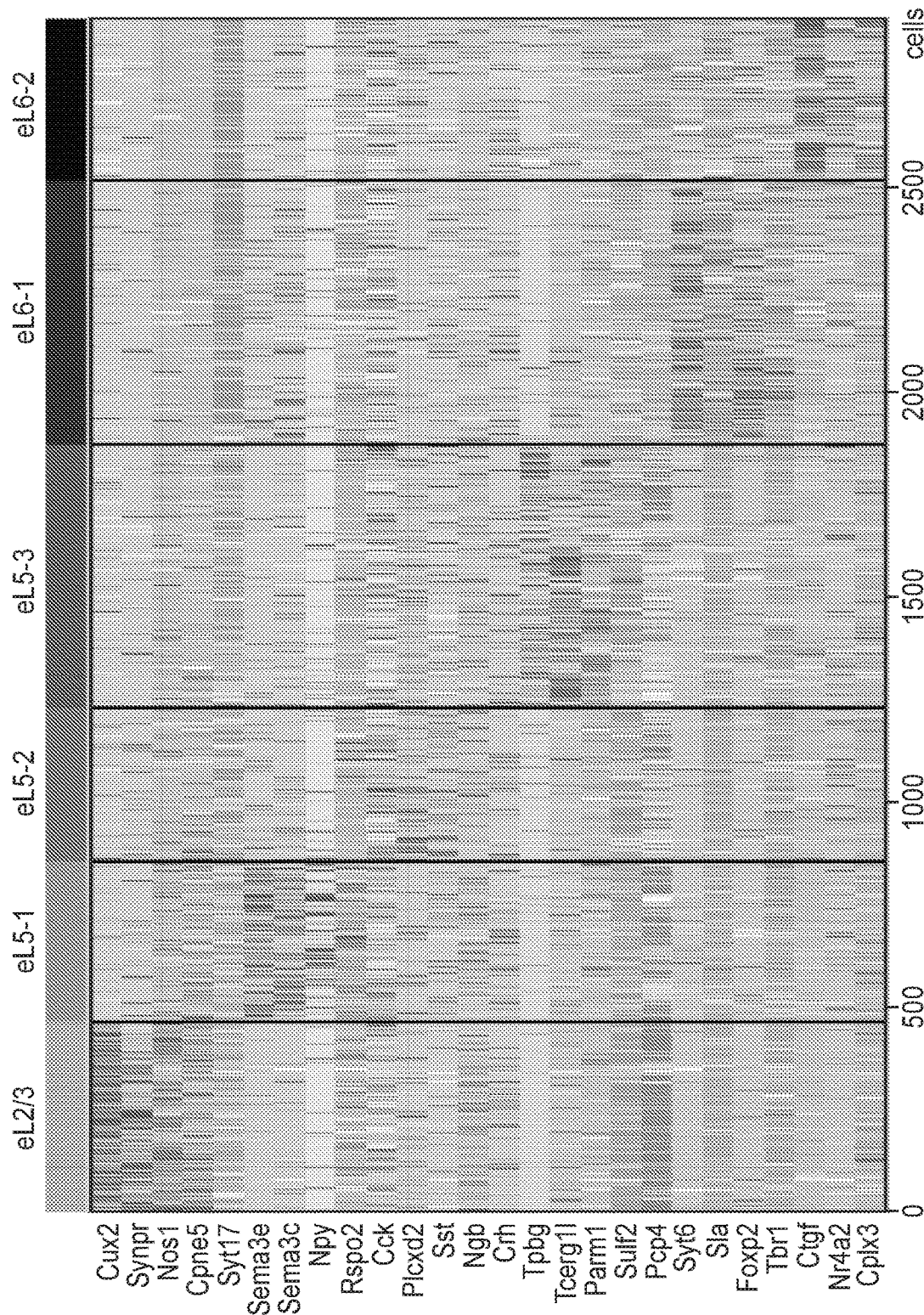
Figure 18C:
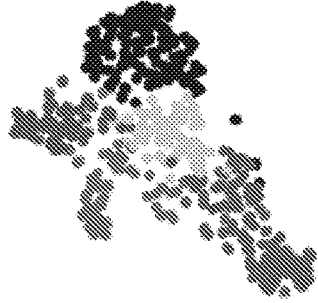
Figure 18E:
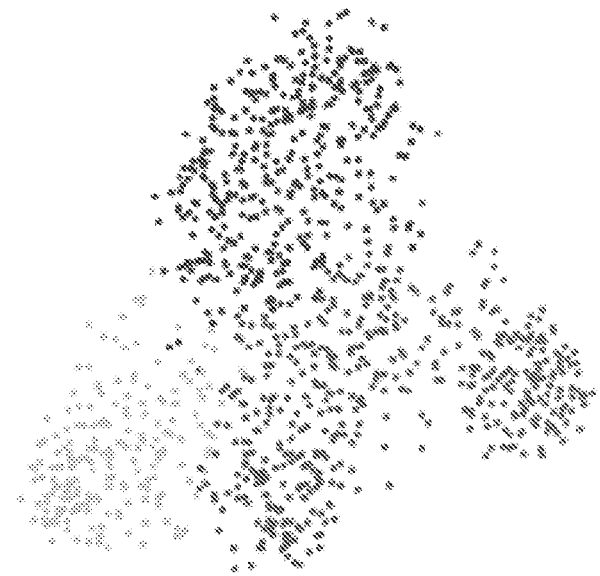
Figure 18D:
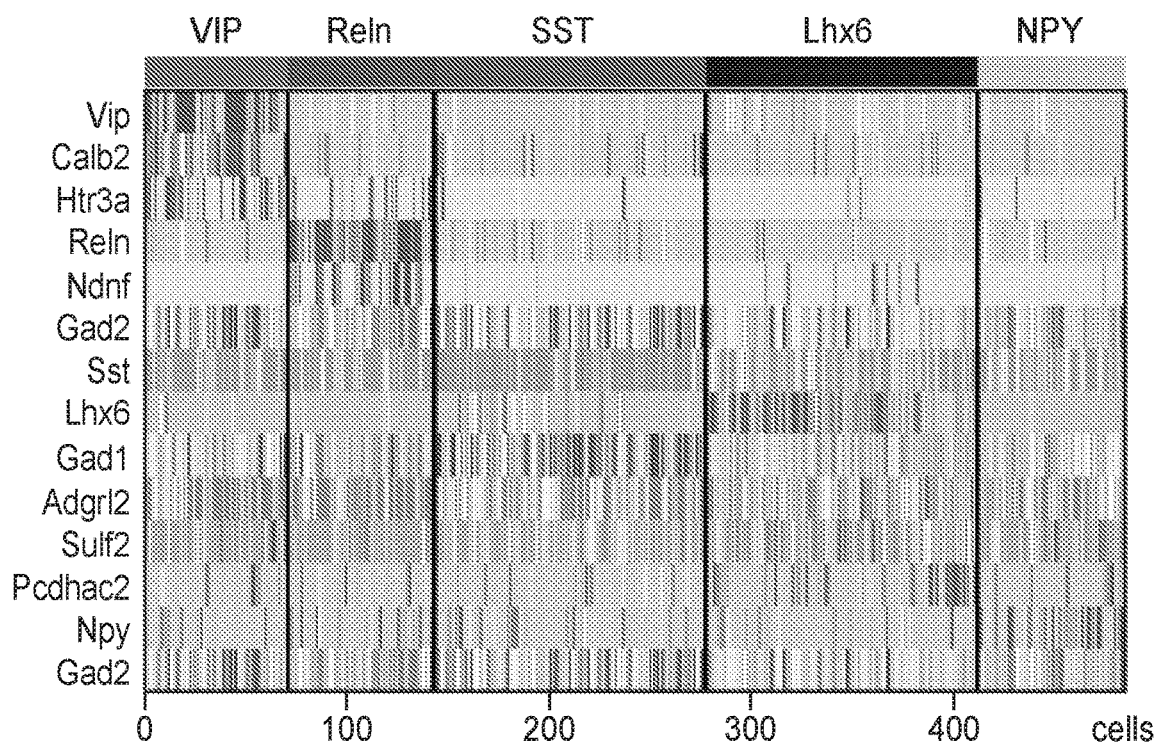
Figure 18F:
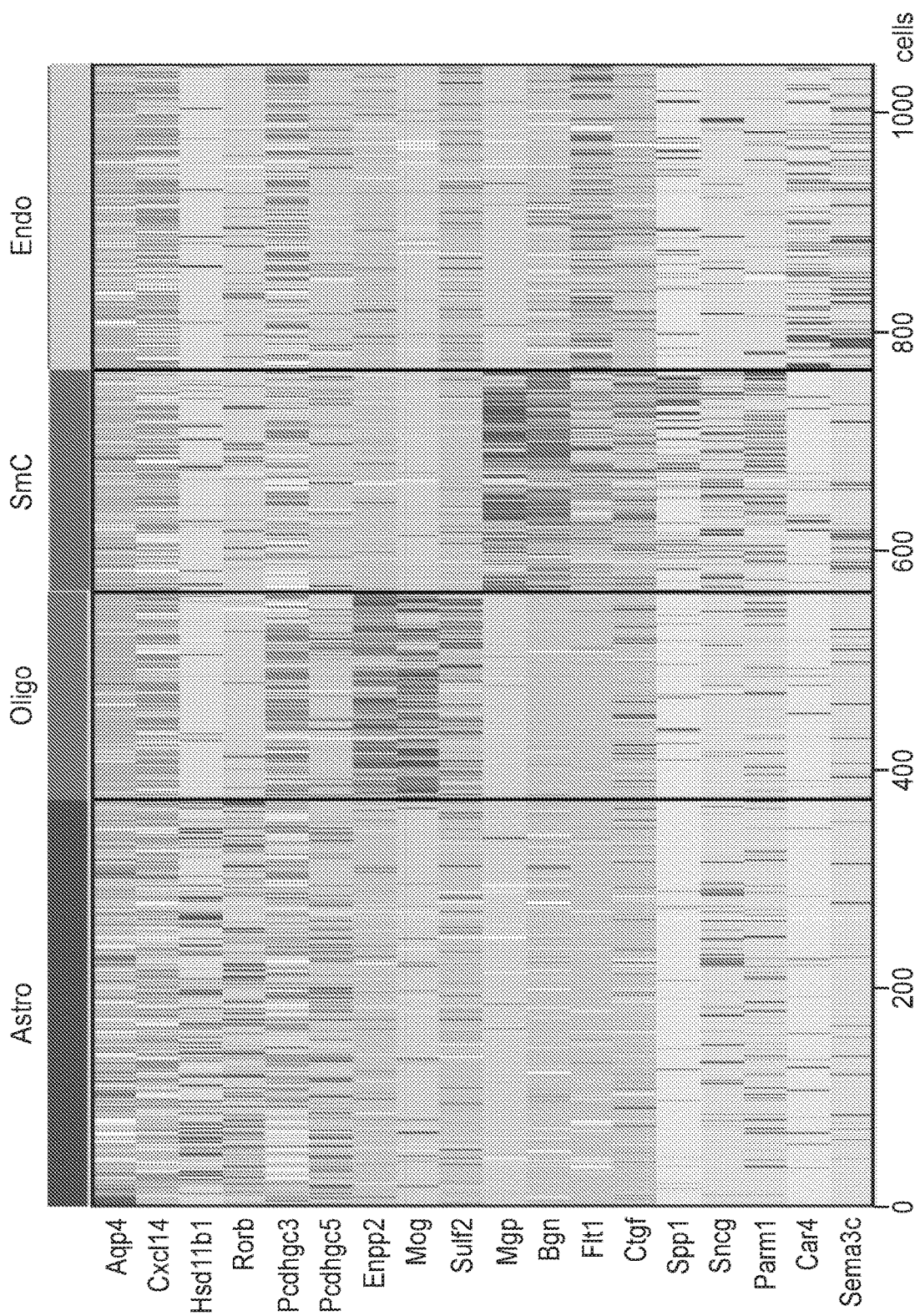

Gene Expression Analysis of Cell-Type Subclusters of Medial Prefrontal Cortex (mPFC) Using STARmap FIG. 18A depicted UMAP visualization of excitatory subclusters. FIG. 18B depicted differentially expressed genes per excitatory subcluster. FIG. 18C depicted UMAP visualization of inhibitory subclusters. FIG. 18D depicted differentially expressed genes per inhibitory subcluster. FIG. 18E depicted UMAP visualization of non-neuronal subclusters. FIG. 18F depicted differentially expressed genes per non-neuronal subcluster.

Figure 19B:
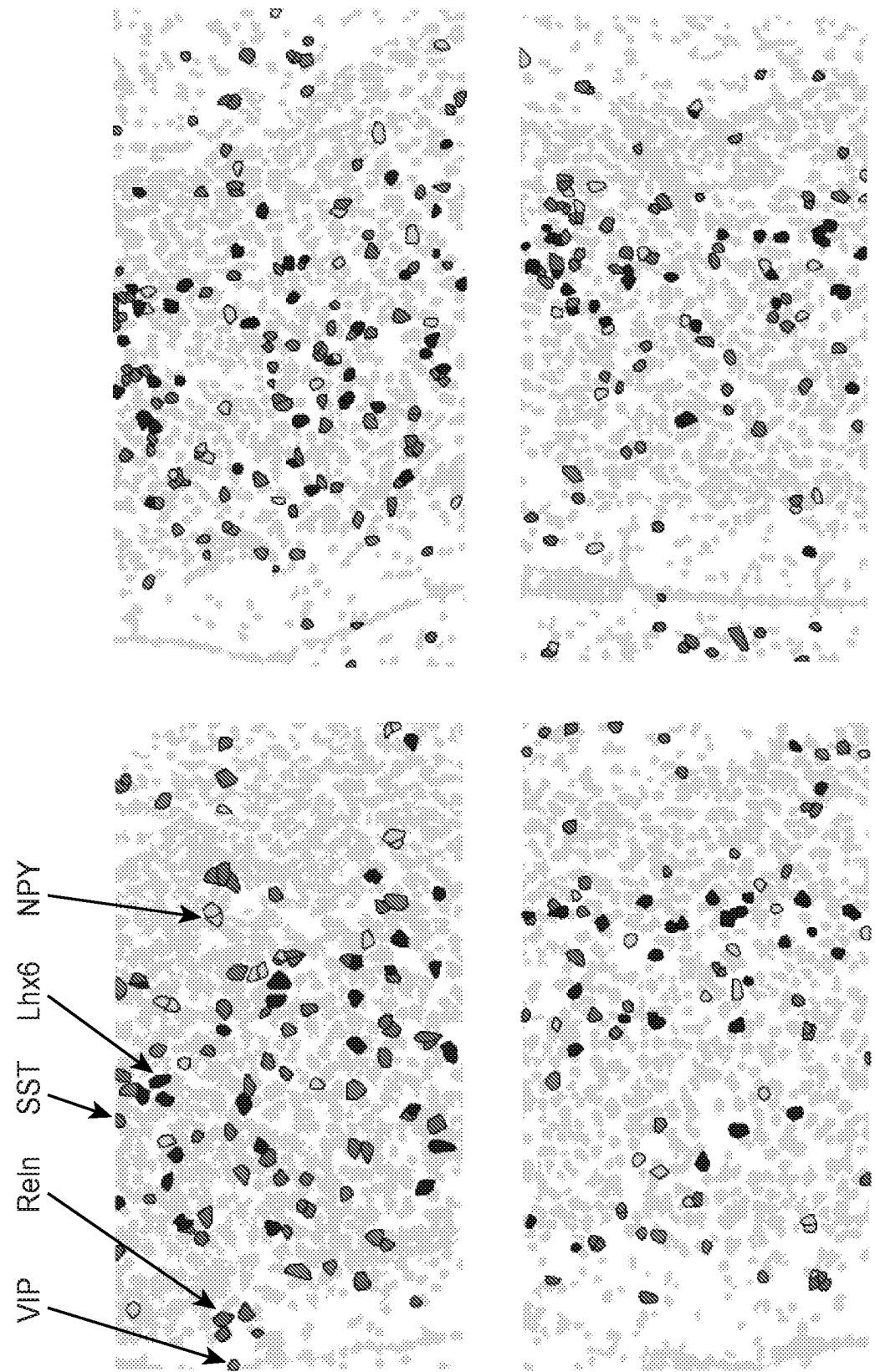

FIGS. 19A-19C depicted spatial maps across four biological replicates of excitatory subclusters (FIG. 19A), inhibitory subclusters (FIG. 19B), and non-neuronal subclusters (FIG. 19C).

Example 11

Figure 20A:
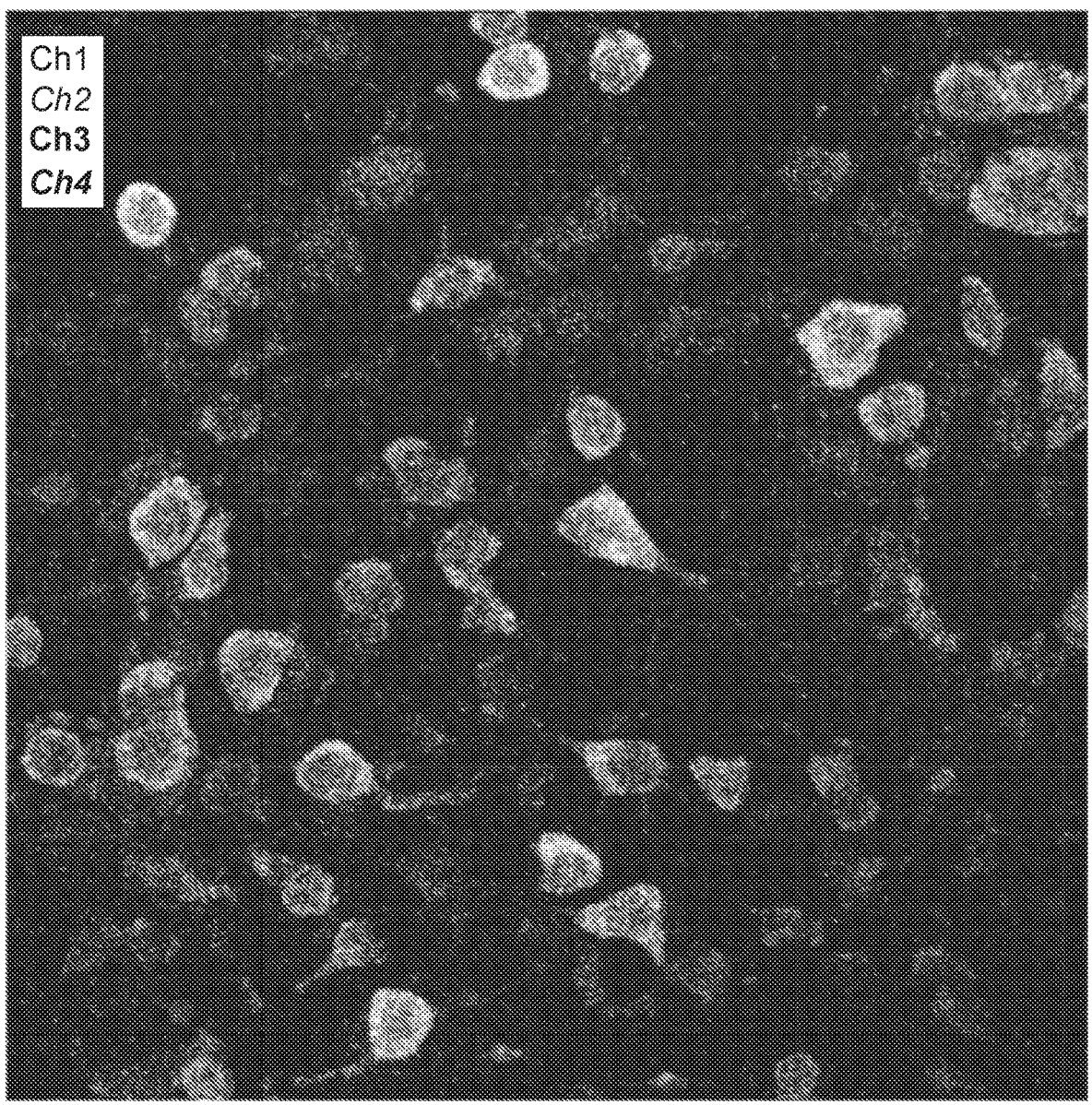
Figure 20B:
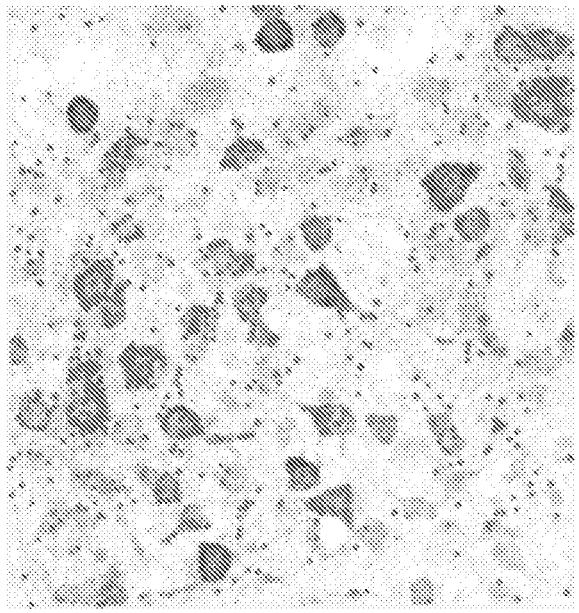
Figure 20B:
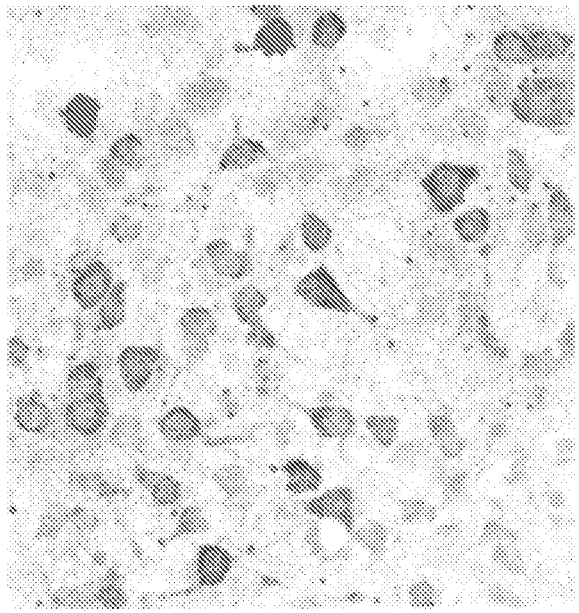
Figure 20B:
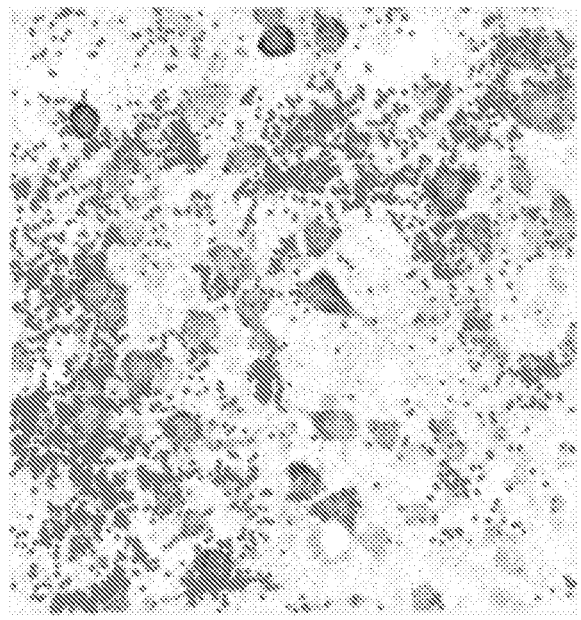
Figure 20B:
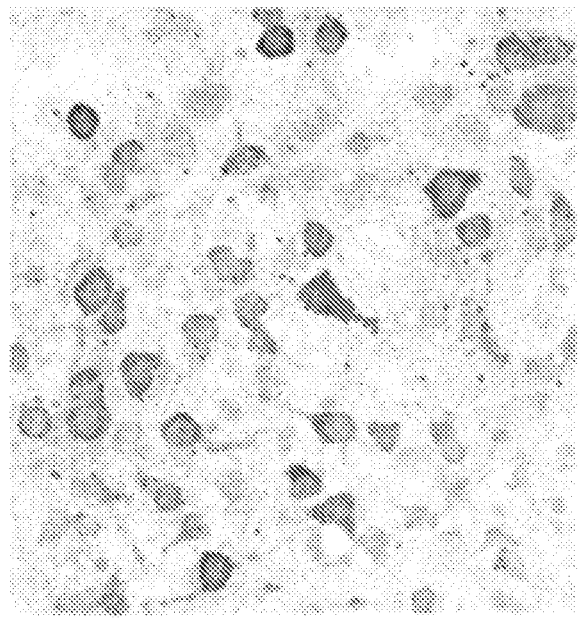

Gene Expression Analysis of Cell-Type Subclusters of 1020 Genes in Mouse Hippocampal Cell Culture FIG. 20A-20C depicted the analysis of 1020 genes in mouse hippocampal cell culture in 6-round sequencing using the methods described herein. FIG. 20A depicted faw fluorescence image merging four fluorescence channels of the first round. FIG. 20B depicted examples of cell type markers. Neuronal gene marker (Scna) was well separated from non-neuronal gene marker (Mt1) and the distribution of neuronal subtype markers (Reln, Sst) are distinct. FIG. 20C depicted the statistical analysis of amplicons and genes per cell, with an imaging area of 270×270 µm.

Figure 21A:
FIG. 21A-21C depict gene expression analysis of 1020 genes in mouse primary visual cortex using the methods described herein.
Figure 21A:
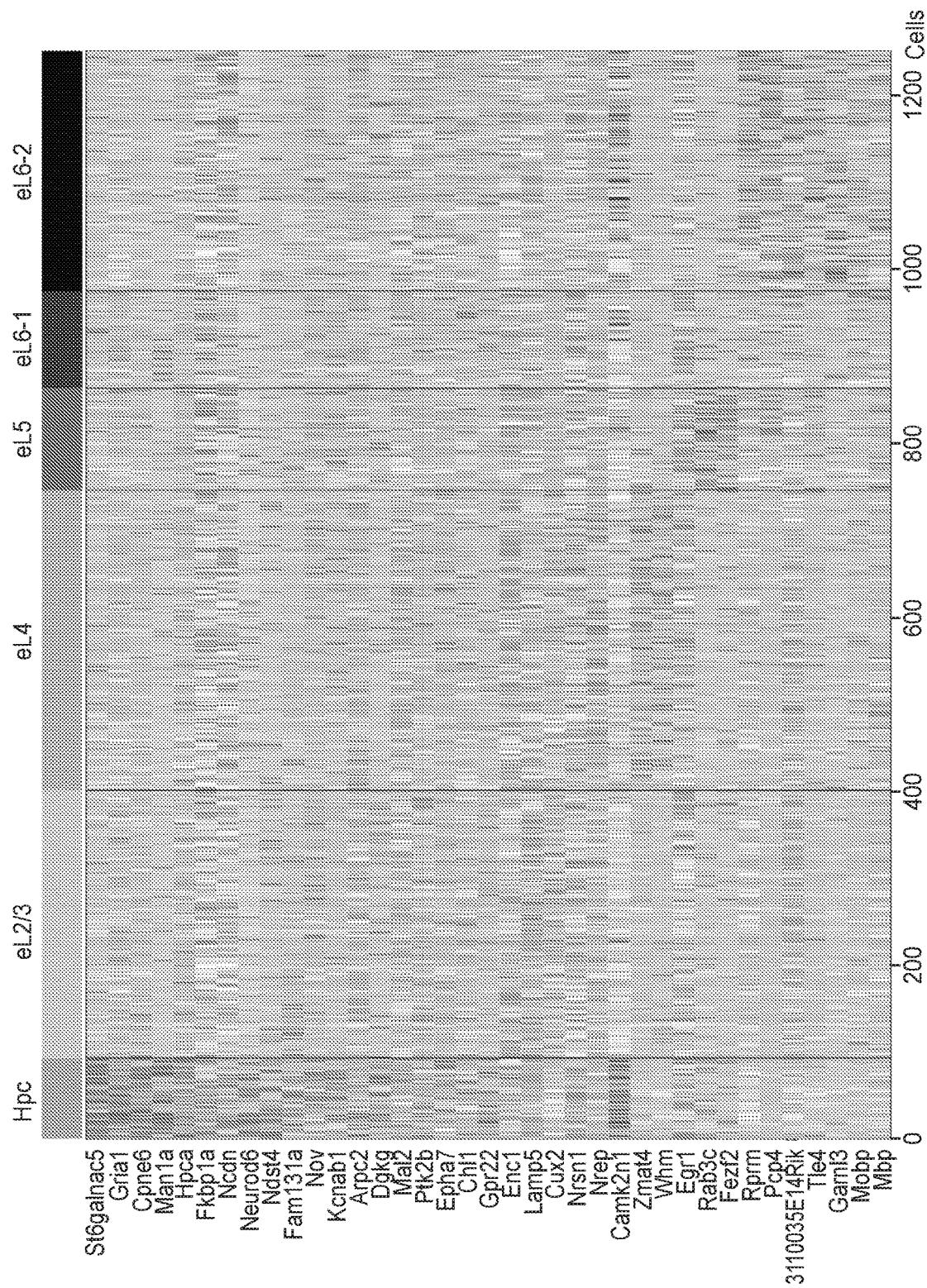
Figure 21B:
Figure 21B:
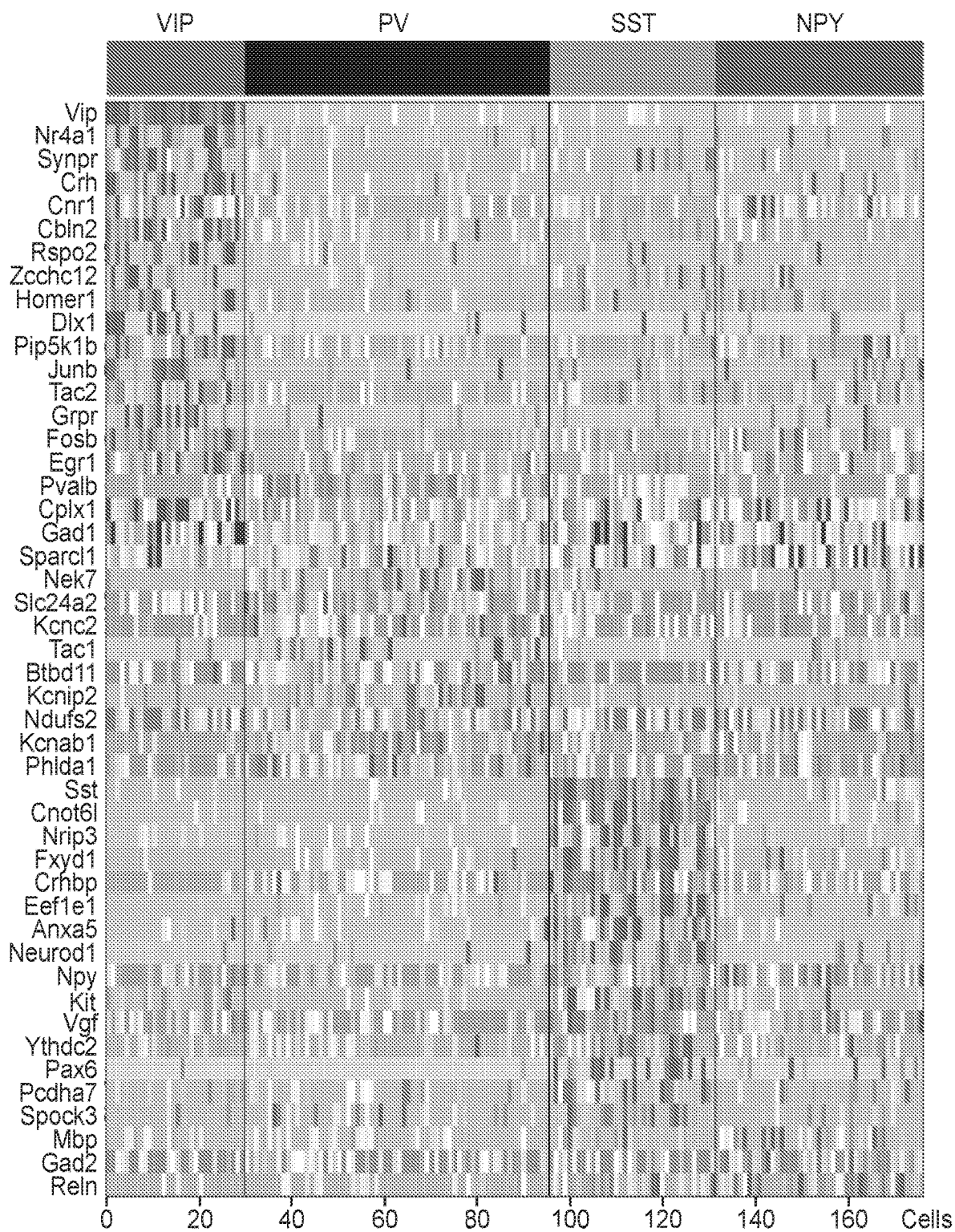
Figure 21C:
Figure 21C:
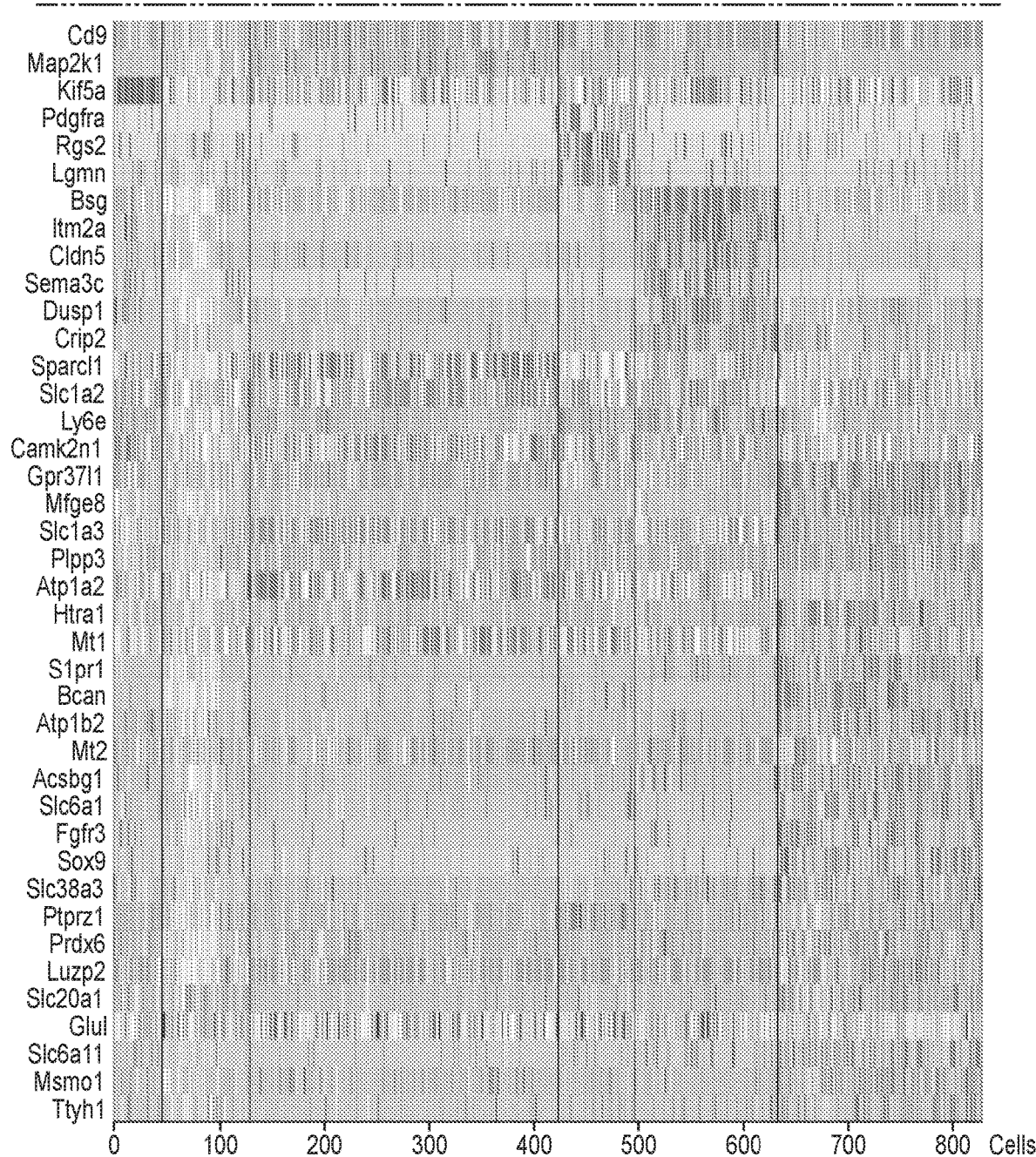

FIG. 21A-21C depicted additional gene expression information of 1020 genes in mouse primary visual cortex using the methods described herein. FIG. 21A depicted UMAP visualization of excitatory subclusters (FIG. 21A, left) and differentially expressed genes per excitatory subcluster (FIG. 21A, right). FIG. 21B depicted UMAP visualization of inhibitory subclusters (FIG. 21B, left) and differentially expressed genes per inhibitory subcluster (FIG. 21B, right). FIG. 21C depicted UMAP visualization of non-neuronal subclusters (FIG. 21C, left) and differentially expressed genes per non-neuronal subcluster (FIG. 21C, right).

Figure 22D:
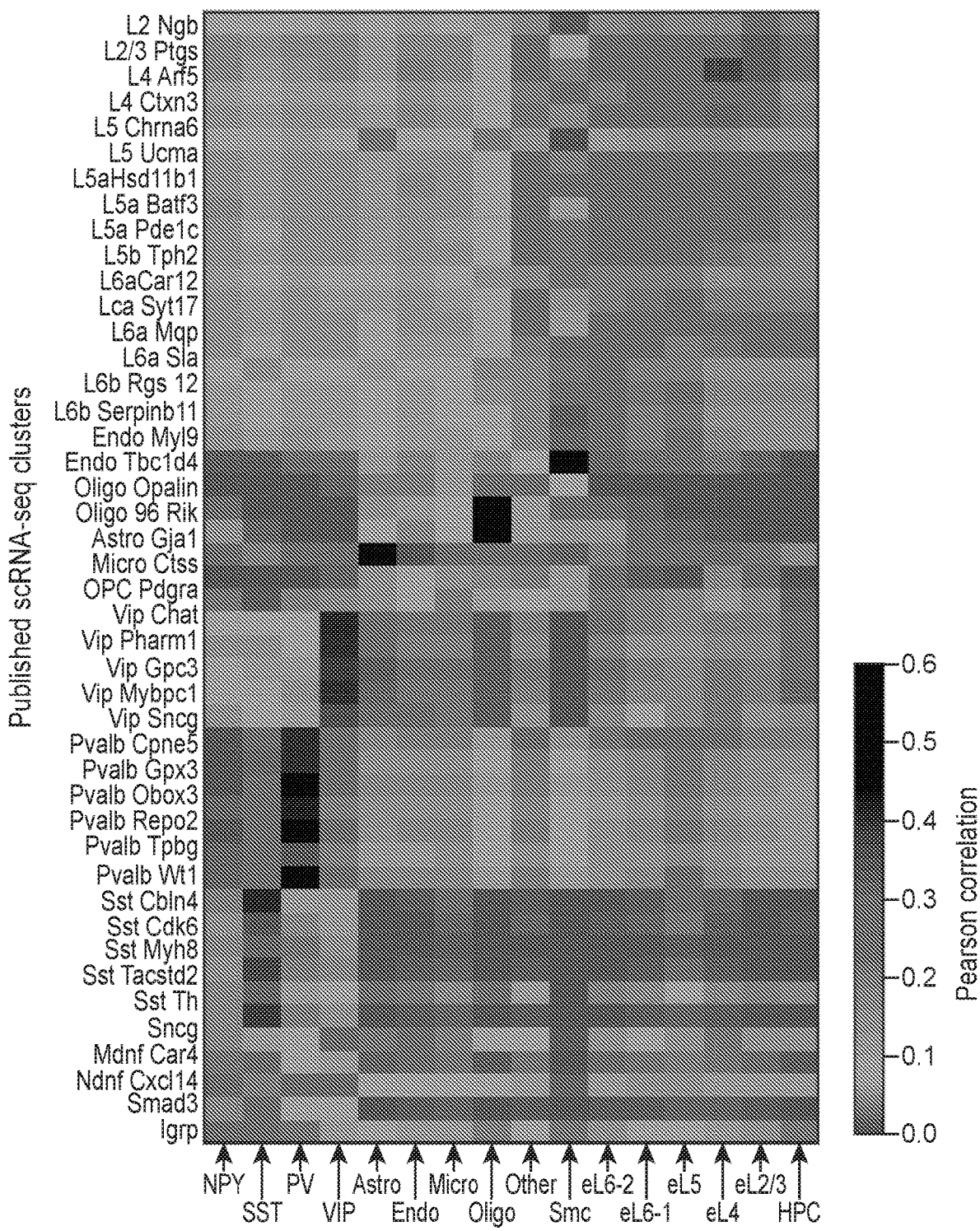

FIGS. 22A-22D depicted the reproducibility and cross-method comparison of measurements of 1020 genes in mouse primary visual cortex by STARmap. FIG. 22A depicted the correlation of reads per gene between two 1,020 gene replicates in visual cortex. FIG. 22B depicted a histogram of detected reads per cell (FIG. 22B, left) and detected genes per cell (FIG. 22B, right). FIG. 22C depicted a spatial map of cell types in other replicate of 1,020 gene visual cortex experiment. FIG. 22D depicted the Pearson correlation of average gene expression across all genes within identified STARmap 1,020 gene clusters, and corresponding clusters identified by single-cell RNA-seq from Allen Brain Institute.

Example 12

STARmap for Thin and Thick Tissue Slices

Figure 23A:
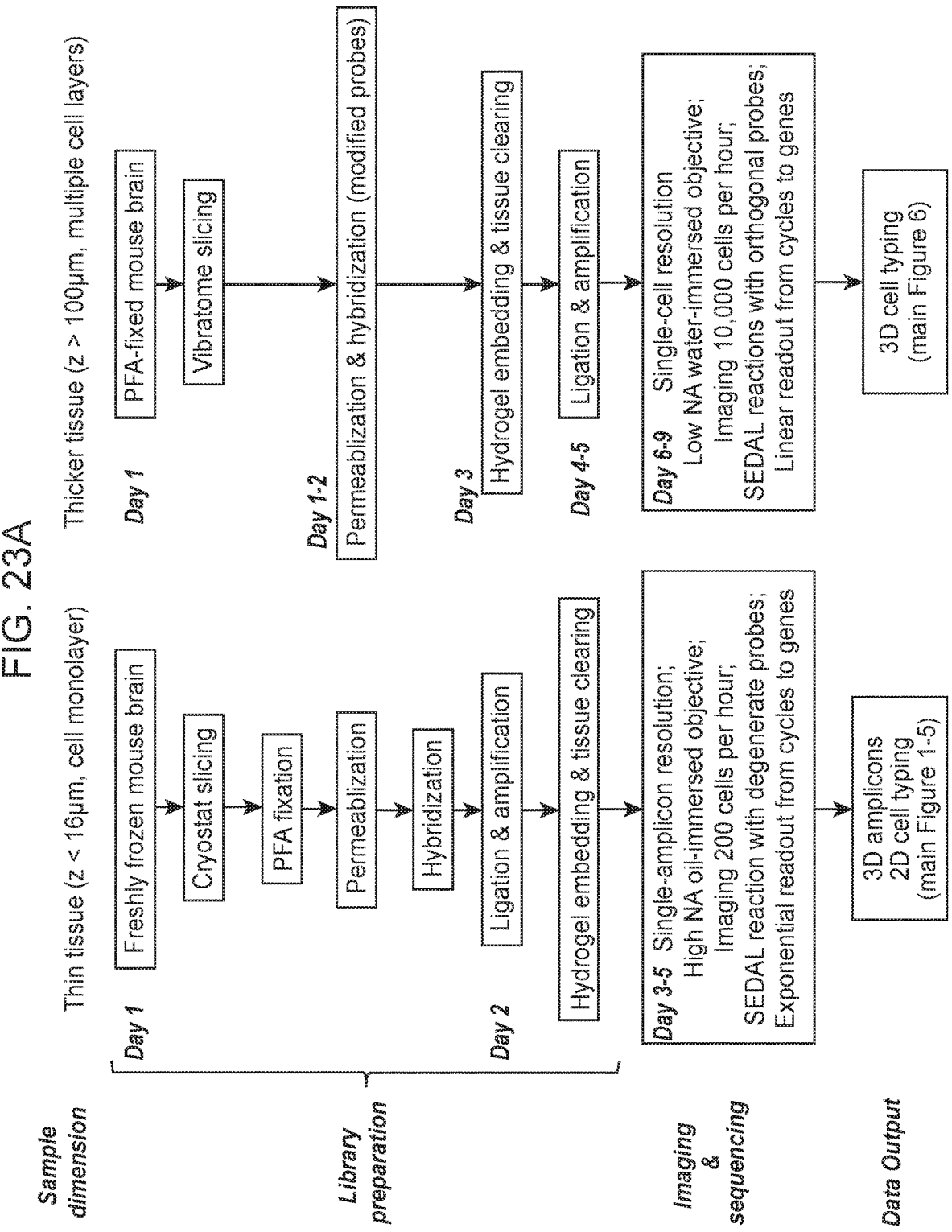

FIG. 23A depicted experimental flowcharts of STARmap for thin and thick tissues. FIG. 23B showed the preparation of modified primer probes for large volume experiments: DNA probes were ordered with 5'amine modification, pooled, and converted to a polymerizable moiety by AA-NHS. FIG. 23C showed experimental duration of different experimental design with various numbers of genes. FIG. 23D showed a comparison of RNA species, spatial resolution and throughput of STARmap with other single-cell approaches. Single-cell RNA sequencing may be combined with recently developed spatial transcriptome methods to gain regional spatial resolution (100 µm).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

1. N. Crosetto, M. Bienko, A. van Oudenaarden, Spatially resolved transcriptomics and beyond. Nat. Rev. Genet. 16, 57-66.
2. E. Lein, L. E. Borm, S. Linnarsson, The promise of spatial transcriptomics for neuroscience in the era of molecular cell typing. Science 358, 64-69 (2017).
3. E. Lubeck, L. Cal, Single-cell in situ RNA profiling by sequential hybridization. Nat. Methods 9, 743-748 (2012).

4. K. H. Chen, A. N. Boettiger, J. R. Moffitt, S. Wang, X. Zhuang, Spatially resolved, highly multiplexed RNA profiling in single cells. Science 348, aaa6090 (2015).
5. R. Ke et al., In situ sequencing for RNA analysis in preserved tissue and cells. Nat. Methods 10, 857-860 (2013).
6. J. H. Lee et al., Highly multiplexed subcellular RNA sequencing in situ. Science 343, 1360-1363 (2014).
7. N. A. Peppas, J. Z. Hilt, A. Khademhosseini, R. Langer, Hydrogels in biology and medicine: from molecular principles to bionanotechnology. Adv. Mater. 18, 1345-1360 (2006).
8. A. M. Rosales and K. S. Anseth, The design of reversible hydrogels to capture extracellular matrix dynamics. Nat. Rev. Mater. 1, 1-15 (2016).
9. R. Y. Tam, L. J. Smith, M. S. Shoichet, Engineering cellular microenvironments with photo- and enzymatically responsive hydrogels: toward biomimetic 3D cell culture models. Acc. Chem. Res. 50, 703-713 (2017).
10. K. Chung et al., Structural and molecular interrogation of intact biological systems. Nature 497, 332-337 (2013).
11. E. L. Sylwestrak, P. Rajasethupathy, M. A. Wright, A. Jaffe, K. Deisseroth, Multiplexed intact-tissue transcriptional analysis at cellular resolution. Cell 164, 792-804 (2016).
12. S. Shal et al., Single-molecule RNA detection at depth by hybridization chain reaction and tissue hydrogel embedding and clearing. Development 143, 2862-2867 (2016).
13. J. R. Moffitt et al., High-performance multiplexed fluorescence in situ hybridization in culture and tissue with matrix imprinting and clearing. Proc. Natl. Acad. Sci. U.S.A. 113, 14456-14461 (2016).
14. F. Chen et al., Nanoscale imaging of RNA with expansion microscopy. Nat. Methods 13, 679-684 (2016).
15. J. Shendure et al., Accurate multiplex polony sequencing of an evolved bacterial genome. Science. 309, 1728-1732 (2005).
16. J. H. Lee et al., Fluorescent in situ sequencing (FISSEQ) of RNA for gene expression profiling in intact cells and tissues. Nat. Protoc. 10, 442-458 (2015).
17. R. Drmanac et al., Human genome sequencing using unchained base reads on self-assembling DNA nanoarrays. Science 327, 78-81 (2010).
18. L. L. Glickfeld, R. C. Reid, M. L. Andermann, A mouse model of higher visual cortical function. Curr. Opin. Neurobiol. 24, 28-33 (2014).
19. B. Tasic et al., Adult mouse cortical cell taxonomy revealed by single cell transcriptomics. Nat. Neurosci. 19, 335-346 (2016).
20. A. Zeisel et al., Cell types in the mouse cortex and hippocampus revealed by single-cell RNA-seq. Science 347, 1138-1142 (2015).
21. T. K. Kim et al., Widespread transcription at neuronal activity-regulated enhancers. Nature 465, 182-187 (2010).
22. A. R. Mardinly et al., Sensory experience regulates cortical inhibition by inducing IGF-1 in VIP neurons. Nature 531, 371-375 (2016).
23. S. Hrvatin et al., Single-cell analysis of experience-dependent transcriptomic states in the mouse visual cortex. Nat. Neurosci. 21, 120-129 (2018).
24. E. S. Lein et al., Genome-wide atlas of gene expression in the adult mouse brain. Nature 445, 168-176 (2007).
25. K. Shekhar et al., Comprehensive classification of retinal bipolar neurons by single-cell transcriptomics. Cell 166, 1308-1323 (2016).
26. J. Y. Joo et al., Stimulus-specific combinatorial functionality of neuronal c-fos enhancers. Nat. Neurosci. 19, 75-83 (2016).
27. T. Ebina et al., 3D clustering of GABAergic neurons enhances inhibitory actions on excitatory neurons in the mouse visual cortex. Cell Rep. 9, 1896-1907 (2014).
28. A. Paul et al., Transcriptional architecture of synaptic communication delineates GABAergic neuron identity. Cell 171, 522-539 (2017).
29. T. N. Lerner, L. Ye, K. Deisseroth, Communication in neural circuits: tools, opportunities, and challenges. Cell 164, 1136-1150 (2016).
30. A. McDavid et al., Data exploration, quality control and testing in single-cell qPCR-based gene expression experiments. Bioinformatics 15, 461-467 (2013).
31. J. L. Bentley, Multidimensional binary search trees used for associative searching. Commun. ACM 18, 509-517 (1975).

What is claimed is:

1. A method for identifying a nucleic acid in a cell within a tissue, comprising:
    (a) contacting the tissue with at least a pair of oligonucleotides under conditions to allow for specific hybridization of the pair of oligonucleotides to the nucleic acid, wherein the pair of oligonucleotide comprises:
        (i) a first oligonucleotide, wherein the first oligonucleotide comprises a first complementarity region, a second complementarity region, and a third complementarity region; and
        (ii) a second oligonucleotide, wherein the second oligonucleotide comprises a fourth complementarity region, a fifth complementarity region, and a sixth complementarity region; and
        wherein the first complementarity region is complementary to a first portion of the nucleic acid, the second complementarity region is complementary to the fourth complementarity region, the third complementarity region is complementary to the sixth complementarity region, the fifth complementarity region is complementary to a second portion of the nucleic acid, wherein the first complementarity region and fifth complementarity region are hybridized to the nucleic acid;
    (b) performing an amplification reaction on the nucleic acid having the pair of oligonucleotides hybridized thereto to yield one or more amplicons, wherein the one or more amplicons are embedded in a hydrogel; and
    (c) imaging the one or more amplicons to identify the nucleic acid.

2. The method of claim 1, further comprising, subsequent to (b), clearing the tissue of a plurality of cellular components.

3. The method of claim 2, wherein the cellular components comprise lipids, proteins, or any combination thereof.

4. The method of claim 1, wherein the pair of oligonucleotides are denatured by heating before contacting the tissue.

5. The method of claim 1, wherein the cell is present in a population of cells.

6. The method of claim 5, wherein the population of cells comprises a plurality of cell types.

7. The method of claim 1, wherein the tissue is fixed and permeabilized with a single solution.

8. The method of claim 1, wherein the nucleic acid is ribonucleic acid (RNA).

9. The method of claim 1, wherein the nucleic acid is messenger RNA.

10. The method of claim 1, wherein the nucleic acid is DNA.

11. The method of claim 1, wherein the second oligonucleotide is provided as a closed nucleic acid circle.

12. The method of claim 1, wherein:
(i) the second oligonucleotide comprises a padlock probe,
(ii) the first complementarity region of the first oligonucleotide has a length of 19 nucleotides to 25 nucleotides,
(iii) the second complementarity region of the first oligonucleotide has a length of 3 nucleotides to 10 nucleotides,
(iv) the third complementarity region of the first oligonucleotide has a length of 3 nucleotides to 10 nucleotides,
(v) the fourth complementarity region of the second oligonucleotide has a length of 3 nucleotides to 10 nucleotides,
(vi) the fifth complementarity region of the second oligonucleotide has a length of 19 nucleotides to 25 nucleotides,
(vii) the sixth complementarity region of the second oligonucleotide has a length of 3 nucleotides to 10 nucleotides,
(viii) the fourth complementarity region of the second oligonucleotide comprises a 5' end of the second oligonucleotide,
(ix) the sixth complementarity region of the second oligonucleotide comprises a 3' end of the second oligonucleotide,
(x) the fourth complementarity region of the second oligonucleotide is adjacent to the sixth complementarity region of the second oligonucleotide or any combination thereof.

13. The method of claim 1, wherein
(i) a third oligonucleotide is configured to decode bases; and
(ii) a fourth oligonucleotide is configured to convert the decoded bases into a signal.

14. The method of claim 1, wherein the imaging comprises imaging the one or more amplicons that are embedded in hydrogel using a microscopy selected from the group consisting of confocal microscopy, widefield fluorescence microscopy, two-photon microscopy, light-field microscopy, intact tissue expansion microscopy, super-resolution microscopy, and light sheet microscopy.

15. The method of claim 14, wherein the light sheet microscopy is CLARITY-optimized light sheet microscopy (COLM).

16. The method of claim 1, wherein the tissue has a thickness of 5 micrometers (μm) to 20 μm.

17. The method of claim 1 wherein the tissue is a thick slice having a thickness of 5 μm to 200 μm.

18. A method of screening a candidate agent to determine whether the candidate agent modulates gene expression of the nucleic acid in the cell in the tissue, comprising: performing the method of claim 1 to determine gene sequencing of the nucleic acid in the cell in the tissue, and
detecting a level of gene expression of the nucleic acid, wherein an alteration in the level of gene expression of the nucleic acid in the presence of the candidate agent relative to the level of expression of the nucleic acid in the absence of the at least one candidate agent indicates that the at least one candidate agent modulates gene expression of the nucleic acid in the cell in the tissue.

19. The method of claim 18, wherein the detecting comprises determining a signal.

20. The method of claim 19, wherein the signal is a fluorescent signal.

21. The method of claim 1, further comprising adding a ligase to ligate a first end of the second oligonucleotide to a second end of the second oligonucleotide thereby generating a closed nucleic acid circle.

22. The method of claim 21, wherein the ligase is a DNA ligase.

23. The method of claim 1, wherein the amplification reaction comprises rolling circle amplification, and wherein the second oligonucleotide is a template and the first oligonucleotide is a primer for a polymerase to form one or more amplicons.

24. The method of claim 1, wherein the one or more amplicons is embedded in the hydrogel after the amplification reaction of (b).

25. The method of claim 1, wherein the one or more amplicons is embedded in the hydrogel by copolymerizing the one or more amplicons with acrylamide.

26. The method of claim 1, wherein the tissue is embedded in the hydrogel prior to (b).

27. The method of claim 1, wherein the first portion of the nucleic acid and the second portion of the nucleic acid are separated by one or more nucleotides.

28. The method of claim 1, wherein the first complementarity region is adjacent to the fifth complementarity region.

* * * * *